US006617171B2

(12) United States Patent
Faustman et al.

(10) Patent No.: US 6,617,171 B2
(45) Date of Patent: Sep. 9, 2003

(54) METHODS FOR DIAGNOSING AND TREATING AUTOIMMUNE DISEASE

(75) Inventors: Denise L. Faustman, Weston, MA (US); Takuma Hayashi, Cambridge, MA (US)

(73) Assignee: The General Hospital Corporation, Boston, MA (US)

( * ) Notice: Subject to any disclaimer, the term of this patent is extended or adjusted under 35 U.S.C. 154(b) by 0 days.

(21) Appl. No.: 09/031,629

(22) Filed: Feb. 27, 1998

(65) Prior Publication Data

US 2002/0106689 A1 Aug. 8, 2002

(51) Int. Cl.$^7$ ............................................. G01N 33/566

(52) U.S. Cl. ......................................... 436/506; 435/7.1

(58) Field of Search ........................... 436/506; 435/7.1

(56) References Cited

U.S. PATENT DOCUMENTS

| | | | | |
|---|---|---|---|---|
| 5,506,213 A | | 4/1996 | Carson et al. ................. | 514/46 |
| 5,538,854 A | * | 7/1996 | Faustman ................... | 435/7.24 |
| 5,888,511 A | | 3/1999 | Skurkovich et al. ...... | 424/145.1 |
| 5,962,516 A | | 10/1999 | Qi et al. ....................... | 514/468 |
| 6,117,911 A | | 9/2000 | Grainger et al. ............ | 514/648 |

FOREIGN PATENT DOCUMENTS

| | | |
|---|---|---|
| WO | WO 95/24914 | 9/1995 |
| WO | WO 95/25533 | 9/1995 |
| WO | WO 96/13266 | 5/1996 |

OTHER PUBLICATIONS

The Merck Manual of Diagnosis and Therapy. 17$^{th}$ Edition pp. 1061–1064, 1999.*
Textbook of the Autoimmune Diseases, Lahita et al. 2000, pp. 834–836.*
Kevin G. Becker et al., Proceedings of the National Academy of Sciences of the USA, vol. 95, Issue 17, 9979–9984, Aug. 18, 1998.
Heward et al., Clinical Science vol. 93, 479–491, 1997.
Aristarkov, et al., 1996, EZ–C, a cyclin–selective ubiquitin carrier protein required for the destruction of mitotic cyclins, *Proc. Natl. Acad. Sci. U.S.A.*, 93(9): 4294–4299.
Boches, et al., 1982, Role for the Adenosine Trihosphate–Dependent Proteolytic Pathway in Reticulocyte Maturation, *Science*, 215: 978–980.
Ciechanover, et al., 1984, Ubiquitin Dependence of Selective Protein Degradation Demonstrated in the Mammalian Cell Cycle Mutant ts85, *Cell*, 37: 35–66.
Driscoll, et al., 1990, The Proteasome (Multicatalytic Protease) Is a Component of the 1500–kDa Proteolytic Complex Which Degrades Ubiquitin–conjugated Proteins, *The Journal of Biological Chemistry*, 265: 4789–4792.

Eytan, et al., 1989, ATP–dependent incorporation of 20S protease into the 26S complex that degrades proteins conjugated to ubiquitin, *Proc. Natl. Acad. Sci. U.S.A.*, 86: 7751–7755.
Ganoth et al., 1988, A Multicomponent System That Degrades Proteins Conjugated to Ubiquitin, *The Journal of Biological Chemistry*, 263: 12412–12419.
Goldberg, 1992, The mechanism and functions of ATP–dependent proteases in bacterial and animal cells, European Journal of Biochemistry, 203: 9–23.
Goldberg, et al., 1992, Proteolysis, protoeasomes and antigen presentation, *Nature*, 357: 375–379.
Grilli, et al., 1996, Neuroprotection by Aspirin and Sodium Salicylate Through Blockade of NF–kB Activation, *Science*, 274: 1383–1385.
Gronostajski, et al., 1985, The ATP Dependence of the Degradatin of Short– and Long–lived Proteins in Growing Fibroblasts, *The Journal of Biological Chemistry*, 260: 3344–3349.
Haas and Siepmann, 1997, Pathways of ubiquitin conjugation, *FASEB Journal*, 11: 1257–1268.
Hershko and Ciechanover, 1992, The Ubiquitin System for Protein Degradation, *Annual Review of Biochemistry*, 61:761–807.
Honda, et al., 1997, Oncoprotein MDM2 is a ubiquitin ligase E3 for tumor suppressor p53, *FEBS Letters*, 420: 25–27.
Hopkin, Karen, 1997, Regulating Cellular Processes, The Power of Protein Degradation, *The Journal of NIH Research*, Apr., 9: 36–42.
Hough, et al., 1987, Purification of Two High Molecular Weight Proteases from Rabbit Reticulocyte Lysate, *The Journal of Biological Chemistry*, 262: 8303–8313.
Jeffers, et al., 1997, Degradation of the Met Tyrosine Kinase Receptor by the Ubiquitin–Proteasome Pathway, *Molecular and Cellular Biology*, 17: 799–808.
Kopp and Ghosh, 1994, Inhibition of NF–kB by Sodium Salicylate and Aspirin, *Science*, 265: 956–959.

(List continued on next page.)

*Primary Examiner*—Patrick J. Nolan
(74) *Attorney, Agent, or Firm*—Kathleen M. Williams; Palmer & Dodge, LLP

(57) ABSTRACT

The invention provides a method of detecting autoimmune disease in a mammal, comprising providing a biological sample from a mammal and detecting proteasome activity, wherein a reduction in proteasome activity from a basal state is indicative of autoimmune disease. In addition, the invention encompasses a method of treating an autoimmune disease in a mammal, comprising administering to a mammal suspected of suffering from an autoimmune disease an agent which restores NFκB activity in an amount and for a time sufficient to result in normal NFκB activity in the mammal.

4 Claims, 19 Drawing Sheets

OTHER PUBLICATIONS

Kwon, et al., 1995, Interleukin–1B–Induced NitricOxide Synthase Expression by Rat Pancreatic B–Cells: Evidence for the Involvement of Nuclear Factor kB in the Signaling Mechanism, *Endocrinology*, 136: 4790–4795.

McGuire, et al., 1988, An enzyme related to the high molecular weight multicatalytic proteinase, macroain, participates in a ubiquitin–mediated, ATP–stimulated proteolytic pathway in soluble extracts of BHK 21/C13 fibroblasts, *Biochimica et Biophysica Acta*, 967: 195–203.

Nocker, et al., 1996, The Multiubiquitin–Chain–Binding Protein Mcb1 Is a Component of the 26S Proteasome in *Saccharomyces cerevisiae* and Plays a Nonessential, Substrate–Specific Role in Protein Turnover, *Molecular and Cellular Biology*, 16: 6020–6028.

Orlowski, 1990, The Multicatalytic Proteinase Complex, a Major Extralysosomal Proteolytic System, *Biochemistry*, 29: 10289–10297.

Rechsteiner et al., 1987, Ubiquitin–Mediated Pathways for Intracellular Proteolysis, *Ann. Rev. Cell Biol.*, 3: 1–30.

Rivett, 1989, The Multicatalytic Proteinase of Mammalian Cells, *Archives of Biochemistry and Biophysics*, 268(1): 1–8.

Rivett, 1989, The Multicatalytic Proteinase, *The Journal of Biological Chemistry*, 264: 12215–12219.

Speiser, et al., 1982, Loss of ATP–dependent Proteolysis with Maturation of Reticulocytes and Erythrocytes, *The Journal of Biological Chemistry*, 257: 14122–14127.

Tanaka, et al., 1992, Proteasomes: protein and gene structures, *New Biol.*, 4(3): 173–187.

Townsley, 1997, Dominant–negative cyclin–selective ubiquitin carrier protein E2–C/UbcH10 blocks cells in metaphase, *Proc. Natl. Acad. Sci. U.S.A.*, 94: 2362–2367.

Waxman, et al., 1987, Demonstration of Two Distinct High Molecular Weight Proteases in Rabbit Reticulocytes, One of Which Degrades Ubiquitin Conjugates, *The Journal of Biological Chemistry*, 262: 2451–2457.

* cited by examiner

METHODS FOR DIAGNOSING AND TREATING AUTOIMMUNE DISEASE

FIELD OF THE INVENTION

The invention relates in general to the diagnosis and treatment of immune disorders.

BACKGROUND OF THE INVENTION

Proteolysis in the Cell

A. The Proteasome

In the cytosol, there is a soluble proteolytic pathway that requires ATP and involves covalent conjugation of the cellular proteins with the small polypeptide ubiquitin, or Ub, (Hershko et al., 1992, Ann. Rev. Biochem., 61: 761–807; Rechsteiner et al., 1987, Ann. Rev. Cell. Biol., 3: 1–30). Thereafter, the conjugated proteins are hydrolyzed by a 26S proteolytic complex containing a 20S degradative particle called the proteasome (Goldberg, 1992, Eur. J. Biochem., 203: 9–23); Goldberg et al., 1992, Nature, 357: 375–379). This multicomponent system is known to catalyze the selective degradation of highly abnormal proteins and short-lived regulatory proteins. However, the system also appears to be responsible for the breakdown of most proteins in maturing reticulocytes (Boches et al., 1982, Science, 215: 978–980); Spenser et al., 1985, J. Biol. Chem., 257: 14122–14127), in growing fibroblasts (Ciechanover et al., 1984, Cell, 37: 57–66; Gronostajski et al., 1985, J. Biol. Chem., 260: 3344–3349) and in atrophying skeletal muscle.

The first step in degradation of many proteins involves their conjugation to Ub by an ATP-requiring process, as described below. The ubiquitinated proteins are then degraded by an ATP-dependent proteolytic complex, referred to above, known as the 26S proteasome complex.

The precise nature of the 26S proteasome complex is unclear, although it has been shown that the 1000–1500 kDa (26S) complex can be formed in extracts of energy-depleted reticulocytes by an ATP-dependent association of three components, referred to as CF-1, CF-2, and CF-3 (Ganoth et al., 1988, J. Biol. Chem., 263: 12412–12419). A large (~700 kDa) multimeric protease found in the cytoplasm and nucleus of eukaryotic cells, referred to as the proteasome, is a component (CF-3) (Driscoll et al., 1992, J. Biol. Chem., 265: 4789–4792; Eytan et al., 1989, Proc. Natl. Acad. Sci. U.S.A., 86: 7751–7755; Orlowski et al., 1990, Biochemistry, 29: 10289–10297; Rivet, 1989, Arch. Biochem. Biophys., 268: 1–8).

The proteasome is believed to make up the catalytic core of the large 26S multisubunit cytoplasmic particle necessary for the ubiquitin-dependent pathway of intracellular proteolysis (Driscoll et al., 1990, J. Biol. Chem., 265: 4789–4692; Eytan et al., 1989, Proc. Natl. Acad. Sci. U.S.A., 86: 7751–7755; Hough et al., 1987, Biochemistry, 262: 8303–8313; McGuire et al., 1988, Biochim. Biophys. Acta., 967: 195–203; Rechsteiner et al., 1987, Ann. Rev. Cell. Biol., 3: 1–30; Waxman et al., 1987, J. Biol. Chem., 262: 2451–2457). By itself, the proteasome is unable to degrade ubiquitinated proteins, but provides most of the proteolytic activity of the 26S proteasome complex.

There is another ATP-dependent protease that is involved in degradation of ubiquitinated proteins, forms a complex with the proteasome and appears to be part of the 26S proteasome complex, which rapidly degrades proteins conjugated to ubiquitin. This protease, referred to as multipain, has been identified in muscle and plays an essential role in the ATP/ubiquity-independent pathway.

The complex formed between multipain and proteasome in vitro appears very similar or identical to the 1500 kDa Ub-conjugate, degrading enzyme, or 26S proteolytic complex, isolated from reticulocytes and muscle. The complexes contain the characteristic 20–30 kDa proteasome subunits, plus a number of larger subunits, including the six large polypeptides found in multipain. The complex formed contains at least 10–12 polypeptides of 40–150 kDa. A 40 kDa polypeptide regulator of the proteasome, which inhibits the proteasome's proteolytic activities has been purified from reticulocytes and shown to be an ATP-binding protein whose release appears to activate proteolysis. The isolated regulator exists as a 250 kDa multimer and is quite labile (at 42° C.). It can be stabilized by the addition of ATP or a nonhydrolyzable ATP analog, although the purified regulator does not require ATP to inhibit proteasome function and lacks ATPase activity. The regulator has been shown to correspond to an essential component of the 1500 kDa proteolytic complex. The regulator appears identical to CF-2 by many criteria. These findings suggest that the regulator plays a role in the ATP-dependent mechanism of the 26S proteasome complex.

The 20S proteasome is composed of about 15 distinct 20–30 kDa subunits. It contains at least three different peptidases that cleave specifically an the carboxyl side of the hydrophobic, basic, and acidic amino acids (Goldberg et al., 1992, Nature, 357: 375–379: Goldberg, 1992, Eur. J. Biochem., 203: 9–23; Orlowski, 1990, Biochemistry, 29: 10289–10297; Rivett et al., 1989, Arch. Biochem. Biophys., 218: 1; Rivett et al., 1989, J. Biol. Chem., 264: 12215–12219; Tanaka et al., 1992, New Biol. 4: 1–11). These peptidases are referred to as the chymotrypsin-like peptidase, the trypsin-like peptidase, and the peptidyl-glutamyl peptidase. Which subunits are responsible for these activities is unknown although the cDNA's encoding several subunits have been cloned (Tanaka et al., 1992, New Biol., 4: 1–11).

B. Ubiquitination and Phosphorylation in Protein Processing

As reviewed by Hopkin (1997, J. NIH Research, 9: 36–42) and briefly summarized herein, insight into the mechanisms by which proteolysis is controlled come from studies of the eukaryotic cell cycle. To proceed through the cell cycle, replicating its genome and dividing the resulting DNA between daughter cells during mitosis, a cell must appropriately activate and inactivate the regulators of cell division, the cyclin-dependent kinases (Cdks). To control Cdks, cells can specifically degrade the cyclin proteins that activate Cdks and the inhibitors that inactivate them. One mechanism by which specificity in targeted proteolysis is achieved is ubiquitination, the process by which cells tack long chains of a 76-amino acid marker protein called ubiquitin (Ub) onto proteins that are destined for destruction. Ubiquitination of a handful of cyclins and Cdk inhibitors leads to their timely demise and allows a cell to complete mitosis or to replicate its DNA; further, it is believed that phosphorylation of unstable proteins, such as the cyclins, often increases their susceptibility to ubiquitination and subsequent elimination.

As described below, ubiquitination affects signal transduction, as it may mark certain cell-surface growth-factor receptors for endocytosis and destruction; further, it is known that ubiquitination, coupled with phosphorylation, stimulates the signaling pathway that activates the transcription factor NFκB. Ubiquitin also plays a role in protein degradation pathways regulating cell differentiation and death during development.

i. Ubiquitination and the Cell Cycle

Evidence that ubiquitination was interesting from the point of view of regulation came with the development of a mouse cell line that arrests in the $G^2$, or gap 2, phase of the cell cycle; these cells harbor a defect that cripples an enzyme that activates Ub before it can bind to proteins, such as the cyclins, that must be targeted for destruction. Prior to this work, ubiquitination was viewed only as a means for eliminating damaged, denatured, and misfolded proteins.

Most of the proteolysis that occurs in cells involves the degradation of Ub-conjugated proteins. As stated above, the proteasome recognizes the polyubiquitin tag, selectively admits proteins to which this marker is complexed and then cleaves them into small peptide fragments. Ubiquitination is dependent upon a series of proteins named for their order of elution from a Ub-affinity column. Ub-activating enzymes, called E1s, prime Ub for transfer to a substrate protein by forming a temporary thioester linkage between a terminal glycine of Ub and one of their own cysteine residues. Enter the Ub-conjugating proteins generically called E2s. These enzymes accept activated Ub from an E1 and transfer it to the substrate protein, either directly or with the help of a Ub-ligase protein, or E3; interactions between different E2s and E3s may contribute to the substrate specificity of the ubiquitination reaction. Yeast maintain a cadre of more than a dozen structurally related E2s as well as a handful of E3s (reviewed by Haas and Siepmann, 1997, *FASEB J.*, 11: 1257–1268). Functional homologues of these proteins have been found in humans (see Honda et al., 1997, *FEBS Lett.*, 420: 25–27).

Even within the cell cycle, different sets of E2s and E3s function to mark cyclins and Cdk inhibitors for destruction. Together these proteins regulate entry into new cycles of cell division, initiation of DNA replication, and the onset of mitosis. In yeast, cyclins bind to and activate Cdc28, which then pushes cells into the next phase of the cell cycle, initiating cell division. It is said that the concentrations of both the cyclins and the Cdk inhibitors that drive the cell cycle through their interactions with Cdc28 may be tightly controlled by Ub-associated proteolysis. The G1 cyclins Cln1, Cln2, and Cln3 activate Cdc28, by which they are then reciprocally phosphorylated; this phosphorylation marks the cyclins for ubiquitination and subsequent destruction by the proteasome.

The Ub-ligase complex that ubiquitinates the cell-cycle proteins that control the completion of mitosis is known to be activated by phosphorylation. The coupling of cyclin B and its kinase Cdc2 initiates mitosis in yeast. In that system, cyclin B accumulates during interphase until its pairing with Cdc2 drives the cell into mitosis and leads to its eventual destruction. The cyclosome (also called the anaphase-promoting complex, or APC), a 20S nuclear particle which serves as the Ub-ligase complex, helps to ubiquitinate the mitotic cyclins A and B as well as the as-yet-unidentified "glue" proteins that bind sister chromatids together during metaphase. Late in mitosis, an unknown kinase phosphorylates and activates the cyclosome/APC. Then, working in conjunction with a Ub-conjugating enzyme called E2-C in clams (an organism favored by cell-cycle researchers), the cyclosome marks the mitotic cyclins for degradation by the proteasome (Aristarkhov et al., 1996, *Proc. Natl. Acad. Sci. U.S.A.*, 93: 9303–9307); Ub-directed destruction of the mitotic cyclins leads to the inactivation of Cdc2 and the degradation of the 'glue" proteins, so that sister chromatids are allowed to segregate into the two daughter cells. E2-C and its human homologue, the ubiquitin-conjugating human enzyme UbcH10, have been characterized in detail (Townsley et al., 1997, *Proc. Natl. Acad. Sci. U.S.A.*, 94: 2362–2367).

ii. Cell Signalling Pathways

Proteins that control cell-cycle progression may respond to environmental cues, such as are provided by growth factors. Growth factor-stimulated signaling pathways are, themselves controlled in part by ubiquitination. One of the best studied examples is the NFκB pathway (see below). Binding of the cytokine tumor necrosis factor-α (TNF-α) to cell-surface receptors, or the occurrence of another proinflammatory or stress event (e.g. hypoxia), initiates a signaling cascade that activates NFκB (see below) and c-Jun, transcription factors that govern the proliferative response in cells.

Ubiquination may be involved in regulating the amount of a receptor present on the cell membrane. Stimulation of the Met tyrosine-kinase receptor by the ligand hepatocyte growth factor/scatter factor (HGF/SFD) spurs the embryonic development of a variety of mammalian tissues, including liver, placenta, and muscles). For example, it has been reported that HGF/SF stimulates the degradation of the Met tyrosine-kinase receptor by proteasomes in a human sarcoma cell line (Jeffers et al., 1997, *Mol. Cell. Biol.*, 17: 799–808). In the absence of HGF/SF, this receptor is cleaved by an unknown protease and the fragment containing the tyrosine-kinase activity remains embedded in the cell membrane. According to Hopkin et al. (1997, supra), it has been postulated that the presence of an unregulated tyrosine kinase in the membrane could be dangerous and that Ub-targeted degradation is intended to rid the cell of the membrane-embedded kinase fragment before damage can occur.

It is thought that the proteasome will cleave any ubiquitinated protein with which it comes in contact; however, different receptors may recognize substrates bearing Ub chains that differ in internal. The 2-megadalton proteasome complex, which comprises four stacked rings of α and β protein subunits with a series of protease-active sites lining the inside of the resulting tube, recognizes a subset of ubiquitin chains via the S5 protein subunit. After a Ub-tagged protein binds to the proteasome complex, it is unfolded in order to facilitate passage through the proteasome pore into the proteolytic chamber. Mutational inactivation of the S5 proteasome subunit results in a specific subset of ubiquitinated proteins being spared from degradation (van Nocker et al., 1996, *Mol. Cell. Biol.*, 16: 6020–6028). It is this selectivity which suggests that the proteasome may possess more than one receptor for detecting Ub-conjugated proteins.

NFκB has been implicated in the etiology of immune disorders. Adams et al. (WO 96/13266) teach inhibition of proteasome activity, which mediates the activation of NFκB, to treat autoimmune diseases.

Similarly, Brand et al. (WO 95/24914) teach that new, as well as existing, proteasome inhibitors may be used to treat autoimmune diseases.

Further, according to Palombella et al. (WO 95/25533; page 7, lines 16–23), Goldberg et al. are said to teach methods and drugs that inhibit antigen processing for the treatment of autoimmune diseases.

According to Kopp and Ghosh (1994, *Science*, 265: 956–969) and Grilli et al. (1996, *Science*, 274: 1383–1385), salicylate and glucocorticoids, anti-inflammatory drugs that are inhibitors of NFκB, are widely used to treat established cases of autoimmune diseases.

In addition, NFκB is said to said to be a positive transcriptional regulator of inducible nitric oxide synthase (iNOS), which in turn mediates cytokine-induced inhibition of insulin secretion by pancreatic cells of the islets of Langerhans (Kwon et al., 1995, *Endocrinology*, 136: 4790–4795); inhibition of NFκB activity suppresses this phenotype.

There is need in the art for improved methods of treating autoimmune disorders.

SUMMARY OF THE INVENTION

The invention provides a method of detecting autoimmune disease in a mammal, comprising providing a biological sample from a mammal and detecting proteasome activity, wherein a reduction in proteasome activity from a basal state is indicative of autoimmune disease.

As used herein, the term "autoimmune disease" refers to a disorder wherein the immune system of a mammal mounts a humoral or cellular immune response to the mammal's own tissue or has intrinsic abnormalities in its tissues preventing proper cell survival without inflammation.

Examples of autoimmune diseases include, but are not limited to, diabetes, rheumatoid arthritis, multiple sclerosis, lupus erythematosis, myasthenia gravis, scleroderma, Crohn's disease, ulcerative colitis, Hashimoto's disease, Graves' disease, Sjögren's syndrome, polyendocrine failure, vitiligo, peripheral neuropathy, graft-versus-host disease, autoimmune polyglandular syndrome type I, acute glomerulonephritis, Addison's disease, adult-onset idiopathic hypoparathyroidism (AOIH), alopecia totalis, amyotrophic lateral sclerosis, ankylosing spondylitis, autoimmune aplastic anemia, autoimmune hemolytic anemia, Behcet's disease, Celiac disease, chronic active hepatitis, CREST syndrome, dermatomyositis, dilated cardiomyopathy, eosinophilia-myalgia syndrome, epidermolisis bullosa acquisita (EBA), giant cell arteritis, Goodpasture's syndrome, Guillain-Barré syndrome, hemochromatosis, Henoch-Schönlein purpura, idiopathic IgA nephropathy, insulin-dependent diabetes mellitus (IDDM), juvenile rheumatoid arthritis, Lambert-Eaton syndrome, linear IgA dermatosis, myocarditis, narcolepsy, necrotizing vasculitis, neonatal lupus syndrome (NLE), nephrotic syndrome, pemphigoid, pemphigus, polymyositis, primary sclerosing cholangitis, psoriasis, rapidly-progressive glomerulonephritis (RPGN), Reiter's syndrome, stiff-man syndrome and thyroiditis.

As used herein, the term "diabetes" refers both to the type I form of the disease and to type II cases that share only an islet cell defect with type I.

Symptoms common to many types of autoimmune dysfunction include, but are not limited to: fatigue; inflammation; paresis; joint stiffness, pain or swelling; skin lesions or nodules; skin discoloration; enzymatic imbalances; tissue degeneration. Examples of such symptoms as pertain to specific autoimmune diseases are described hereinbelow in the Description section. Such symptoms or, alternatively, measurements of tissue death/destruction, may be used either as diagnostic indicators of the presence of an autoimmune disease, or as indices by which to assess the efficacy of treatment thereof.

In the treatment of autoimmune disease, a therapeutically effective dosage regimen should be used. By "therapeutically effective", one refers to a treatment regimen sufficient to restore the the mammal to the basal state, as defined herein, at the cellular or tissue site of manifestation or to prevent an autoimmune disease in an individual at risk thereof or restore the mammal's immune system to the basal state. Alternatively, a "therapeutically effective regimen" may be sufficient to arrest or otherwise ameliorate symptoms of an autoimmune disease. Generally, in the treatment of autoimmune diseases, an effective dosage regimen requires providing the medication over a period of time to achieve noticeable therapeutic effects; such a period of time may begin at, or even before, birth and continue throughout the life of the individual being treated. Methods of treatment are discussed in detail in the Description section, below.

As used herein, the term "biological sample" refers to a whole organism or a subset of its tissues, cells or component parts (e.g. body fluids, including but not limited to blood, mucus, lymphatic fluid, synovial fluid, cerebrospinal fluid, saliva, amniotic fluid, amniotic cord blood, urine, vaginal fluid and semen). "Biological sample" further refers to a homogenate, lysate or extract prepared from a whole organism or a subset of its tissues, cells or component parts, or a fraction or portion thereof. Lastly, "biological sample" refers to a medium, such as a nutrient broth or gel in which an organism has been propagated, which contains cellular components, such as proteins or nucleic acid molecules.

As used herein, the term "organism" refers to all cellular life-forms, such as prokaryotes and eukaryotes, as well as non-cellular, nucleic acid-containing entities, such as bacteriophage and viruses.

As used herein, the term "mammal" refers to a member of the class Mammalia, including a human.

It is contemplated that procedures useful for the detection of proteins or nucleic acids and biological activities thereof include, but are not limited to, immunological assays, such as immunoblotting, immocytochemistry, immunohistochemistry or antibody-affinity chromatography, electrophoretic analysis, such as one- or two-dimensional SDS-PAGE, Northern or Southern analysis, in vivo or in vitro enzymatic activity assay, the polymerase chain reaction (PCR), reverse-transcription PCR (RT-PCR), in situ nucleic acid hybridization, electrophoretic mobility shift analysis (EMSA), transcription assay, or variations or combinations of these or other techniques such as are known in the art.

As used herein, the term "proteasome" refers to a multi-subunit protein complex in the cytoplasm of eukaryotic cells which recognizes and selectively cleaves ubiquitinated protein molecules to mediate either activation or degradation of the protein so recognized and cleaved.

As used herein in reference to proteasome activity, the term "reduction" refers to the failure of the proteasome to cleave a target ubiquitinated protein at as few as one-, more than one-, or even as many as all of the sites that it normally (i.e., in a genetically wild-type or otherwise healthy individual) recognizes and cleaves in that protein. Preferably, such a reduction involves failure to cleave the target protein at 5–10% of sites, more preferably, at 20–50% of sites, and most preferably at 75–100% of such sites. Different numbers and/or patterns of sites on different proteins are cleaved by the proteasome. The term "different proteins" refers to protein molecules that differ in amino acid sequence in at least one position. Promiscuous cleavage (i.e., at a site not normally recognized and cleaved) of a protein by the proteasome is defined as a reduction only if such aberrant cleavage is accompanied by the failure of the proteasome to cleave a site normally recognized and cleaved.

As used herein, the term "basal state" refers to the level of activity of a protein, nucleic acid or other molecule where autoimmune disease is not present, i.e. a "normal level" of activity. The basal state is observed in genetically wild-type or otherwise healthy individuals, as well as in individuals who have a propensity for an autoimmune disease (as judged by genetic or environmental criteria known to those of skill in the medical art) but have not yet developed such a disease and even individuals who are in the early stages of an autoimmune disease but have not, for example, become actively symptomatic.

Preferably, the biological sample comprises protein.

It is contemplated that the protein of a biological sample of use in the invention may be crude (i.e., in an unfractionated cell lysate), partially-purified or isolated, and either naturally-occurring or produced by recombinant techniques, such as the expression of a cDNA or other gene sequence cloned from a mammal.

In a preferred embodiment, a reduction in proteasome activity is detected.

A reduction in proteasome activity may be observed as a reduction in the activation of transcription factors (among them, NFκB) as judged either by observation of the physical properties of such a protein (for example, antigenicity or molecular weight, as judged by sedimentation or electrophoretic mobility) that are characteristic of its pre-activation form or by the absence of mRNA (or the protein encoded by such a message) resulting from the transcription of a gene that is positively regulated by the protein in a biological sample. In addition, a reduction in the proteolytic processing of a protein normally cleaved by the proteasome (such as an MHC antigen, which is cleaved by the proteasome prior to transport to-and presentation on the cell surface).

Preferably, the reduction in proteasome activity comprises a reduction of proteolytic processing of NFκB or a subunit thereof.

Methods for the detection of a reduction in proteolytic processing of NFκB are as described in detail hereinbelow in Example 2.

Preferably, the mammal is a human.

It is preferred that the autoimmune disease is an HLA class II-linked disease.

As used herein, the term "HLA class II-disease" refers to those autoimune diseases showing statistical risk factors for disease penetrance attributed to HLA class II genes or to neighboring genes.

The term "HLA" (for "human lymphocyte antigen") refers to genes of the human major histocompatibility complex (MHC) or their protein products. In mice, the genetic region corresponding to- or homologous with the HLA is termed the H2 complex.

In another preferred embodiment, the autoimmune disease is selected from the group that includes those diseases listed above as autoimmune diseases.

Another aspect of the present invention is a method of detecting autoimmune disease in a mammal, comprising providing a biological sample from a mammal and detecting protein ubiquitination, wherein a reduction in protein ubiquitination from a basal state is indicative of autoimmune disease.

As used herein in reference to protein ubiquitination, the term "reduction" refers to the failure of ubiquitinating enzymes to ubiquitinate a target protein at as few as one-, more than one-, or even as many as all of the sites that they normally (i.e., in a genetically wild-type or otherwise healthy individual) recognize and ubiquitinate in that protein. Preferably, such a reduction involves failure to ubiquitinate the target protein at 10–20% of sites, more preferably, at 40–50% of sites, and most preferably at 80–100% of sites. Different numbers and/or patterns of sites on different proteins are ubiquitinated by the ubiquitinating enzymes. The term "different proteins" refers to protein molecules that differ in amino acid sequence in at least one position. Promiscuous ubiquitination (i.e., at a site not normally recognized and ubiquitinated) of a protein by the ubiquitinating enzymes is defined as a reduction only if such aberrant ubiquitination is accompanied by the failure of the ubiquitinating enzymes to ubiquitinate a site normally recognized and ubiquitinated.

It is preferred that the biological sample comprises protein.

It is additionally preferred that a reduction in protein ubiquitination is detected for a protein.

Preferably, the mammal is a human.

It is preferred that the autoimmune disease is an HLA class II-linked disease.

In another preferred embodiment, the autoimmune disease is selected from the group that includes those diseases listed above.

The invention also encompasses a method of detecting autoimmune disease in a mammal, comprising providing a biological sample from a mammal and detecting protein phosphorylation, wherein a reduction in protein phosphorylation from a basal state is indicative of autoimmune disease.

As used herein in reference to protein phosphorylation, the term "reduction" refers to the failure of a protein kinase to phosphorylate a target protein at as few as one-, more than one-, or even as many as all of the sites that it normally (i.e., in a genetically wild-type or otherwise healthy individual) recognizes and phosphorylates in that protein. Preferably, such a reduction involves failure to phosphorylate the target protein at 2–10% of sites, more preferably, at 25–50% of sites, and most preferably at 90–100% of sites. Different numbers and/or patterns of sites on different proteins are phosphorylated by protein kinases. The term "different proteins" refers to protein molecules that differ in amino acid sequence in at least one position. Promiscuous phosphorylation (i.e., at a site not normally recognized and phosphorylated) of a protein by a protein kinase is defined as a reduction only if such aberrant phosphorylation is accompanied by the failure of the protein kinase to phosphorylate a site normally recognized and phosphorylated.

It is preferred that the biological sample comprises protein.

It is also preferred that a reduction in protein phosphorylation is detected.

Preferably, the mammal is a human.

It is preferred that the autoimmune disease is an HLA class II-linked disease.

In another preferred embodiment, the autoimmune disease is selected from the group provided above.

Another aspect of the present invention is a method of detecting autoimmune disease in a mammal, comprising providing a biological sample from a mammal and detecting NFκB activity, wherein a reduction in NFκB activity from a basal state is indicative of autoimmune disease.

As defined herein with regard to NFκB activity, the term "reduction" refers to a loss of the ability of NFκB to direct the transcription of genes whose cis-regulatory sequences comprise an NFκB recognition site, wherein such a site is normally bound and transcription of the gene activated by NFκB. Preferably, such a reduction is in the range of 5–10% of the basal state level of activity, more preferably 25–50% and most preferably 70–100%.

Preferably, the biological sample comprises protein.

It is preferred that the biological sample comprises a nucleic acid.

As used herein, the term "nucleic acid" refers to a DNA molecule, such as genomic DNA or cDNA, and also to RNA. A nucleic acid may be double- or single-stranded, circular or linear and may be naturally-occurring, recombinant or synthetic (produced by either enzymatic or chemical means as a known in the art); if recombinant or synthetic, a nucleic acid molecule may comprise sequences which are known to occur naturally or which are novel.

It is preferred that a reduction in said NFκB activity is detected.

As stated above, a reduction in in NFκB activity may be determined either through its failure to direct the transcription of downstream genes, physical characteristics or DNA- or protein-binding activity in comparison to those of the basal state. NFκB activity may be assayed either in vivo or in vitro using an NFκB-dependent reporter gene expression construct and a substrate for enzymatic detection (such as chloramphenicol acetyl transferase or β-galactosidase, depending on the specificity of the enzyme encoded by the reporter gene), wherein comparative quantitation of the product of the diagnostic enzymatic reaction (or, in the absence of a reaction substrate, the level of the reporter mRNA or its encoded protein) in biological samples derived from a test subject and a normal control indivicual allow for the assessment of NFκB functional loss. Alternatively, immunological or other biochemical determination of whether or not IκB has been cleaved from NFκB may be made, as described above and in Example 2, below.

Preferably, the mammal is human.

It is preferred that the autoimmune disease is an HLA class II-linked disease.

In another preferred embodiment, the autoimmune disease is selected from the group that includes those diseases listed above.

The invention also provides a method of detecting autoimmune disease in a mammal, comprising providing a biological sample from a mammal and detecting cell survival or growth, wherein cell death prior to direct lymphocyte or antibody attack in a tissue that is a suspected target of an autoimmune disease is indicative of the autoimmune disease.

As used herein, the term "growth" refers to mitosis or differentiation (acquisition of cell surface marders or specialized functions, e.g. protein production, indicative of a mature cell type.

As used herein, the term "tissue" refers to intact tissue or tissue fragments, such that the cells are sufficiently aggregated (associated) so as to form a cohesive mass. A tissue may comprise an entire organ (e.g. the pancreas, the thyroid, a muscle, or others) or other system (e.g. the lymphatic system) or a subset of the cells thereof; therefore, a tissue may comprise 0.1–10%, 20–50% or 50–100% of the organ or system (e.g. as is true of islets of the pancreas).

Examples of tissue types that are the targets of autoimmune disease include, but are not limited to, blood, lymph, the central nervous system (including brain or spinal cord gray or white matter), liver, kidney, spleen, heart muscle or blood vessels, cartilage, ligaments, tendons, lung, pancreas (in particular, pancreatic islets of Langerhans), lacrimal ducts, melanocytes, the adrenal cortex, skin, the intestinal tract (in particular, the luminal epithelium and the colon), ovary, testes, prostate, and regions such as joints, nerve/blood vessel junctions, salivary glands, bones, specific tendons or ligaments.

As used herein, the term "cells" is defined as including dissociated cells, intact tissue or tissue fragments.

As used herein, the term "suspected target" refers to a tissue that is damaged in the course of an autoimmune disease of which a mammal is believed to suffer or to be at risk of suffering.

It is contemplated that an individual is at risk of an autoimmune disease based either upon family history, the results of genetic testing, exposure (either after birth or in utero) to a substance such as is known to trigger autoimmune disease (see, below, the description of animal models of autoimmune disease); such an individual is "suspected of suffering" (see below) or "suspected of harboring" an autoimmune disease or is said to have a "propensity" for developing such a disease.

Preferably, the sample is obtained from the mammal at an early stage in the disease prior to or early in the formation of autoantibodies against the tissue.

As used herein, the term "prior" may refer to a period of time immediately before autoantibodies first are or would expected to be formed in an individual with a propensity for autoimmune disease. "Prior" may be used to indicate a time weeks, months or years before the appearance of autoantibodies. It is contemplated that in an individual suspected of being at risk for an autoimmune disease, this may be as early as birth or even during the prenatal period.

As used herein, the term "early" refers to a stage of an autoimmune disease preceding complete target tissue destruction by the immune system.

Preferably, cell death is detected in a tissue that is a suspected target of autoimmune disease prior to the formation of autoantibodies.

It is preferred that the biological sample comprises cells of a tissue that is a suspected target of autoimmune disease.

It is additionally preferred that the mammal is a human.

Preferably, the autoimmune disease is an HLA class II-linked disease.

In another preferred embodiment, the autoimmune disease is selected from the group that includes those diseases listed above.

The invention also encompasses a method of treating an autoimmune disease in a mammal, comprising administering to a mammal suspected of suffering from an autoimmune disease an agent which restores protein ubiquitinating enzyme function in an amount and for a time sufficient to result in normal protein ubiquitination in the mammal.

As used herein, the term "agent" refers to a biochemical substance selected from the group that includes, but is not limited to, proteins, peptides or amino acids; nucleic acids such as DNA, such as full-length genes or fragments thereof derived from genomic, cDNA or artificial coding sequences, gene regulatory elements, RNA, including mRNA, tRNA, ribosomal RNA, ribozymes and antisense RNA, oligonucleotides and oligoribonucleotides, deoxyribonucleotides and ribonucleotides; carbohydrates; lipids; proteoglycans; such agents may be administered as isolated (purified) compounds or in crude mixtures, such as in a tissue, cell or cell lysate. Alternatively, "agent" may refer to an organic or inorganic chemical as is known in the art.

Methods of administering a therapeutic agent include, but are not limited to, topical application (e.g., for skin lesions), intravenous drip or injection, subcutaneous, intramuscular, intraperitoneal, intracranial and spinal injection, ingestion via the oral route, inhalation, transepithelial diffusion (such as via a drug-impregnated, adhesive patch) or by the use of an implantable, time-release drug delivery device, which may comprise a reservoir of exogenously-produced agent or may, instead, comprise cells that produce and secrete the therapeutic agent.

As used herein, the term "ubiquitinating enzyme function" refers to the covalent attachment of one or more ubiquitin molecules to a protein by members of the several classes of ubiquitinating enzymes, which include ubiquitin-activating enzymes (E1, which prime ubiquitin for attachment to a protein), ubiquitin-conjugating enzymes (E2, which bind primed ubiquitin for transfer to a target protein and ubiquitin ligases (E3, which catalyze the linkage of ubiquitin to specific sites on the target protein, which sites vary in number and type from protein to protein, as discussed above).

As used herein with regard to protein ubiquitination, the term "restore" refers to a return of the ubiquitination of at least one site which is normally ubiquitinated (that is, a site that is ubiquitinated in the basal state, as defined above) and, preferably all such sites, but is not ubiquitinated in the course of an autoimmune disease. Preferably, in the restoration of a normal level and pattern of ubiquitination, 50% of such sites are restored, more preferably, 60–85% and, most preferably, 90–100%. Such percentages include only the ubiquitination of sites that are normally ubiquitinated in the protein in question. In addition, an elevation of ubiquitination beyond 100% of normal values is not encompassed by this definition. It is contemplated that a restoration is sufficient to allow proper (i.e., that which is qualitatively comparable to that observed in the basal state) recognition and cleavage of the protein so ubiquitinated by the proteasome.

Preferably, the agent is selected from the group that consists of a protein and a nucleic acid that encodes that protein.

It is preferred that the protein is selected from the group that includes a ubiquitin-activating enzyme (E1), a ubiquitin-conjugating enzyme (E2) and ubiquitin-ligases (E3).

Examples of human homologues of the yeast ubiquitination enzymes include, but are not limited to UbcH5 (which functions as an E2) and the MDM2 oncoprotein, which acts as a ubiquitin ligase, or E3.

Preferably, the agent is a nucleic acid which encodes an antisense RNA or a ribozyme.

It is preferred that the mammal is a human.

It is additionally preferred that the autoimmune disease is an HLA class II-linked disease.

In another preferred embodiment, the autoimmune disease is selected from the group that includes those diseases listed above.

Another aspect of the present invention is a method of treating an autoimmune disease in a mammal, comprising administering to a mammal suspected of suffering from an autoimmune disease an agent which restores NFκB activity in an amount and for a time sufficient to result in normal NFκB activity in the mammal.

As used herein, the term "normal NFκB activity" refers to a value that is at least 25% of the activity of one or more of NFκB and its subunits p50, p105 and p65 observed in the basal state, as defined herein above, preferably in the range of 30–90% and most preferably in the range of 95–100%. "Normal NFκB activity" may not exceed 100% of NFκB basal state activity.

Preferably, the agent is selected from the group that consists of a protein and a nucleic acid that encodes that protein.

It is preferred that the protein is selected from the group that includes a mutant- or wild-type NFκB p50, a mutant- or wild-type NFκB p65, tumor necrosis factor-α, E-selectin, I-cam, and V-cam, interleukin-2, interleukin-6, granulocyte colony-stimulating factor, interferon-β, Lmp2, Lmp7, a ubiquitin-activating enzyme (E1), a ubiquitin-conjugating enzyme (E2), a ubiquitin-ligase (E3), a ubiquitin deconjugating enzyme (UCH), a protein kinase, a proteasome subunit and an antibody directed against one of the 240 kD and 200 kD human erythrocyte proteasome inhibitors, CF-2 and IκB.

In another preferred embodiment, the agent is selected from the group that consists of a ribozyme, an antisense RNA molecule, a DNA molecule that encodes a said ribozyme, and a DNA molecule that encodes a said antisense RNA molecule.

Preferably, the ribozyme or antisense RNA molecule is directed against one of the 240 kD and 200 kD human erythrocyte proteasome inhibitors, CF-2 and IκB.

It is preferred that the mammal is a human.

It is additionally preferred that the autoimmune disease is an HLA class II-linked disease.

In another preferred embodiment, the autoimmune disease is selected from the group that includes those diseases listed above.

Another aspect of the present invention is a method of treating an autoimmune disease in a mammal, comprising administering to a mammal suspected of suffering from an autoimmune disease resulting from a reduction in the activity of NFκB, DNA repair factor TFIIH, STAT transcription factor, ubiquitination, phosphorylation or the proteasome an agent which restores lymphocyte maturation in an amount and for a time sufficient to result in normal lymphocyte maturation in the mammal.

It is preferred that the agent is selected from the group that consists of a protein and a nucleic acid that encodes that protein.

It is additionally preferred that the protein is selected from the group that includes apolipoprotein B100, DNA repair factor TFIIH, STAT transcription factor, a mutant- or wild-type NFκB p50, a mutant- or wild-type NFκB p65, tumor necrosis factor-α, E-selectin, I-cam, and V-cam, interleukin-2, interleukin-6, a ubiquitin deconjugating enzyme (UCH), colony-stimulating factor, interferon-β, Lmp2, Lmp7, a ubiquitin-activating enzyme (E1), a ubiquitin-conjugating enzyme (E2), a ubiquitin-ligase (E3), a protein kinase, a proteasome subunit and an antibody directed against one of the 240 kD and 200 kD human erythrocyte proteasome inhibitors, CF-2 and IκB.

Preferably, the agent is selected from the group that includes a ribozyme, an antisense RNA molecule, a DNA molecule that encodes a ribozyme and a DNA molecule that encodes an antisense RNA molecule.

It is preferred that the ribozyme or antisense RNA molecule is directed against one of the 240 kD and 200 kD human erythrocyte proteasome inhibitors, CF-2 and IκB.

It is additionally preferred that the mammal is a human.

Preferably, the autoimmune disease is an HLA class II-linked disease.

In another preferred embodiment, the autoimmune disease is selected from the group that includes those diseases listed above.

A final aspect of the present invention is a method of treating an autoimmune disease in a mammal, comprising administering to a mammal suspected of suffering from an autoimmune disease resulting from a reduction in the activity of NFκB, DNA repair factor TFIIH, STAT transcription factor, or the proteasome an agent which restores the cell cycle in an amount and for a time sufficient to result in normal survival of cells of a tissue that is susceptible to an autoimmune disease prior to the formation of autoantibodies, prior to cell death or prior to cellular attack against the cells in the mammal.

As defined herein, "normal survival of cells" is at least a 10% cell survival rate relative to that observed in the basal state. Preferably, "normal survival of cells" is in the range of 25–50% or even 75–100%; however, "normal survival of cells" does not encompass cell survival at a rate higher than 100% of that observed in the basal state. In other words, "normal survival of cells" does not refer to hyperproliferation of cells.

Preferably, the agent is selected from the group that includes a protein and a nucleic acid that encodes that protein.

It is preferred that the protein is selected from the group that includes a cyclin, a cyclin-dependent kinase, apolipoprotein B100, DNA repair factor TFIIH, STAT transcription factor, a mutant- or wild-type NFκB p50, a mutant- or wild-type NFκB p65, tumor necrosis factor-α, E-selectin, I-cam, and V-cam, interleukin-2, interleukin-6, granulocyte colony-stimulating factor, interferon-β, Lmp2, Lmp7, a ubiquitin-activating enzyme (E1), a ubiquitin-conjugating enzyme (E2), a ubiquitin-ligase (E3), a ubiquitin deconjugating enzyme (UCH), a protein kinase, a proteasome subunit and an antibody directed against one of the 240 kD and 200 kD human erythrocyte proteasome inhibitors, CF-2 and IκB.

It is additionally preferred that the agent is selected from the group that includes a ribozyme, an antisense RNA molecule, a DNA molecule that encodes a ribozyme and a DNA molecule that encodes an antisense RNA molecule.

Preferably, the ribozyme or antisense RNA molecule is directed against one of the 240 kD and 200 kD human erythrocyte proteasome inhibitors, CF-2 and IκB.

It is preferred that the mammal is a human.

It is additionally preferred that the autoimmune disease is an HLA class II-linked disease.

In another preferred embodiment, the autoimmune disease is selected from the group that includes those diseases listed above.

BRIEF DESCRIPTIONS OF THE DRAWINGS

FIG. 1 shows the association of NFκBp65 with a cellular serine kinase. FIG. 1A: GST-NFκBp65 and GST-CTD were expressed in BL21pLysS *E. Coli* cells and purified by selective absorption to glutathionsepharose beads. GST-NF-κBp65 was incubated with cytosolic and nuclear extracts. Reaction mixtures were washed in PBS. The precipitated complexes were then incubated with GST-CTD of RNA polymerase II large subunit under the kinase buffer containing γ-[$^{32}$P]ATP as previously described (Hayashi et al., 1993, *J. Biol. Chem.*, 268: 26790–26795; Faustman et al., 1989, *Diabetes*, 38: 1462–1468). The phosphorylated products were separated on 12% SDS-PAGE and visualized by autoradiography. One-fortieth of the input (I) and supernatant (S) fractions and 1/40 of the last wash (W) and pellet (P) fractions were used for in vitro kinase reaction. FIG. 1B: In vitro kinase reactions were performed under the different conditions containing the individual indicated amount of the precipitated complexes, GST-CTD. FIG. 1C: Selective inhibition of phosphorylation activity by DRB. In vitro kinase assays were carried out and phosphorylated products were separated by SDS-PAGE and visualized by autoradiography (upper panel). Quantitation of phosphorylated GST-CTD was performed with BAS 3000 phosphoimager and were plotted out (lower panel). The indicated concentration of DRB were included in each kinase reaction mixture. FIG. 1D: Phosphoamino acid analysis of in vitro-labeled GST-CTD. GST-CTD of RNA polymerase II large subunit were phosphorylated in the in vitro kinase reaction and resolved by SDS-PAGE. The phosphorylated form of GST-CTD was excised from the gel and processed for phosphoamino acid analysis. The phosphoamino acids were separated by electrophoresis by standard methods, and the migration of the phosphoamino acid standards were visualized by ninhydrin staining, as indicated. FIG. 1E: Transactivation domain of NFκBp65 is sufficient for the association with a cellular serine kinase. Cytosolic extracts or nuclear extracts were incubated with either GST, GST-NFκBp65Q417 or GST-NFκBp65C418. Precipitated complexes were incubated with GST-CTD of RNA polymerase II large subunit in kinase buffer containing γ-[$^{32}$P] ATP. The phosphorylated products were separated on 12% SDS-PAGE and visualized by autoradiography. One-fortieth of the input (I) and supernatant (S) fractions and 1/40 of the last wash (W) and pellet (P) fractions were used for the in vitro kinase reaction.

FIG. 2 presents the detection of ATP-binding proteins that associate with NFκBp65, such as cellular serine kinases, by in vitro affinity labeling. GST-NF-κBp65 (FIG. 2A) or GST-NF-κBp65C418 (FIG. 2B) was incubated with cytosolic extract (left panel), nuclear extract (right panel). The precipitated complexes were then incubated with GST-CTD under the kinase buffer containing γ-[$^{32}$P]ATP for in vitro kinase assay. The precipitated complexes were incubated with 8-azide-α-$^{32}$P) ATP in kinase buffer for the ATP-binding assay. The samples were irradiated by a UV lamp. The phosphorylated products or ATP affinity-labeled products were separated on 12% SDS-PAGE and visualized by autoradiography. One fortieth of the input (I) and supernatant (S) fractions and 1/40 of the last wash (W) and pellet (P) fractions were used for the in vitro kinase reaction. FIG. 1C: The cytosolic extract (left panel), nuclear extract (right panel) were incubated with anti-NFκBp65 polyclonal antibody. Immunoprecipitation assays were performed and then the immunoprecipitated complexes were incubated with GST-CTD in kinase buffer containing γ-[$^{32}$P] ATP for the in vitro kinase assay. The immunoprecipitated complexes were incubated with 8-azide-α-$^{32}$P) ATP in kinase buffer for the ATP-binding assay. The samples were irradiated by a UV lamp. The phosphorylated products or ATP affinity-labeled products were separated on 12% SDS-PAGE and visualized by autoradiography. One-fortieth of the input (I) and supernatant (S) fractions and 1/40 of the last wash (W) and pellet (P) fractions were used for in vitro kinase reaction.

FIG. 3 shows the induction of kinase activity by HIV-1 trans-activator transcription factor (Tat). FIG. 3A: GST-NFκBp65 was incubated with cytosolic and nuclear extracts. The precipitated complexes were pre-incubated with either wild-type GST-Tat, or either of the mutants GST-Tat K41A and GST-Tat Cys22 at 4° C. for 5 minutes. The amount of GST-Tat added into the reaction mixtures is indicated in the figure. The reaction mixtures were then incubated with GST-CTD in kinase buffer containing γ-[$^{32}$P]ATP. The phosphorylated products were separated on 12% SDS-PAGE and visualized by autoradiography. FIG. 3B: Graphic representation of quantitation of phosphorylated GST-CTD.

FIG. 4 shows the association of NFκBp65 with Cdks. Cytosolic extracts or nuclear extracts were incubated with either GST-NFκBp65 (FIG. 4A, FIG. 4C) or GST-NFκBp65 C418 (FIG. 4B). FIGS. 4A and 4B: The protein complexes were precipitated using GST-sepharose beads after incubation and immunoblotting. FIG. 4C: The protein complexes were precipitated using anti-NFκBp65 polyclonal antibody after incubation and immunoblotting blotting with appropriate antibodies. One-fortieth of the input (I) and supernatant (S) fractions and ¹⁄₄₀ of the last wash (W) and pellet (P) fractions were used for the immunoblotting blotting assay.

FIG. 7 presents the identification of NFκB DNA-binding protein in DNA/protein complexes using super-shift assay.

FIG. 8 presents κB sequence-binding activities in spleen cells from BALB/C and NOD mice.

Figure 9A:
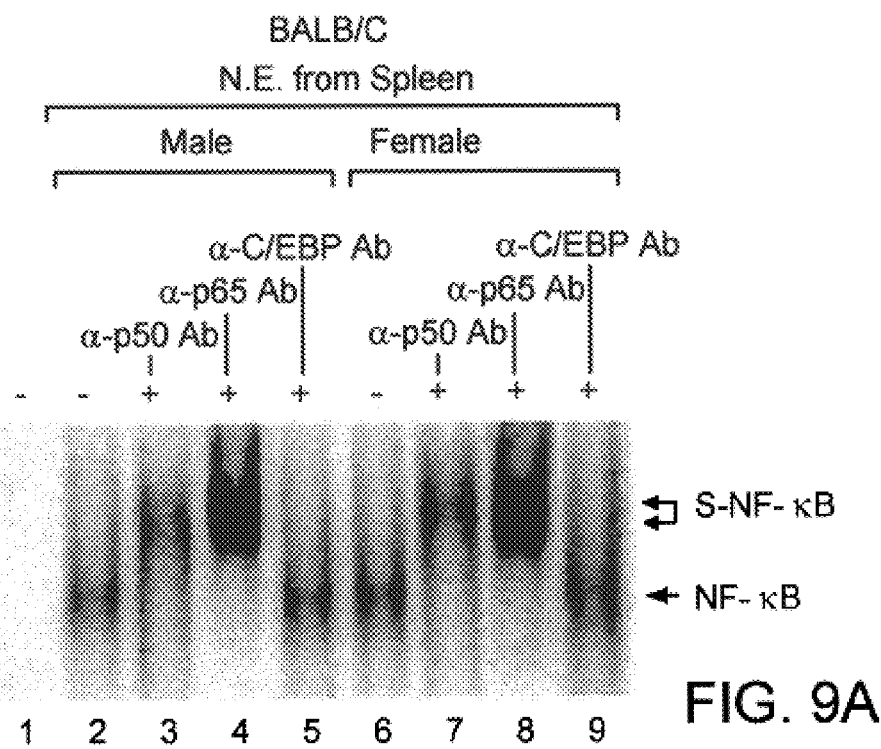
Figure 9B:
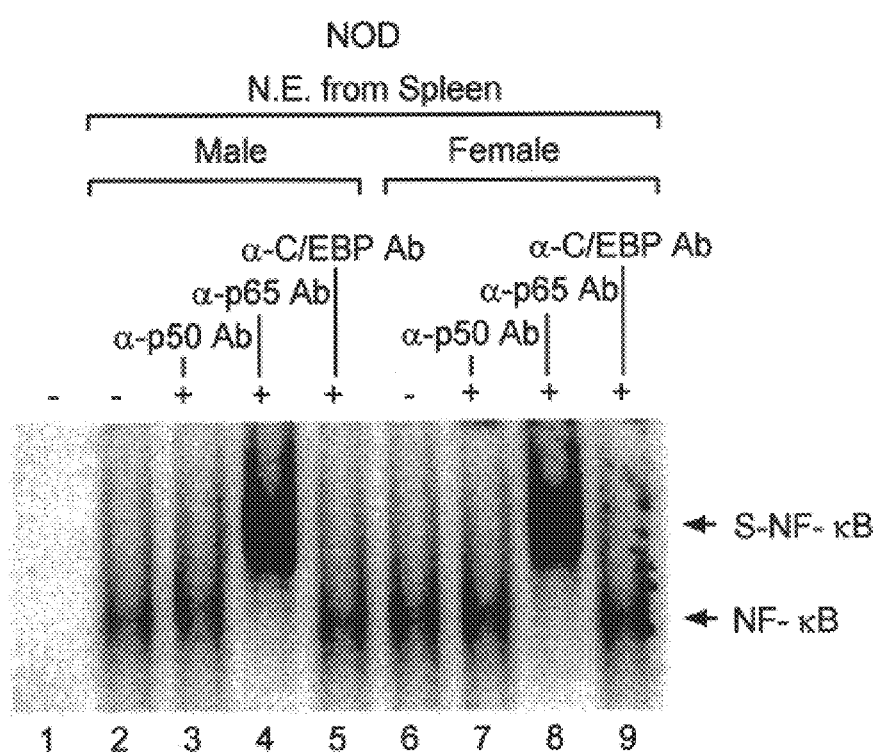

FIG. 9 shows the identification of κB sequence-binding protein in DNA/protein complexes using the super-shift assay.

Figure 10A:
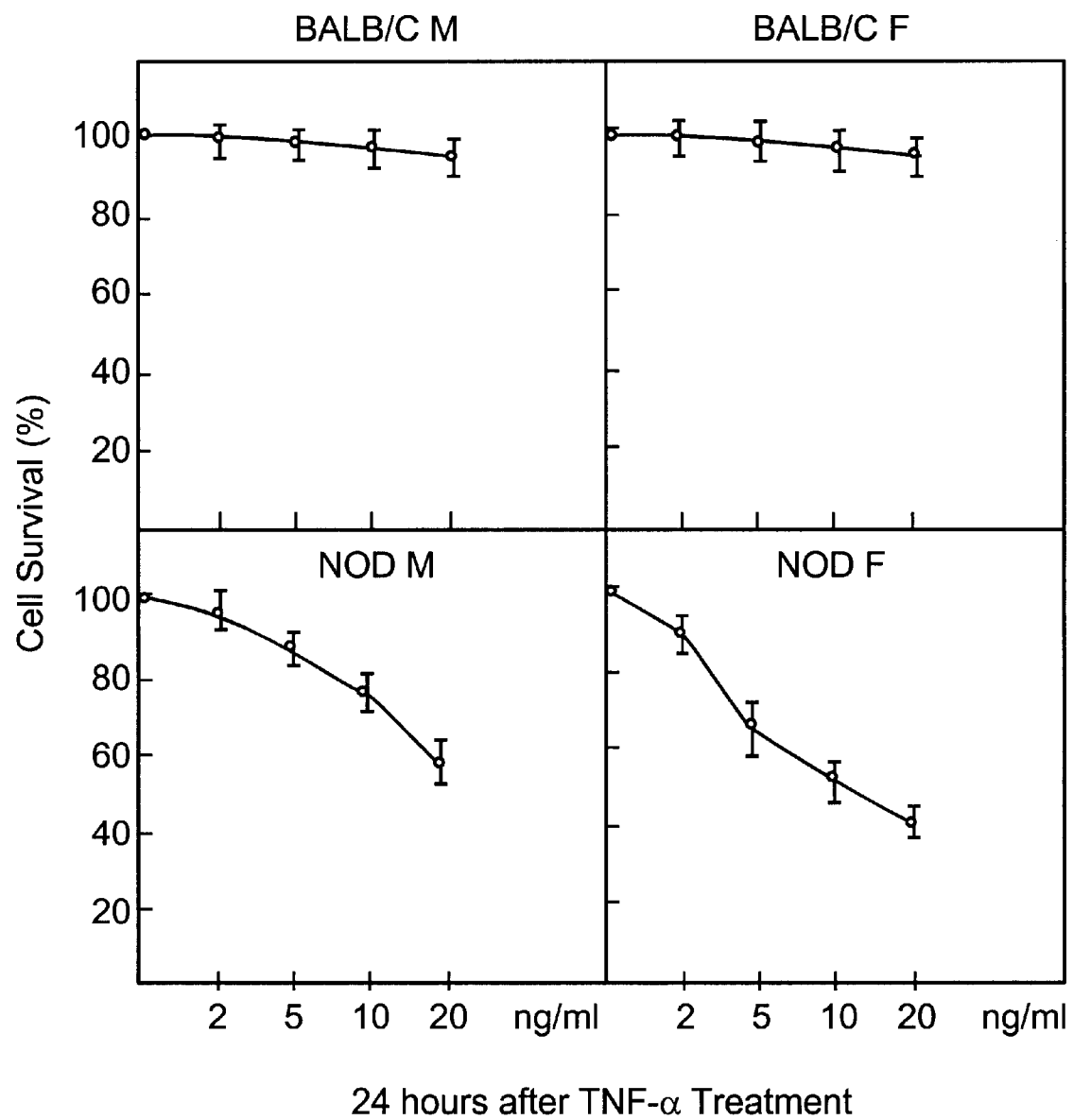
Figure 10B:
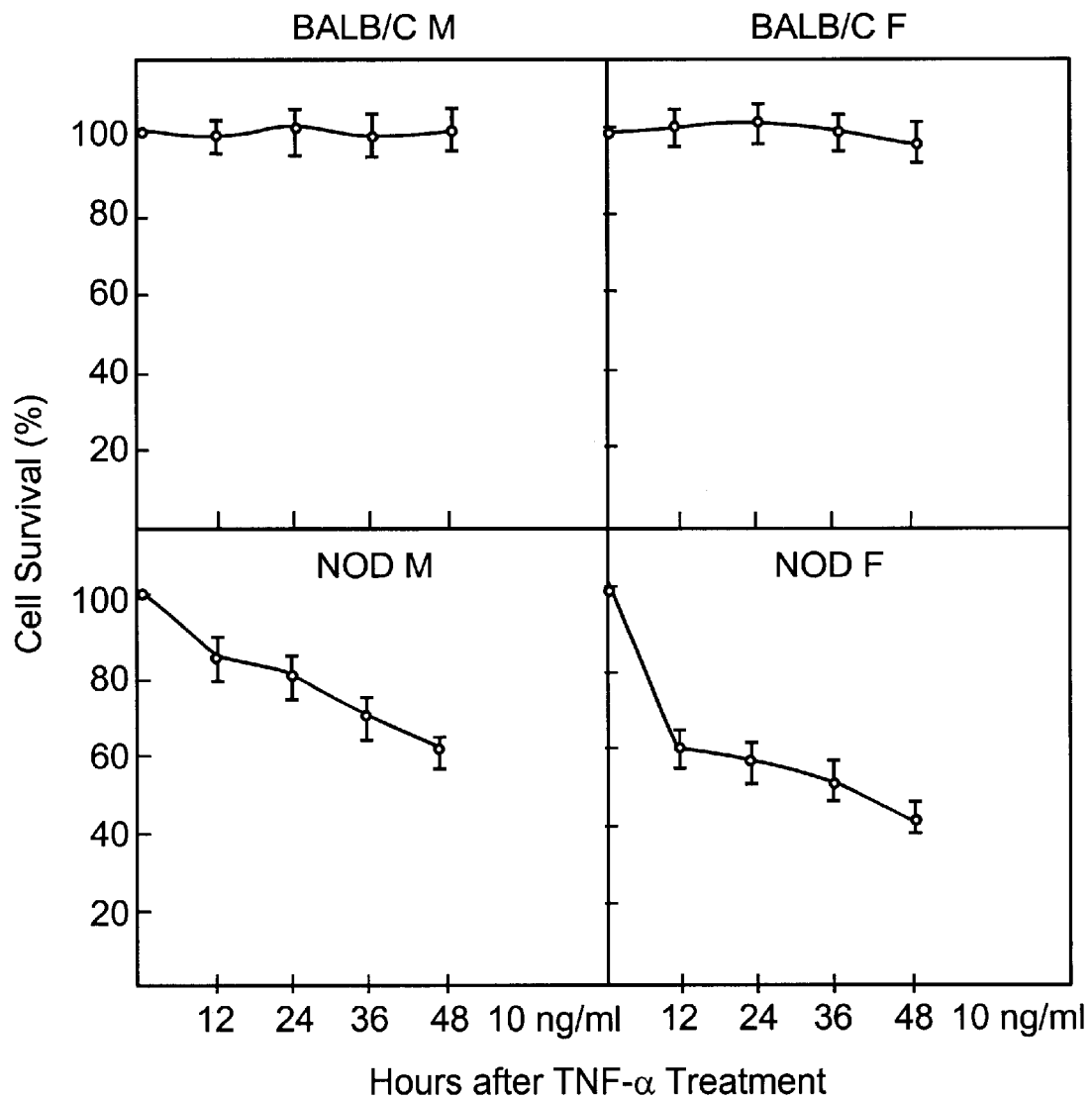

FIG. 10 shows TNF-α cytotoxicity to spleen cells derived from BALB/c and NOD mice.

DESCRIPTION OF THE INVENTION

The present invention is predicated on the discovery that NOD mice are deficient for NFκB activity. As described herein below, the methods and of the present invention comprise restoration of proteasome function, or simply that of NFκB, in the treatment of autoimmune disorders. The inventive methods are therefore contrary to prior art methods and, indeed, unexpected, based upon prior art references, which teach suppression of NFκB or of proteasome activity (and, consequently, that of NFκB) as a method of treating autoimmune disorders (see above). Restoration of proteasome function or of NFκB activity may be directed at the proteasome, the ubiquitinating machinery or protein kinases. Alternatively, therapy may involve providing functional (active forms of) NFκB that is independent of the proteasome for activation or even the products of downstream genes normally under the transcriptional control of NFκB or providing the cell with cytoplasmic forms of NFκB for cell cycle control and cell differentiation/viability. The object of such treatment is to inhibit the progression of an autoimmune disease or to prevent its clinical initiation, where "clinical initiation" refers to the presentation of symptoms and to organ destruction.

Detection of Defects in Proteolytic Processing

The invention contemplates detection of autoimmune disease by detecting a defect in proteasome activity. Such defects may be detected using the following assays.
i. The Proteasome Proteasome activity may be assayed as previously described (Gaczynska et al., 1994, *Proc. Natl. Acad. Sci. U.S.A.,* 91: 9213–9217, incorporated herein by reference). Briefly, cells (whether cultured cells, or those of an model animal, such as a mouse) in which the efficacy of a stimulator of proteasome activity is to be assayed prior to administration to a human are homogenized in a Dounce homogenizer or other grinding device (e.g. a mortar and pestle or a blender) and then by vortex mixing with glass beads in a homogenization buffer (40 mM Tris.HCl, 5 mM MgCl$_2$, 2 mM ATP, 250 mM sucrose, pH 7.4). Fractions containing total 20S and 26 S proteasomes are isolated by differential centrifugation of homogenates: for 20 minutes at 10,000×g, then for 1 hour at 100,000×g or for 5 hours at 100,000×g. Pellets are solubilized in 50 mM Tris.HCl, 5 mM MgCl$_2$, 2 mM ATP, 20% (volume/volume) glycerol, pH 7.4. Resulting "proteasome fractions" are used for peptidase assays and Western blot analysis. Degradation of the fluorogenic peptides, N-succinyl-Leu-Leu-Val-Tyr-7-amino-4-methylcoumarin (Suc-LLVY-MCA) (SEQ ID NO:1) N-tert-butoxycarbonyl-Leu Arg-Arg-7-amido-4-methylcoumarin (Boc-LRR-MCA) (SEQ ID NO:2) and N-carbobenzoyx-Leu-Leu-Glu-β-naphthylamide (Cbz-LLE-βNA) (SEQ ID NO:3) is assayed at 37° C., for 40 minutes or 1 hour in the presence of apyrase (5 units/ml), as described previously described (Gaczynska et al., 1993, *Nature,* 365: 552–554, also incorporated herein by reference).
ii. Ubquitination The invention contemplates detection of autoimmune disease by detecting a defect in the activity of ubiquitinating enzymes. Such defects may be detected using the following assays: Western analysis with antibodies directed against active forms of ubiquitinating enzymes, observation of eletrophoretic mobility of on a Western blot of the ubiquitinated form of a test protein or peptide relative to its non-ubiquitinated form or its proteolytically processed form relative to its unprocessed form in cytoplasmic extracts of unknown ubiquitinating capacity, Northern analysis to detect loss of mRNAs whose transcription is dependent upon a protein which required ubiquitination or enzymatic or other assay to determine the function of a protein or peptide incubated in a cytoplasmic extract of unknown ubiquitinating capacity, wherein the protein or peptide requires ubiquitination in order to undergo proteolytic activation. In vitro ubiquitination assays are known in the art (see Chen et al., 1995, *Genes Dev.,* 9: 1586–1597; Corsi et al., 1995, *J. Biol. Chem.,* 270: 8928–8935; Corsi et al., 1997, *J. Biol. Chem.,* 272: 2977–2983; Mori et al., 1997, *Eur. J. Biochem.,* 247: 1190–1196; Verma et al., 1997, *Mol. Cell. Biol.,* 8: 1427–1437; Kumar et al., 1997, *J. Biol. Chem.,* 272: 13548–13554).
iii. NFκB The invention contemplates detection of autoimmune disease by detecting a defect in the activation of NFκB. Such defects may be detected using the following assays.

The presence or absence of NFκB activity may be assayed by immunological analysis of protein from cells or individuals using anti-NFκB antibodies (in which one would expect to observe a band the size of IκB-free NFκB). Such protein may be derived from a biological sample, including, but not limited to, a tissue, cell, cell lysate or body fluid from an individual. Northern analysis using labeled nucleic acid probes specific for transcripts that may be produced by the downstream targets of NFκB (i.e., genes which are transcriptionally activated by that protein) may be performed. Alternatively, nuclear protein extracts may be prepared from such cells and tested for the ability to activate transcription in vitro of a marker gene which is operatively linked to an NFκB-inducible gene regulatory sequence. Assays may be directed at individual NFκB subunits, such as p50 and p65, as in Examples 1 and 2 below, wherein the cytoplasmic and nuclear functions of these subunits are tested in normal and autoimmune mice. In addition to activity, their processing from a larger protein or release from inhibitory substances may be assessed by molecular and biochemical methods known in the art (such as PAGE or Western analysis, as described below).

While these approaches are technically feasible, they may not be medically expedient or even safe, as they entail removal of treated cells from the patient. It is recommended that immunological analysis be performed on serum protein extracts, using antibodies which are directed against products of genes under the control of NFκB which are secreted proteins, by methods described below.

Restoration of Normal Proteolytic Processing

The invention contemplates methods of treating autoimmunity by restoring proteolytic processing, based upon the observation that NFκB activity is absent in the NOD mouse model of autoimmune disease. Restoration of proteolytic processing, such as would result in the restoration of NFκB activity, may be directed at the proteasome, the ubiquitinating machinery or protein kinases.

A. Therapeutic Targets

Suppression of Proteasome Inhibitors

The invention contemplates methods of treating autoimmunity by restoring proteolytic processing by blocking the activity of inhibitors of proteasome function or changing the specificity of a proteasome subunit to favor activation of the substrate(s) deficient in an autoimmune disease, so that correct protein processing is restored.

Inhibition of proteasome activity blocks the production of activated NFκB and other essential proteins, as described above; therefore, in order to promote correct protein processing, it may be necessary to inactivate cellular inhibitors of the proteasome. Such endogenous inhibitors of proteasome activities have been isolated. These include the 240 kD and the 200 kD inhibitors isolated from human erythrocytes (Murakarni et al., 1986, *Proc. Natl. Acad. Sci. U.S.A.*, 83: 7589–7592; Li et al., 1991, *Biochemistry*, 30: 9709–9715) and purified CF-2 (Goldberg, 1992, *Eur. J. Biochem.*, 203: 9–23).

Endogenous proteasome inhibitors may be inactivated by methods known in the art, which methods include the administration of antibodies which bind them specifically, the use of antisense RNA or ribozymes directed against the mRNAs which encode them (see below). Antibodies against numerous proteins are now publicly available, both through commercial and non-profit suppliers (e.g. ATCC); however, antibodies of use in the invention may, if necessary, be prepared as described below.

Restoration of Wild-type Proteasome Function

The invention contemplates methods of treating autoimmune disease by direct stimulation of proteasome function, thereby restoring or preserving correct proteolytic processing.

Japanese Patent No. JP8322576, which is herein incorporated in full by reference, discloses proteasome activator PA28β (see also Chu-ping et al., 1992, *J. Biol. Chem.*, 267: 10515; Dubiel et al., 1992, *J. Biol. Chem.*, 267: 22369); both cloning of a cDNA from bovine tissues (e.g. liver, heart and red blood cells) and a method for the production of the recombinant polypeptide encoded by the cloned nucleic acids are described by these references. PA28 (or PA28β) has a subunit molecular weight of 28,000, as judged by denaturing gel electrophoresis and a native molecular weight of approximately 180,000 as determined by gel filtration and density gradient centrifugation; therefore, it is thought to exist as a hexameric protein complex. Dubiel et al. (1992, supra) further describe the isolation of a human protein of $M_r$ approximately 200,000 that activates proteasomes; this complex is a hexamer comprising subunits that display $M_r$ of approximately 29,000 and 31,000 on danaturing electrophoretic gels. This activator complex lacks intrinsic peptidase activity, but stimulates proteolysis of certain substrates about 60-fold, although activated proteasomes are unable to degrade ubiquitin-lysozyme conjugates, bovine serum albumin or lysozyme; activation involves reversible binding of the activator complex to proteasomes. WO 95/27058 discloses a human protein complex ($M_r$ approximately 29,000) which is a γ-interferon-inducible activator of proteasome function. The sequences encoding each of these polypeptides are of use in gene therapy according to the invention, as described below. Alternatively, the proteins themselves may be administered by methods known in the art (see also below).

In addition to proteasome-stimulating proteins, wild-type proteasome subunits or other associated proteins (e.g. Lmp2, Lmp7) may be administered if inactivating mutations are found within the sequences encoding them or in the regulatory elements controlling the transcription or these genes. While there exist many targets for such specifically-directed treatment, it should be noted that the discovery of one such mutant (that found in the shared Lmp2/Tap promoter) is described herein above (Yan et al., 1997, supra).

Restoration of Correct Ubiquitination/ Phosphorylation

The invention contemplates methods of treating an autoimmune disease by restoring correct patterns of ubiquitination and/or phosphorylation.

If proteolytic failure has been traced to a deficiency in ubiquitination or phosphorylation, the missing activity may be supplemented either through the administration of a wild-type protein whose absence or inactivation is responsible for the deficiency or through gene therapy, in which a gene encoding such a protein is administered under the influence of transcriptional control elements (e.g., its own wild-type element or another strong promoter, e.g. thymidine kinase, heat-shock or others as are known in the art). Such proteins may include ubiquitinating proteins of the E1, E2 and E3 families as well as "glue" proteins (all as described above); alternatively, protein kinases (e.g., cyclin-dependent kinases; see also above) or cyclins may be administered.

Restoration of NFκB Function

The invention contemplates methods of treating autoimmune diseases by restoring NFκB function, which, in turn, restores the transcription of NFκB-dependent genes.

As is true of the proteasome and of the ubiquitination and protein phosphorylation machinery described above, it is possible to administer to cells of an organism in which NFκB carries an inactivating mutation, either in coding or regulatory sequences, a wild-type sample of the NFκB protein or one or more copies of the gene encoding it; however, a second scenario may instead be envisioned.

In the case in which NFκB activity is reduced or absent due to an 'upstream' defect (that is, one involving activation by the proteasome, instead of- or in addition to a mutation in the NFκB gene itself), it is possible to circumvent the need for proteolytic activation of NFκB by introducing a constitutively-active version of the protein, such as one in which the IκB recognition site has been mutated such that IκB can no longer bind to- and inactivate NFκB. Binding of NFκB to IκB occurs through ankyrin repeats (as reviewed by Siebenlist et al., 1994, *Ann. Rev. Cell. Biol.*, 10: 405–455); it is contemplated that sequences encoding these repeats be deleted or mutated in an NFκB subunit p100 or p105 gene expression construct such that binding to IκB is significantly impaired or is eliminated. As a transcription/signalling factor which remains active when it is no longer required may have undesirable consequences, particularly in the absence of proteolytic which would normally inactivate it under such circumstances, administration of such a protein in limited doses or of a gene encoding it under a tightly-regulated (i.e. inducible, rather than constitutive, promoter) may be necessary. Alternatively, such a protein may be expressed at all times, provided that an inhibitor thereof is co-administered; such an inhibitor may be an antibody directed against the protein, or an antisense RNA or ribozyme directed against the message encoding it, as described below.

Inactivation of IκB may also be performed by methods described below, such as by the use of antibodies directed against it or of antisense RNA or ribozymes directed against the mRNA transcript encoding it. Preferably, such inactivation is transient, as it would otherwise lead to constitutive activation of NFκB, which activation is not, itself, normal.

The invention contemplates treatment of autoimmune disease using methods directed at the potential therapeutic targets discussed above. In the section following, methods by which such treatment may be carried out are presented.

B. Therapeutic Methods

Autoimmune Disorders in Humans

In order to provide effective treatment according to methods contemplated by the invention, it is first necessary to identify those individuals in need of treatment.

Genetic linkage studies have confirmed the MHC to be an important contributor to human autoimmune diseases such as type I diabetes, rheumatoid arthritis, lupus erythematosus, Hashimoto's disease, and multiple sclerosis (Bach et al., 1994, *Endocr. Rev.*, 15: 516; Cudworth and Woodrow, 1976, *Br. Med. J.*, 2: 846; Festenstein et al., 1986, *Nature*, 322: 64; Nerup et al., 1977, *HLA and Disease*, Munksgaard, Copenhagen; Todd et al., 1987, *Nature*, 329: 599; Van Endert et al., 1994, *Diabetes*, 43: 110). Other autoimmune disorders include Graves' disease, ulcerative colitis, Crohn's disease, polyendocrine failure, Sjögren's syndrome and others as listed above in the Summary.

The present invention is of use in the treatment of HLA class II-linked autoimmune diseases such as those listed above. Diagnostic symptoms or other indicators may be used either to assess a patient for the presence of- or susceptibility to such a disorder; in addition, improvement (i.e., a change toward the basal state, as defined above) in one or more of these indicators is indicative of the efficacy of a given method of treatment for such a disease.

Examples of autoimmune disease-related symptoms for several representative diseases are as follows:

Addison's Disease

Addison's disease is a disorder characterised by failure of the adrenal gland and is often an autoimmune disorder involving destruction of the adrenal cortex and the presence of adrenal autoantibodies in the patient's serum. The adrenal cortex is responsible for producing several steroid hormones including cortisol, aldosterone and testosterone. In autoimmune Addison's disease and other forms of the disease, levels of these hormones are reduced. This reduction in hormone levels is responsible for the clinical symptoms of the disease which include low blood pressure, muscle weakness, increased skin pigmentation and electrolyte imbalance.

Autoantibodies to the adrenal cortex may be identified for diagnosis of Addison's disease using the technique of complement fixation or immunofluorescence (Anderson et al., 1957, *Lancet*, 1: 1123–1124; Blizzard and Kyle, 1963, *J. Clin. Invest.*, 42: 1653–1660; Goudie et al., 1968, *Clin. Exp. Immunol.*, 3: 119–131; Sotosiou et al., 1980, *Clin. Exp. Immunol.*, 39: 97–111). Radioimmunoassay and ELISA techniques using crude adrenal membrane preparations are also of use in the invention (Stechemesser et al., 1985, *J. Immunol. Methods*, 80: 67–76; Kosowicz et al., 1986, *Clin. Exp. Immunol.*, 63, 671–679).

U.S. Pat. No. 5,705,400 discloses methods for the detection of adrenal autoantigen. Such assays are useful for the diagnosis of latent or actual autoimmune Addison's disease. These methods are briefly summarized as follows:

1. Assay Based on a Radioactive Label

Purified adrenal autoantigen is labeled with a radioactive label such as $^{125}I$ using one of many well-known techniques. The labeled material is then incubated (1 hour at room temperature) with a suitably diluted (e.g. 1:20 in phosphate buffered saline) serum sample. Adrenal autoantibodies present in the test sample bind to the $^{125}I$-labeled adrenal autoantigen and the resulting complex is precipitated by addition of antibodies to human immunoglobulins or a similar reagent (e.g. solid phase Protein A). The amount of $^{125}I$-labelled antigen in the precipitate is then determined. The amount of adrenal autoantibody in the test serum sample is a function of the amount of radioactivity precipitated. The amount of adrenal autoantibody can be expressed as the amount of radioactivity in the pellet or more usually by including dilution of an adrenal autoantibody-positive reference serum in the assay. Note that such techniques using autoantigens such as have been identified in other diseases may be broadly applied to the detection of autoantibodies.

2. Assay Based on an Enzyme Label

Purified adrenal autoantigen is coated onto plastic wells of ELISA plates either directly onto plain wells or indirectly. The indirect method may involve coating the wells first with a monoclonal or polyclonal antibody to adrenal autoantigen (the antibody is selected so as not to bind to the same site as adrenal autoantibodies) followed by addition of adrenal autoantigen. Several other indirect coating methods are well known in the art. After coating with autoantigen, suitably diluted (e.g., 1:20 in phosphate buffered saline) test sera are added to the wells and incubated (1 hour at room temperature) to allow binding of adrenal autoantibody to the antigen coated onto the wells. The wells are then washed and a reagent such as antihuman IgG conjugated to horseradish peroxide is added. After further incubation (e.g., 1 hour at room temperature) and washing, an enzyme substrate such as orthophenylene diamine is added and the color generated measured by light absorbance. The amount of adrenal autoantibody in the test sample is a function of the final color intensity generated. Results are expressed as light absorbance or, more usually, by including dilution of an adrenal autoantibody positive reference serum in the assay.

Ulcerative Colitis and Crohn's Disease

A number of human diseases result in the subject having a diseased gut in which digestion or absorption is impaired. Examples of autoimmune diseases in humans include chronic ulcerative gut diseases (e.g., ulcerative colitis) and inflammatory gut diseases such as colitis and Crohn's disease.

In addition to impaired digestion and inflammation and/or ulteration of the intestinal tract, symptoms include pain, bleeding, abnormal stool production and weight loss. Such symptoms may be assessed either by patient interview or through techniques such as endoscopy and other imaging techniques such as heavy metal (e.g. barium enema followed by X-ray), and scanning using CAT, positron emission tomography (PET), (magnetic resonance imaging) MRI or histological analysis (biopsy).

Lupus Erythematosus

As described by U.S. Pat. Nos. 5,695,785 and 5,700,641, and briefly summarized here, lupus erythematosus is an autoimmune disease which is not specific to a particular organ. The common type of lupus erythematosus, Discoid Lupus Erythematosus (DLE), affects exposed areas of the skin. The more serious and fatal form of the disease, Systemic Lupus Erythematosus (SLE), affects a large number of organs and has a chronic course with acute episodes. The external manifestations of SLE are lesions on the facial skin. In most cases, other areas of skin and the mucosa are affected. Also observed are nephritis, endocarditis, hemolytic anemia, leukopenia and involvement of the central nervous system.

Many immunological phenomena have been observed with SLE. For example, the formation of antibodies against certain endogenous antigens has been seen. These antibodies are directed against, for example, the basement membrane of the skin, and against lymphocytes, erythrocytes and nuclear antigens. Antibodies which are directed against double-stranded DNA (ds-DNA) form with the latter complexes. These antibodies, together with complement, are deposited on small blood vessels and frequently result in vasculitis. These deposits are especially dangerous when they occur in the renal glomeruli because they result in glomerulonephritis and kidney failure. The incidence of clinically detectable kidney involvement is reported in the literature to be between 50 and 80%.

Of the multitude of autoreactive antibodies that spontaneously arise during the disease, high levels of circulating autoantibodies to DNA are the best evidence of the pathogenesis. In SLE, there is almost invariable presence in the blood of antibodies directed against one or more components of cell nuclei. Certain manifestations in SLE seem to be associated with the presence of different antinuclear antibodies and genetic markers, which have suggested that SLE may be a family of diseases (Mills, 1994, *Medical Progress*, 33: 1871–1879). Lupus nephritis, especially diffuse proliferative glomerulonephritis, has been known to be associated with circulating antibodies to double stranded (native) DNA (Casals et al., 1964, *Arthritis Rheum.*, 7: 379–390; Tan et al., 1964, *J. Clin. Invest.*, 82: 1288–1294). The detection of antinuclear antibodies is a sensitive screening test for SLE. Antinuclear antibodies occur in more than 95% of patients (Hochberg, 1990, *Rheum. Dis. Clin. North Am.*, 16: 617–639). Such autoantibodies may be detected using DNA or other cellular components (such as small nuclear ribonucleoprotein complexes) by the methods described above.

Sjögren's Syndrome

Tear film dysfunctions are collectively diagnosed as keratoconjunctivitis sicca (KCS) or, simply, dry eye (Holly et al., 1987, *Internat. Opthalmol. Clin.*, 27: 2–6; Whitcher, 1987, *Internat. Opthalmol. Clin.*, 27: 7–24). Lacrimal gland abnormalties falling into the category of aqueous tear deficiencies, which are most frequently responsible for dry eye states, include autoimmune disease. By far, the greatest single cause of KCS worldwide, excluding those countries wherein trachoma remains epidemic, is Sjögren's syndrome (Whitcher, 1987, supra). This syndrome, which is the second most common autoimmune disease (Tabbara, 1983, "Sjögren's Syndrome" in *The cornea, Scientific Foundations and Clinical Practice*, Smolin and Thoft, eds., Little Brown and Co., Boston, Mass., pp. 309–314; Daniels, 1990, "Sjögren's Syndrome—in a nut shell" in *Sjögren's Syndrome Foundation Inc. Report*, Port Washington, N.Y.). This disease occurs almost exclusively in females and is characterized by an insidious and progressive lymphocytic infiltration into the main and accessory lacrimal glands, an immune mediated extensive destruction of lacrimal acinar and ductal tissues and the consequent development of persistent KCS (Tabbara, 1983, supra; Moutsopoulos and Talal, 1987, in *Sjögren's Syndrome, Clinical and Immunological Aspects*, Talal et al., eds., Springer Verlag, Berlin, pp. 258–265; Talal and Moutsopoulos, 1987, in *Sjögren's Syndrome, Clinical and Immunological Aspects*, Talal et al., eds., Springer Verlag, Berlin, pp. 291–295; Kincaid, 1987, in *Sjögren's Syndrome, Clinical and Immunological Aspects*, Talal et al., eds., Springer Verlag, Berlin, pp. 25–33). In primary Sjögren's syndrome, which afflicts about 50% of the patient population, the disease is also associated with an immunological disruption of the salivary gland and pronounced xerostomia. In secondary Sjögren's, the disorder is accompanied by another autoimmune disease, which is most often rheumatoid arthritis and, less frequently, systemic lupus.

Dryness of the eyes, infiltration of lymphocytes into the lacrymal glands and the presence of autoantibodies are diagnostic criteria for Sjögren's disease that are of use in the invention. The restoration one, more than one or even all of these indices to the basal state is indicative of effective treatment.

Type I Diabetes

Insulin dependent diabetes mellitus (IDDM) (also known as type I diabetes) primarily afflicts young people. Although insulin is available for treatment the several-fold increased morbidity and mortality associated with this disease require the development of early diagnostic and preventive methods, as well as methods for the restoration of normal insulin secretion (e.g., with islet therapy or regeneration os endogenous islets by methods described in detail below). As described in U.S. Pat. No. 5,691,448 and summarized briefly herein, the disappearance of pancreatic β-cells (which are the insulin-secreting cells of the islets of Langerhans) precedes the clinical onset of IDDM. Among the most thoroughly studied autoimmune abnormalities associated with the disease is the high incidence of circulating β cell-specific autoantibodies years prior to frank hyperglycemia, the typical clinical diagnosis. Family studies have shown that the autoantibodies appear prior to overt IDDM by years, suggesting a long prodromal period of humoral autoimmunity before clinical symptoms emerge, and have also documented a slow, progressive loss of insulin response to intravenous glucose in the years preceding diagnosis. The presence of β cell-specific autoantibodies in the prediabetic period allows for diagnosis according to the invention prior to critical β-cell depletion and insulin dependency. It has been estimated that only 10% of the total β-cell mass remains at the time of clinical onset (i.e., presentation of elevated blood glucose levels relative to those observed in unaffected individuals, who represent the basal state, as defined above).

The target of autoantibodies in pancreatic β-cells in IDDM were originally identified as both insulin and a 64 kD autoantigen by immunoprecipitation experiments using detergent lysates of human islets (Baekkeskov et al., 1982, *Nature*, 298: 167–169). Antibodies to the 64 kD autoantigen precede the clinical onset of IDDM and have been shown to have an incidence of about 80% at clinical onset and during the prediabetic period (Baekkeskov et al., 1987, *J. Clin. Invest.*, 79: 926–934; Atkinson et al., 1990, *Lancet*, 335: 1357–1360; and Christie et al., 1988, *Diabetologia*, 31: 597–602. Many other autoantibodies exist, most directed against intracellular proteins.

A therapeutic agent is administered to a patient suspected of suffering- or suffering from established diabetes in an amount suffcient to inhibit or prevent further β-cell destruction/death. For individuals at risk of IDDM or stiff man syndrome, the pharmaceutical agent is administered prophylactically in an amount sufficient to either prevent or inhibit destruction and death of the β-cell. According to the invention, a therapeutic agent is administered in an amount and for a time sufficient to prevent or inhibit β cell destruction; β cell survival, as judged by immunological detection of insulin, the level of serum glucose levels or restoration of vigorous insulin stimulation to glucose challenge (intravenous glucose tolerance test, or IVGTT; Joslin, 1985, *Diabetes Mellitus. 20th Edition*, eds. Marble et al., Lea & Febiger, Philadelphia, Pa.), is indicative of effective treatment.

Multiple Sclerosis

The symtoms of multiple sclerosis, such as those described in *Treatment of Multiple Sclerosis: Trial Design, Results, and Future Perspectives*, eds. Rudick and Goodkin, Springer-Verlag, NY, 1992 (particularly those symptoms described on pages 48–52), incorporated by reference as if fully set forth herein.

These multiple sclerosis symptoms include perturbations of pyramidal functions, for example the developement of paraparesis, hemiparesis, monoparesis, quadriparesis and the developement of monoplegia, paraplegia, quadriplegia, and hemiplegia. The symptoms of multiple sclerosis also include perturbations in cerebellular functions. These perturbations include the developement of ataxia, including truncal and limb ataxia. When we refer to "paralytic symptoms of multiple sclerosis" we are refering to these perturbations in pyramidal and cerebellar funtions. The symptoms of multiple sclerosis also include changes in brain stem funtions, including development of nystamus and extraocular weakness along with dysarthria. Further symptoms include loss of sensory function including decrease in touch or position sense and loss of sensation in limbs. Perturbations in bowel and bladder function, including hesitancy, urgency, retention of bowel or bladder or incontinence, can also occur. Visual functions, such as the development of scotoma, are also affected by multiple sclerosis. Cerebral function degeneration, including a decrease in mentation and the developement of dementia, is also a symptom.

Inflamed MS and EAE (see below) lesions, but not normal white matter, sometimes have infiltrating CD4 T cells that respond to self antigens presented by MHC class II-linked molecules like human HLA-DR2 (MS) or murine I-$A^M$ (EAE). The infiltrating CD4 Tcells (Th1 cells) produce proinflammatory cytokines interleukin (IL)-2, interferon (IFN)-γ, and tumor necrosis factor (TNF)-α that activate antigen-presenting cells like macrophage to produce inflammatory cytokines (IL-1β, IL-6, and IL-8) and IL-12. The IL-12 induces further IFN-γ synthesis. The imbalance of one or more of these proteins relative to other cellular factors may be assayed by biochemical or immunological methods as are known in the art. Such methods are described below. The disclosure of the present invention of poor NFκB function inside cells of autoimmune mammals implicates decreased resistance of target tissues to such inflammatory cytokine insults.

To evaluate whether a patient is benefitting from treatment, the patient's symptoms are examined in a quantitative way, such as by the EDSS (Rudick and Goodkin, supra), or decrease in the frequency of relapses, or increase in the time to sustained progression, or improvement in the magnetic resonance imaging (MRI) behavior in frequent, serial MRI studies and compare the patient's status measurement before and after treatment. In a successful treatment, the patient status will have improved, i.e., the EDSS measurement number or frequency of relapses will have decreased, or the MRI scans will show less pathology.

Preferably, treatment should continue as long as multiple sclerosis symtoms are suspected or observed.

Rheumatoid Arthritis

In rheumatoid arthritis, the main presenting symptoms are pain, stiffness, swelling, and loss of function (Bennett, 1984, "The etiology of rheumatoid arthritis" in *Textbook of Rheumatology*, Kelley et al., eds., W. B. Saunders, Philadelphia, pp. 879–886). The multitude of drugs used in controlling such symptoms seems largely to reflect the fact that none is ideal. Although there have been many years of intense research into the biochemical, genetic, microbiological, and immunological aspects of rheumatoid arthritis, its pathogenesis is not completely understood, and none of the treatments clearly stop progression of joint destruction (Harris, 1985, "Rheumatoid Arthritis: The clinical spectrum" in *Textbook of Rheumatology*, Kelley. et al., eds., W. B. Saunders, Philadelphia, pp. 915–990).

TNF-α is present in rheumatoid joint tissues and synovial fluid at the protein and mRNA level (Buchan et al., 1988, *Clin. Exp. Immunol.*, 73: 449–455), indicating local synthesis. Detection of this protein by methods described herein below (e.g. enzyme immunoassay, EIA, or enzyme-linked immunosorbent assay, ELISA) provides a diagnotic indicator of arthritis independent of clinical symptoms. In addition, autoantibodies may be quantified as described above.

Analysis of improvement in individual patients following treatment is made using two separate indices. Firstly, an index of disease activity (IDA) is calculated for each time point according to the method of Mallya and Mace (Mallya et al., 1981, *Rheumatol. Rehab.*, 20: 14–17, the contents of which are fully incorporated herein by reference) with input variable of morning stiffness, pain score, Richie Index grip strength, ESR and Hgb. The second index calculated was that of Paulus (Paulus et al., 1990, *Arthritis Rheum.*, 33: 477–484, the contents of which are fully incorporated herein by reference) which uses input variables of morning stiffness, ESR, joint pain/tenderness, joint swelling, patient's and Physician's global assessment of disease severity.

Rheumatoid factors may be measured using the rheumatoid arthritis particle agglutination assay (FAPA, FujiBerio Inc., Tokyo, Japan), in which titers of $\frac{1}{160}$ or greater are considered significant. Rheumatoid factors are measured by ELISA (e.g. using a kit supplied by Cambridge Life Sciences, Ely, UK).

Hashimoto's Disease (Hypothyroidism)

Symptoms include low levels of circulating thryoid hormone, tiredness, yellow skin discoloration, delayed reflexes, slowed heartrate, with eventual edema leading to coma and death.

Graves' Disease (Hyperthyroidism)

Symptoms include high levels of circulating thyroid hormone, hyperactivity, inability to sleep, thinning hair, irritable bowel and orbital abnormality (protruding eyes).

Vitiligo

This disorder is characterized by melanocyte loss in a characteristic pattern on the body. It is initially diagnosed; as is true of other autoimmune diseases affecting the skin (see "psoriasis" and "pemphigus vulgaris", below), tissue biopsy is performed to confirm diagnosis.

Psoriasis

The symptom of psoriasis, also present for visual diagnosis, is scaly skin.

Pemphigus Vulgaris

Symptoms of pemphigus vulgaris include skin peeling and scaling. It, too, is diagnosed visually and by skin biopsy.

In addition, genetic diagnosis of autoimmune disease, which is an effective means of early diagnosis, is possible for diseases for which genetic linkage (pedigree) studies have been performed for large (or, alternatively, small but numerous) families of affected individuals. Early diagnosis may, additionally, be facilitated by the simple assay of NFκB activity in individuals deemed to be at risk of disease; methods by which NFκB are described herein, and include in vitro DNA/protein binding and/or transcriptional activation assays.

In order to ensure the safety of treatments according to the invention, following treatment of arthritis or another autoimmune disease, vital signs are recorded at intervals for up to 24 hours following administration of the therapeutic agent. Patients are later questioned concerning possible adverse events before each treatment. Preferably, a complete physical examination is performed at the time of initial diagnosis. In addition, patients may be monitored by standard laboratory tests including complete blood count, C3 and C4 components of complement, IgG, IgM and IgA, serum electrolytes, creatinine, urea, alkaline phosphatase, aspartate transaminase and total bilirubin. Urine analysis may, additionally, be performed.

Prior to testing potential therapeutic compositions and methods on human subjects, testing is performed in an animal model. It is generally accepted by those of skill in the art that results obtained through the use of animal models are predictive of the efficacy of a given treatment in a human clinical patient. The following section describes a selection of animal models which are of use in assessing the efficacy of proposed treatments of autoimmune disease according to the invention.

Animal Models of Autoimmune Disease
i. Mouse Models

Animal models such as the NOD$^3$ (or, simply, NOD) mouse, which is prone to diabetes, Sjögren's syndrome and hemolytic anemia have also demonstrated the importance of the H2 (again, the mouse MHC) genomic region, in combination with non-H2 genes in autoimmunity. The inheritance of MHC and MHC-linked genes with minimal recombinations (linkage disequilibrium), together with the fact that most of these genes contribute to immune responses, has hampered the identification of the genes that underlie autoimmunity. Polymorphisms are abundant in the MHC and are readily detected but the challenge remains to identify those polymorphisms that contribute to disease susceptibility and have functional consequences, and to define the disease-causing mechanisms.

NOD mice, like humans with type I diabetes, exhibit a phenotype in which conformationally abnormal forms of class I molecules (which can be detected with conformationally specific antibodies) are present on the surface of APCs (Faustman et al., 1992, supra). The exit of class I molecules from the endoplasmic reticulum (ER) of NOD mouse APCs is delayed, and the presentation of test antigens by these cells is markedly impaired in in vitro assays of cytotoxic T cell lysis (Li et al., 1994, supra). Surface class I molecules of NOD mouse APCs can be stabilized by culture at low temperature or by the addition of allele-specific peptides that presumably occupy the empty peptide-binding pockets of the class I protein.

Impaired antigen presentation and class I assembly may be essential for disease expression in diabetes-prone NOD mice and humans. Only NOD females who progress to hyperglycemia or salivary gland destruction possess the defect; normoglycemic NOD males, 15% of which develop diabetes, lack the APC defect.

The NOD mouse exhibits a rare MHC haplotype known as H-2$^{g7}$, in which many polymorphisms are apparent (Hattori et al., 1986, supra; Lund et al., 1990, *J. Autoimmun.*, 3: 289; Prochazka et al., 1987, *Science*, 237: 286; Acha-Orbea and McDevitt, 1987, *Proc. Natl. Acad. Sci. U.S.A.*, 84: 2435). For instance, the NOD mouse has a rare Tap1 allele with a transcription defect (Faustman et al., 1991, supra), an uncommon Lmp2 allele with a transcription defect, and a unique MHC class II gene at the I-A locus. The quantitative defect in Tap1 transcription, like the class I cell surface assembly abnormality, correlates with disease expression in NOD mice, again demonstrating a pattern of gene expression that can be influenced by the environment (Huang et al., 1995, *Diabetes*, 44: 1114), gender or noninherited gene phenomena (e.g. somatic gene rearrangements or changes in gene methlyation pattern). Many of these genes have similar promoters and respond in unison to external stimuli. In the case of Tap1 and Lmp2, the genes even share the same promoter in opposing orientations. Therapies based on nonspecific immunostimulation, such as injection with CFA or infection with mouse hepatitis virus, ameliorate diabetes in NOD mice. These treatments also increase the rate of Tap1 transcription, and re-educated or reselected the 7 cell repertoire so that T cell autoreactivity to class I and syngeneic peptides is eliminated (Huang et al., 1995, supra). These data suggest transcription or quantitative issues of gene expression could be dominant in patterns of disease expression.

As in humans, lymphocytic developmental errors are characteristic of mouse (NOD) and rat (BB; see below) models of Type I diabetes (Shimada et al., 1996, *Diabetes*, 45: 71–78; Serreze et al., 1993, *Proc. Natl. Acad. Sci. U.S.A.*, 90: 9625–9629; Li et al., 1994, *Proc. Natl. Acad. Sci. U.S.A.*, 91: 11128–11132). For instance, mature T lymphocytes in peripheral blood, spleen and lymph nodes are markedly absent in autoimmune disease-prone BB animals (Crisa et al., 1992, *Diabetes Metabolism Rev.*, 8: 9–37). As might be expected of an immature lymphoid cell, diabetic lymphocytes in animal and human models demonstrate defective intracellular activation of signal transduction pathways, including responses to TNF, lipopolysaccharides (LPS, which are non-specific immunostimulants) and signal transduction along the microtubule-associated protein kinase (MAP kinase) pathway of T cell activation (Serreze et al., 1993, supra; Rapoport et al., 1993, *J. Exp. Med.,* 177: 1221–1226).

Given the established role of antigen presentation in T cell education and its impairment in numerous autoimmune diseases in both humans and mice, mutations which contribute to the abnormal antigen presentation and processing in the NOD mouse (made apparent, in part, by altered class I assembly and altered presentation of syngeneic peptides) are of significant interest; therefore, the NOD mouse provides a good model system in which genetic and environmental factors influencing autoimmune diseases can be studied. Recently, a mutation in the shared, bidirectional Lmp2/Tap1 promoter has been found to reduce expression of these genes in the NOD mouse (Yan et al., 1997, *J. Immunol.,* 159: 3068–3080).

ii. The BB Rat

Diabetes-prone BB rats have profound peripheral T lymphocyte immunodeficiencies and lack a surface maturation molecule or lymphocytes RT6, a member of the src tyrosine kinase family (Elder and Maclaren, 1983, *J. Immunol.,* 130: 1723–1731; Rigby et al., 1996, *Diabetes,* 45: 1419–1426; Jackson et al., 1983, *Metabolism,* 32: 83–86; Woda et al., 1986, *J. Immunol.,* 136: 856–859; Greiner et al., 1986, *J. Immunol.,* 136: 148–151).

iii. Other Models

Other animal models of autoimmune disease as are known in the art are as follows:

Experimental autoimmune encephalomyelitis (EAE) in mice and rats serves as a model for multiple sclerosis (M.S.) in humans. It is a CD4+ T-cell mediated autoimmune disease that is directed against protein components of CNS myelin (Miller and Karpus, supra, 1994). In this model, the demyelinating disease is induced by administration, typically by injection, of myelin basic protein (MBP), as described by Paterson, P. Y. (1986, *Textbood of Immunopathology,* eds. Mischer et al., Grune and Stratton, New York, pp. 179–213), McFarlin et al. (1973, *Science,* 179: 487–480) and Satoh et al. (1987, *J. Immunol.,* 138: 179–184). B10.PL mice are known to have histopathological and clinical similarities to the relapsing-remitting form of human M.S. (Miller and Karpus, 1994, *Immun. Today,* 15: 356); these mice develop EAE in response to injection with MBP. EAE is characterized by transient asscending paralysis of the affected mouse's limbs.

Systemic lupus erythematosis (SLE) is tested in susceptible mice as disclosed by Knight et al. (1978, *J. Exp. Med.,* 147: 1653). Myasthenia gravis (MG) is tested in SJL/J female mice by inducing the disease with soluble acetylcholinesterase receptor (AChR) protein from another species, as described by Lindstrom et al., (1988, *Adv. Immunol.,* 42: 233–284). Arthritis is induced in a susceptible strain of mice by injection of type II collagen, as described by Stuart et al., (1984, *Ann. Rev. Immunol.,* 42: 233–284). Thyroiditis is induced in mice by administration of thyroglobulin as described by Maron et al., (1980, *J. Exp. Med.,* 152: 1115–1120). Insulin-dependent diabetes mellitus (IDDM) occurs naturally or can be induced in certain strains of mice.

The contents of the above references relating to animal models of autoimmune disease are all herein fully incorporated by reference.

NFκB i. Activation

Rather than treating defects in proteolytic processing at the stage of the proteolytic processing, it is possible to target treatment according to the invention at the restoration of an important downstream target of proteasome activation, the transcription factor, NFκB and/or its downstream targets.

NFκB is a heterodimeric transcription factor composed of 50- and 65 kD subunits that belong to the rel family; it is present with inhibitory factor IκB in the cytoplasm of most cells (Baeuerle and Henkel, 1994, *Ann. Rev. Immunol.,* 12: 141–179; Verma et al., 1995, *Genes Dev.,* 9; 2723–2735). This transcription factor is responsive to cell surface cytokines, such as tumor necrosis factor α, interleukin-1 and cytoplasmic activation of this factor is required prior to nuclear localization. NFκB plays an active role in lymphocytic development and in cell survival (Wang et al., 1996, *Science,* 274: 784–787; Beg and Baltimore, 1996, *Science,* 274: 782–784; Van Antwerp et al., 1996, *Science,* 274: 787–789; Arsura et al., 1997, *Cell Growth Differ.,* 8: 1049–1059; Liu et al., 1996, *Cell,* 87: 565–576). In B cells, NFκB is constitutively expressed (Wu et al., 1996, *EMBO J.,* 15: 4682–4690). Knock-out mice missing RelA (p65) die before birth, in part, due to a described developmental defect of the immune system (macrophages, B and T cells) and massive death of liver cells (Arsura et al., 1997, supra; Beg et al., 1995, *Nature,* 376: 167–170; Bargou et al., 1997, *J. Clin. Invest.,* 100: 2961–2969). In vitro inhibition of NFκB induces similar developmental arrest and death of B cells (Liu et al., 1996, supra).

In the NFκB pathway, it has been observed that phosphorylation and ubiquitination work in concert to transmit a message to the nucleus and to activate the cell-cycle genes and proteins in the cytoplasm, thus activating cell signalling, division, development (e.g., differentiation) and proliferation; stimulating the the human epithelial HeLa cell line with TNF-α switches on a stress-activated MAP (mitogen-activated protein) cascade that promotes the phosphorylation of IκBA kinase (Lee et al., 1997, *Cell,* 88: 213–222). The kinase, in turn, phosphorylates the NFκB inhibitor protein IαBκ marking it for ubiquitination. In unstimulated cells, IκB binds to- and inhibits the activity of NFκB. When ubiquitinated IκB is degraded by the proteasome, NFκB translocates to the nucleus where it activates transcription. As is stated in Hopkin (1997, supra), the combination of two highly specific processes, phosphorylation and ubiquitination, has been utilized by cells to control complex signal-transduction pathways precisely. Such a mechanism which allows for a rapid return to normal is critical in the activation and de-activation of molecules such as cytokines, which are said to act transiently, as constitutive activation would be cytotoxic.

Cell surface signals on lymphocytes activate NFκB through cascades of kinases (Verma et al., 1995, supra; Baeuerle and Baltimore, 1996, *Cell,* 87: 13–20). A previous report shows a possible association of NF-κB with a cellular serine kinase, resulting phosphorylation and activation of NF-κB (Ostrowski et al., 1991, *J. Biol. Chem.,* 266: 12722–12733; Hayashi et al., 1993, *J. Biol. Chem.,* 268: 26790–26795). NFκB also can interact with cyclin dependent kinases (Cdk), phosphorylation steps regulating cell cycle progression and conveyance of signals for differentiation and apoptosis. Specifically, Cdk8 or Cdk7 (in combination with cyclins) coordinate the metabolism of differentiated cells with extracellular stimuli and regulate transcriptional activation.

ii. Activity in the Nucleus

NFκB and other members of the rel family of protein complexes play a central role in the transcriptional regulation of a remarkably diverse set of genes involved in the immune and inflammatory responses (Grilli et al., 1993, *Int.*

J. Cytology, 143: 1–62). For example, NFκB is required for the expression of a number of immune response genes, the Ig-κ light chain immunoglobulin gene, the IL-2 receptor α chain gene, the T cell receptor β chain gene, and class I and II major histocompatibility genes. In addition, NFκB has been shown to be required for a number of genes involved in the inflammatory response, such as the TNF-α gene and the cell adhesion genes, E-selectin, I-cam, and V-cam. NFκB is also required for the expression of a large number of cytokine genes such as IL-2, IL-6, G-CSF, and IFN-β. Finally, NFκB is essential for the expression of the human immunodeficiency virus (HIV).

iii. Role in the Cytoplasm

In addition to its role as a transcription factor, NFκB is believed mediate events occurring in the cytoplasm. Subunit p65 binds cyclin-dependent kinases (cdk's), cdc's and other cell cycle activators, which are part of a multiprotein complex; the data presented in Example 1, below, demonstrates such binding. These proteins control the cell cycle, differentiation, DNA replication and cell proliferation. It is thought that p50 may have similar binding affinities.

iv. Role in Autoimmune Disease

Developmental arrest of lymphocytes has been observed in humans with type I diabetes; such an arrest often manifests itself as an increase in the number of CD45RA-naive cells (Faustman et al., 1989, Diabetes 38: 1462–1468; Faustman, 1993, Diabete Metab. 19: 446–457; Faustman et al., 1990, J. Autoimmunity, 3: 111–116; Faustman et al., 1991, Diabetes, 40: 590–597). Functional assays of antigen presentation and analysis of surface antigens on lymphocytes have confirmed the existence of diverse and immature lineages of lymphocytes in type I diabetics (Faustman et al., 1991, Science, 254: 1756–1761; Peakman et al., 1993, Lancet, 342: 1296; Peakman et al., 1994, Lancet, 343: 424; Peakman et al., 1994, Diabetes, 43: 712–717).

Regardless of the level at which an autoimmune disease is treated according to the methods of the invention, it is necessary to deliver therapeutic agents in a safe and medically expedient manner. Gene therapy provides one set of methods by which bioactive substances, such as proteins and nucleic acids, may be delivered in active form to- or synthesized at their intended sites of action. Gene therapy methods are discussed in the following section.

Gene Therapy According to the Invention i. Therapeutic Nucleic Acids

Sequences

A therapeutic gene may be transfected for use in the invention using a viral or non-viral DNA or RNA vector, where non-viral vectors include, but are not limited to, plasmids, linear nucleic acid molecules, artificial chromomosomes and episomal vectors. Expression of heterologous genes has been observed after injection of plasmid DNA into muscle (Wolff J. A. et al., 1990, Science, 247: 1465–1468; Carson D. A. et al., U.S. Pat. No. 5,580,859), thyroid (Sykes et al., 1994, Human Gene Ther., 5: 837–844), melanoma (Vile et al., 1993, Cancer Res., 53: 962–967), skin (Hengge et al., 1995, Nature Genet., 10: 161–166), liver (Hickman et al., 1994, Human Gene Therapy, 5: 1477–1483) and after exposure of airway epithelium (Meyer et al., 1995, Gene Therapy, 2: 450–460).

Therapeutic nucleic acid sequences useful according to the methods of the invention include those encoding receptors, enzymes, ligands, regulatory factors, and structural proteins. Therapeutic nucleic acid sequences also include sequences encoding nuclear proteins, cytoplasmic proteins, mitochondrial proteins, secreted proteins, plasmalemma-associated proteins, serum proteins, viral antigens, bacterial antigens, protozoal antigens and parasitic antigens. Therapeutic nucleic acid sequences useful according to the invention also include sequences encoding proteins, lipoproteins, glycoproteins, phosphoproteins and nucleic acids (e.g., RNAs such as ribozymes or antisense nucleic acids). Proteins or polypeptides which can be expressed using the methods of the present invention include hormones, growth factors, neurotransmitters, enzymes, clotting factors, apolipoproteins, receptors, drugs, oncogenes, tumor antigens, tumor suppressors, structural proteins, viral antigens, parasitic antigens and bacterial antigens. The compounds which can be incorporated are only limited by the availability of the nucleic acid sequence encoding a given protein or polypeptide. One skilled in the art will readily recognize that as more proteins and polypeptides become identified, their corresponding genes can be cloned into the gene expression vector(s) of choice, administered to a tissue of a recipient organism, such as a mammalian tissue (including human tissue), and expressed in that tissue.

Therapeutic sequences according to the invention may encode products which restore proteasome activity; such genes are referred to as being 'upstream' of NFκB. For example, gene expression constructs encoding proteasome components or associated proteins (e.g. the Lmp2/Tap1 gene pair, or Lmp2, Lmp7, Tap1 or Tap2) comprising cDNA sequences functionally linked to the corresponding wild-type transcriptional regulatory sequences are of use. Genes which restore proper ubiquitination include those encoding members of the superfamily of ubiquitination-mediating enzymes of the classes E1, E2 and E3; as stated above, human homologues of the yeast ubiquitination enzymes have been discovered, among them the UbcH5 (which functions as an E2) and the MDM2 oncoprotein, which acts as a ubiquitin ligase, or E3 (see Honda et al., 1997, supra).

Sequences encoding wild-type NFκB subunits for use in the reconstitution of missing activity resulting from inactivating mutations in either or both of p65 and p50; genes encoding these proteins may be administered according to the invention. Genes which might compensate for a loss of proteasome function to activate NFκB by removing the need for proteasome-mediated cleavage of IκB are also of use, for example, a recombinant NFκB cDNA engineered such that its product can no longer be bound by IκB, as discussed above.

Other genes requiring activation by the proteasome encode apolipoprotein B100 (apoB), transcription factors, e.g. STAT transcription factor or DNA repair factor TFIIH, are also of use.

Genes downstream of NFκB (i.e. those which are under NFκB transcriptional control) may, themselves be expressed as cDNA constructs in a recipient host; however, this requires a knowledge of all downstream activation targets of NFκB in cells which are to receive treatment, as well as designing individual expression constructs for each such gene and ensuring that they are expressed in the proper ratios relative to one another an to other cellular proteins. As stated above, such genes include, but are not limited to, those which encode the Ig-κ light chain immunoglobulin, the IL-2 receptor α chain, the T cell receptor β chain, class I and II major histocompatibility proteins, TNF-α, E-selectin, I-cam, and V-cam, IL-2, IL-6, G-CSF, and IFN-β.

Nucleic acids of use in the invention include those that encode proteins for which a patient might be deficient or that might be clinically effective in higher-than-normal concentration as well as those that are designed to eliminate the translation of unwanted proteins. As discussed above, nucleic acids of use according to the invention for the elimination of deleterious proteins are antisense RNA and ribozymes, as well as DNA expression constructs that encode them. Note that antisense RNA molecules, ribozymes or genes encoding them may be administered to a patient by a method of nucleic acid delivery that is known in the art, such as an in vivo or an ex vivo method, as described below.

Therapeutic genes of use in the invention include those whose products may suppress the function of inhibitors or other negative regulators of proteasome function. One such regulator is the 40 kD-, ATP-dependent protein mentioned above whose release from the proteasome complex permits proteolytic cleavage of target proteins to occur. Inactivating nucleic acid sequences such may encode a ribozyme or antisense RNA specific for the mRNA which encodes the 40 kD protein or, alternatively, may encode an antibody directed against the 40 kD protein or a polypeptide of like sequence with the site on the proteasome complex to which the 40 kD protein binds in vivo; such a polypeptide could, if present at several-fold molar excess (e.g. 10-fold or more) over the endogenous proteasome component bound by the 40 kD species, serve as to compete the inhibitory protein off of it. Note that the 40 kD proteasome regulator is said to exist as a 250 kD multimer when released (see again WO 95/25533). Japanese patent JP 95121484 discloses a non-functional mutant of this protein which may be of use to titrate functional 40 kD molecules away from the proteasome complex.

In addition to the need to suppress the activity of inhibitors of proteasome function, it may be equally necessary to suppress that of proteins normally targeted for inactivation by the proteasome. These include oncogene c-Fos, ornithine decarboxylase, tyrosine aminotransferase, c-myb, HMG-R (a key enzyme of sterol synthesis) and apoB (also activated by proteasomes).

Successful methods for the therapeutic administration of antibodies for the treatment of autoimmune disease (in this case, rheumatoid arthritis) have been disclosed in U.S. Pat. No. 5,698,195, the contents of which are herein incorporated by reference.

Ribozymes of the hammerhead class are the smallest known, and lend themselves both to in vitro synthesis and delivery to cells (summarized by Sullivan, 1994, *J. Invest. Dermatol.*, 103: 85S–98S; Usman et al., 1996, *Curr. Opin. Struct. Biol.*, 6: 527–533).

Physical Properties and Delivery Vehicles

A nucleic acid of use according to the methods of the invention may be either double- or single stranded and either naked or associated with protein, carbohydrate, proteoglycan and/or lipid or other molecules. Such vectors may contain modified and/or unmodified nucleotides or ribonucleotides. Examples of some therapeutic nucleic acid sequences are enumerated above. In the event that the gene to be transfected is without its native transcriptional regulatory sequences, the vector must provide such sequences to the gene, so that it can be expressed once inside the target cell. Such sequences may direct transcription in a tissue-specific manner, thereby limiting expression of the gene to its target cell population, even if it is taken up by other surrounding cells. Alternatively, such sequences may be general regulators of transcription, such as those that regulate housekeeping genes, which will allow for expression of the transfected gene in more than one cell type; this assumes that the majority of vector molecules will associate preferentially with the cells of the tissue into which they were injected, and that leakage of the vector into other cell types will not be significantly deleterious to the recipient mammal. It is also possible to design a vector that will express the gene of choice in the target cells at a specific time, by using an inducible promoter, which will not direct transcription unless a specific stimulus, such as heat shock, is applied.

Delivery of a nucleic acid may be performed using a delivery technique selected from the group that includes, but is not limited to, the use of viral vectors and non-viral vectors, such as episomal vectors, artificial chromosomes, liposomes, cationic peptides, tissue-specific cell transfection and transplantation, administration of genes in general vectors with tissue-specific promoters, etc.

ii. Dosage

Generally, nucleic acid molecules are administered in a manner compatible with the dosage formulation, and in such amount as will be prophylactically and/or therapeutically effective. When the end product (e.g. an antisense RNA molecule or ribozyme) is administered directly, the dosage to be administered is directly proportional to the the amount needed per cell and the number of cells to be transfected, with a correction factor for the efficiency of uptake of the molecules. In cases in which a gene must be expressed from the nucleic acid molecules, the strength of the associated transcriptional regulatory sequences also must be considered in calculating the number of nucleic acid molecules per target cell that will result in adequate levels of the encoded product. Suitable dosage ranges are on the order of, where a gene expression construct is administered, 0.5–to 1 $\mu$g, or 1–100 $\mu$g, or optionally 10–100 $\mu$g of nucleic acid in a single dose. It is conceivable that dosages of up to 1 mg may be advantageously used. Note that the number of molar equivalents per cell vary with the size of the construct, and that absolute amounts of DNA used should be adjusted accordingly to ensure adequate gene copy number when large constructs are injected.

iii. Administration

Nucleic acid molecules to be administered according to the invention also may be formulated in a physiologically acceptable diluent such as water, phosphate buffered saline, or saline, and further may include an adjuvant. Adjuvants such as incomplete Freund's adjuvant, aluminum phosphate, aluminum hydroxide, or alum are materials well known in the art. Administration of a nucleic acid molecule as described herein may be either localized or systemic.

Localized Adminstration

It is contemplated that global administration of a therapeutic composition to an animal is not needed in order to achieve a highly localized effect. Localized administration of a nucleic acid is preferably by via injection or by means of a drip device, drug pump or drug-saturated solid matrix from which the nucleic acid can diffuse implanted at the target site. When a tissue that is the target of treatment according to the invention is on a surface of an organism, topical administration of a pharmaceutical composition is possible. For example, antibiotics are commonly applied directly to surface wounds as an alternative to oral or intravenous administration, which methods necessitate a much higher absolute dosage in order to counter the effect of systemic dilution, resulting both in possible side-effects in otherwise unaffected tissues and in increased cost.

Compositions comprising a therapeutic composition which are suitable for topical administration can take one of several physical forms, as summarized below:

(i) A liquid, such as a tincture or lotion, which may be applied by pouring, dropping or "painting" (i.e. spreading manually or with a brush or other applicator such as a spatula) or injection.

(ii) An ointment or cream, which may be spread either manually or with a brush or other applicator (e.g. a spatula), or may be extruded through a nozzle or other small opening from a container such as a collapsible tube.

(iii) A dry powder, which may be shaken or sifted onto the target tissue or, alternatively, applied as a nebulized spray.

(iv) An liquid-based aerosol, which may be dispensed from a container selected from the group that comprises pressure-driven spray bottles (such as are activated by squeezing), natural atomizers (or "pump-spray" bottles that work without a compressed propellant) or pressurized canisters.

(v) A carbowax or glycerin preparation, such as a suppository, which may be used for rectal or vaginal administration of a therapeutic composition.

In a specialized instance, the tissue to which a therapeutic composition is the lung. In such a case the route of administration is via inhalation, either of a liquid aerosol or of a nebulized powder of. Drug delivery by inhalation, whether for topical or systemic distribution, is well known in the art for the treatment of asthma, bronchitis and anaphylaxis. In particular, it has been demonstrated that it is possible to deliver a protein via aerosol inhalation such that it retains its native activity in vivo (see Hubbard et al., 1989, *J. Clin. Invest.*, 84: 1349–1354).

Note that in some cases, the surface in question is internal, for example, the gastric lining; in such a case, topical application would comprise taking the therapeutic composition via an oral route, whether in liquid, gel or solid form.

Systemic Administration

Systemic administration of a nucleic acid or other therapeutic composition according to the invention may be performed by methods of whole-body drug delivery are well known in the art. These include, but are not limited to, intravenous drip or injection, subcutaneous, intramuscular, intraperitoneal, intracranial and spinal injection, ingestion via the oral route, inhalation, trans-epithelial diffusion (such as via a drug-impregnated, adhesive patch) or by the use of an implantable, time-release drug delivery device, which may comprise a reservoir of exogenously-produced nucleic acid or other material or may, instead, comprise cells that produce and secrete a therapeutic protein or other agent (see "Ex vivo therapy", below). Note that injection may be performed either by conventional means (i.e. using a hypodermic needle) or by hypospray (see Clarke and Woodland, 1975, *Rheumatol. Rehabil.*, 14: 47–49).

Systemic administration is advantageous when a pharmaceutical composition must be delivered to a target tissue that is widely-dispersed, inaccessible to direct contact or, while accessible to topical or other localized application, is resident in an environment (such as the digestive tract) wherein the native activity of the nucleic acid or other agent might be compromised, e.g. by digestive enzymes or extremes of pH.

Nucleic acid constructs of use in the invention can be given in a single- or multiple dose. A multiple dose schedule is one in which a primary course of administration can include 1–10 separate doses, followed by other doses given at subsequent time intervals required to maintain and or reinforce the cellular level of the transfected nucleic acid. Such intervals are dependent on the continued need of the recipient for the therapeutic nucleic acid, the ability of a given nucleic acid to self-replicate in a mammalian cell if it does not become integrated into the recipient's genome and the half-life of a non-renewable nucleic acid (e.g. a molecule that will not self-replicate). Preferably, when the medical needs of the recipient mammal dictate that a nucleic acid or a product thereof will be required throughout its lifetime, or at least over an extended period of time, such as a year or more, a nucleic acid may be encoded by sequences of a vector that will self-replicate in the target cells. The efficacy of transfection and subsequent maintenance of the nucleic acid molecules may be assayed either by monitoring the activity of a marker gene, which may additionally be comprised by the transfected construct, or by the direct measurement of either the protein product encoded by the gene of interest or the reduction in the levels of a protein the production of which it is designed to inhibit. The assays can be performed using conventional molecular and biochemical techniques, such as are known to one skilled in the art.

Ex vivo Therapy

As alluded to earlier, it is possible to administer a therapeutic nucleic acid for use not only in in vivo therapy (i.e., that in which a nucleic acid is administered directly to a patient for uptake by- and subsequent expression in cells in situ) but also in ex vivo therapy (i.e., that in which a nucleic acid is administered to cultured or explanted cells in vitro, which transfected cells are subsequently transplanted into the clinical patient in order to supply a therapeutic product). Methods of ex vivo gene therapy are described in detail herein. By these methods, a plasmid which continues to be maintained in a transformed or transfected cell after such a cell has been administered (e.g. via transplantation) to a multicellular host, such as a mammal, delivers a gene product to that individual. It is contemplated that a gene of interest, particularly a therapeutic gene, will be expressed by the transplanted cell, thereby providing the recipient organism, particularly a human, with a needed RNA (e.g., an antisense RNA or ribozyme) or protein.

As discussed above, a cell type may be used according to the invention which is amenable to methods of nucleic acid transfection such as are known in the art. Such cells may include cells of an organism of the same species as the recipient organism, or even cells harvested from the recipient organism itself for ex vivo nucleic acid transfection prior to re-introduction. Such autologous cell transplants are known in the art. One common example is that of bone marrow transplantation, in which bone marrow is drawn either from a donor or from a clinical patient (for example, one who is about to receive a cytotoxic treatment, such as high doses of ionizing radiation), and then transplanted into the patient via injection, whereupon the cells re-colonize bones and other organs of the hematopoietic system.

a. Cell Dosage

The number of transfected cells which are administered to a recipient organism is determined by dividing the absolute amount of therapeutic or other gene product required by the organism by the average amount of such an agent which is produced by a transfected cell. Note that steady-state plasmid copy number varies depending on the strength of its origin of replication as well as factors determined by the host cell environment, the availability of nucleotides and replicative enzyme complexes, as does the level of expression of the gene of interest encompassed by the plasmid, which level likewise is determined by the strength of its associated promoter and the availability of nucleotides and transcription factors in a given host cell background. As a result, the level of expression per cell of a given gene of interest must be determined empirically prior to administration of cells to a recipient.

While efficient methods of cell transfection and transplantation are known in the art, they do not ensure that the transfected cell is immortal. In addition, the requirements of the recipient organism for the product encoded by the transgene may change over time. In light of these considerations, it is contemplated that cells may be administered in a single dose or in multiple doses, as needed. A multiple dose schedule is one in which a primary course of administration can include 1–10 separate doses, followed by other doses given at subsequent time intervals required to maintain and or reinforce the cellular level of the transfected nucleic acid. Such intervals are dependent on the continued need of the recipient for the therapeutic gene product. Preferably, when the medical needs of the recipient mammal dictate that a gene product will be required throughout its lifetime, or at least over an extended period of time, such as a year or more, the transfected cells will be replenished on a regular schedule, such as monthly or semi-monthly, unless such cells are able to colonize the recipient patient in permanent fashion, such as is true in the case of a successful bone-marrow cell transplant.

b. Nucleic Acid Dosage

Provided a nucleic acid vector capable of replication in the transfected cell is used, the absolute amount of nucleic acid which is transfected into cells prior to transplantation is not critical, since in cells receiving at least one copy of such a vector, the vector will replicate until an equilibrium copy-number is achieved. As a first approximation, an amount of vector equivalent to between 1 and 10 copies thereof per cell to be transfected may be used; one of skill in the art may adjust the ratio of plasmid molecules to cells as is necessary to optimize vector uptake. Of particular used in the invention are vectors or transfection techniques which result in the stable integration of the gene of interest into the chromosome of the transfected cell, so as to avoid the need to maintain selection for cells bearing the vector following transplantation into a recipient multicellular organism, such as a human.

c. Administration of Autologous or Syngeneic Cells

A cell type which is commonly transplanted between individuals of a single species (or, even, from an individual to a cell culture system and back to the same individual) is that of hematopoietic stem cells (HSCs), which are found in bone marrow; such cells have the advantage that they are amenable to nucleic acid transfection while in culture, and are, therefore, well suited for use in the invention. Cultures of HSCs are transfected with a minimal plasmid comprising an operator sequence and a gene of interest and the transfected cells administered to a recipient mammal in need of the product of this gene. Transfection of hematopoietic stem cells is described in Mannion-Henderson et al., 1995, *Exp. Hematol.*, 23: 1628; Schiffmann et al., 1995, *Blood*, 86: 1218; Williams, 1990, *Bone Marrow Transplant*, 5: 141; Boggs, 1990, *Int. J. Cell Cloning*, 8: 80; Martensson et al., 1987, *Eur. J. Immunol.*, 17: 1499; Okabe et al., 1992, *Eur. J. Immunol.*, 22: 37–43; and Banerji et al., 1983, *Cell*, 33: 729. Such methods may advantageously be used according to the present invention. Administration of transfected cells proceeds according to methods established for that of non-transfected cells, as described below.

The transplantation of hematopoietic cells, such as in a bone marrow transplant, is commonly performed in the art by procedures such as those described by Thomas et al. (1975, *New England J. Med.*, 292: 832–843) and modifications thereof. Such a procedure is briefly summarized: In the case of a syngeneic graft or of a patient suffering from an immunological deficiency, no immunosuppressive pre-treatment regiment is required; however, in cases in which a cells of a non-self donor are to be administered to a patient with a responsive immune system, an immunosuppressive drug must be administered, e.g. cyclophosphamide (50 mg/kg body weight on each of four days, with the last does followed 36 hours later by the transplant). Leukemic patients routinely receive a 1000-rad midline dose of total-body irradiation in order to ablate cancerous blood cells; this irradiation also has an immune-suppressive effect. Following pre-treatment, bone marrow cells (which population comprises a small number of pluripotent hematopoietic stem cells, or HSCs), are administered via injection, after which point they colonize the hematopoietic system of the recipient host. Success of the graft is measured by monitoring the re-appearance of the numerous adult blood cell types by the immunological and molecular methods which are well known in the art. While as few as 1–10 HSCs are, in theory, able to colonize and repopulate a lethally-irradiated recipient mammal over time, it is advantageous to optimize the rate at which repopulation occurs in a human bone marrow transplant patient; therefore, a transplanted bone marrow sample comprising 10 to 100, or even 100 to 1000 HSCs should be administered in order to be therapeutically effective.

It is contemplated that both lymphoid and parenchymal cells, particularly those which are targeted for destruction in autoimmune disease, are of use in the invention. Such parenchymal include those of the islets of Langerhans, the thyroid, the adrenal cortex, muscles, cartilagenousor other synovial tissue, the kidneys, epithelial tissues (both external and internal, particularly that of the intestinal lumen, lung, heart, liver, kidney, neurons and synovial cells) and the nervous system.

In that such cells are meant to either to replace those lost to autoimmune destruction or to provide a pool of autoimmune-resistant cells prior to massive cell death, it is necessary to ensure that such cells indeed are not susceptible to autoimmune disease. Provided that early treatment is undertaken, it is possible to harvest small (or, in some cases, large) numbers of cells of the target tissue directly from the patient for transfection and reintroduction; alternatively, cells of a donor of matching tissue type may be used.

To render the transplanted cells resistant, at least collectively, to immune rejection by the recipient organism, it is contemplated that transplanted cells expressing a high level of activated NFκB (a high NFκB "set point"), while still subject to destruction by autoimmune host lymphocytes, would enjoy the advantage of robust proliferative capacity in order to multiply at a rate surpassing that of cell killing, thereby providing a long-lived population of therapeutic cells to the recipient organism. Such cells may be transfected with gene expression constructs which result in the production of high levels of activated NFκB, or may be cells obtained from a donor selected for high endogenous NFκB activity, as may be determined in an in vitro transcription assay or DNA/protein binding assay (as described in Example 2, below) using protein extracts drawn from such a donor, which may, itself, be a transgenic mammal.

As an alternative, a procedure has been developed which allows for the shielding of transplanted cells, even those transplanted from a members of one species to another (see also below, for other such methods). As a protective measure against viral infection, a mechanism has evolved in the immune system of vertebrates in which viral proteins being produced within the infected cells are broken down into peptides by intracellular proteolytic enzymes. Some of the peptides are enfolded by a particular class (Class I) of proteins of the major histocompatibility complex (MHC) of genes and are transported to the cell surface, where the viral peptide/MHC protein complex is displayed as a surface antigen. Circulating cytotoxic T lymphocytes (CTLs) having the appropriate specificity recognize the displayed MHC Class I antigen as foreign and proceed, through activation and a complex lytic cascade, to kill the infected cell. The MHC Class I proteins are expressed in essentially all nucleated cells of the body and are a key element in the immune system's ability to distinguish between "self" molecules and "foreign" (non-self) molecules. They can be distinguished from the other class of proteins of the major histocompatibility complex of genes, known as MHC Class II proteins.

Although MHC Class I antigens are a magnificent mechanism for combating infection, they also are primarily responsible for the failure of tissues, e.g., cells, organs, or parts of organs, that are transplanted from one mammal (donor) to another (host). This rejection of tissue by the host organism was first observed in mouse skin graft experiments in the 1950s and was named the transplant reaction. The search for the factor on donor cells that was evidently recognized and attacked by the host's immune system led finally to the characterization of the two classes of MHC proteins (see, Snell, 1957, *Ann Rev. Microbiol.,* 2: 439–57).

Recognition of donor MHC Class I antigens as foreign by host CTLs occurs not only where the donor tissue is different from a different species (a xenogeneic transplant) but also where the tissues are from a donor of the same species as the host (an allogeneic transplant). The specificity of the T cell receptors on CTLs and other T cells that bind to Class I and Class II antigens is such that a single amino acid difference in the structure of a MHC antigen can be detected as foreign, leading to an immune response. The MHC proteins are expressed from DNA formed by rearrangement of several gene segments in the MHC loci, leading to a high degree of polymorphism in MHC proteins.

A method applicable to inhibiting the rejection of transplanted tissues mediated by recognition of MHC class I antigens is as follows: Transplanted allogeneic or xenogeneic tissue comprising treating the transplant tissue with an enzyme capable of cleaving MHC Class I antigens. Removal of Class I antigens from the donor tissue attenuates the extent of the immune response mounted by the host mammal receiving the transplant. Furthermore, the enzyme treatment is an effective preparatory treatment for all tissues intended for transplant, without regard to the specific MHC antigens displayed on the donor tissue or the specificities of the immune system cells of the host.

The method of treating tissues to render them suitable for transplant comprises incubating the donor tissue with an enzyme capable of cleaving MHC Class I antigens, e.g., in an amount and for a sufficient period to remove sufficient MHC Class I antigens to significantly attenuate the host's immune response to the donor tissue. Such incubation is performed in a medium which allows both enzymatic cleavage of the surface antigens to proceed, but is still amenable to tissue survival (e.g. a physiological salt buffer, such as PBS, or a cell-, tissue- or organ culture medium, such as are known in the art. Typically the mean cell density of Class I antigens will be reduced below about 10% of untreated levels, preferably below 1%. One such useful enzyme is papain.

The enzyme selected for use in this method must be capable of cleaving MHC Class I antigens, that is, removing a MHC Class I protein/peptide complex from the surface of a cell on which it was displayed. Useful cleavage is that which alters the MHC Class I antigen as displayed sufficiently to avoid interaction with the immune system cells of the recipient mammal; the object of this cleavage step is to remove substantially all of the extracellular portion of the MHC Class I antigen from the cell. Any amount of MHC Class I antigen that can be removed from the donor tissue is helpful in avoiding rejection of the transplant; however, as a practical matter, removal of as much of the MHC Class I antigens as possible without killing the tissue is desired, e.g. a reduction in MHC Class I density of at least 90% or even as much as 99% is desirable.

Typically, this is accomplished by bathing the donor tissue in a solution of the enzyme for a period to allow the enzyme to react with the MHC proteins, e.g., from 20 minutes to 24 hours or more. At high enzyme concentration, incubation of tissues may be for even shorter periods, so long as the cells of the tissues are not damaged. In general, a minimum of 75% viability of the tissue cells is required, although 90% viability or more is sought. In order to retard resynthesis of the MHC class I molecules, the enzyme treatment is carried out at the optimal temperature for enzyme activity, but the treated tissue is thereafter maintained at a low temperature, for example at 4° C., until ready for use.

There are several advantages to the use of enzymes as a treatment for avoiding transplant rejection: (a) the enzymes are comparatively inexpensive, and many are commercially available in high purity with well-characterized activity and specificity; (b) enzymes can be used locally or in vitro to avoid systemic treatments; (c) enzyme shaving of the transplant tissue can be used in combination with (i.e., without foreclosing) other complementary therapies; and (d) the use of enzymes is not species-restricted or allelically restricted, and thus the method is adaptable to veterinary, human and xenogenic tissue treatment without radical modification of the procedures or reagents. Since the tissues will remain viable after treatment, expression of MHC molecules will continue, and eventually reappearance of MHC antigens on the donor tissue will occur, e.g., after transplantation; consequently, it is this method may be used as part of an overall therapy that may include additional measures to avoid rejection of the transplanted cells, such as immunosuppression, plasmaphoresis, antigen blocking, transfection, and the like. Although pre-transplantation treatment of the tissues will be the most common practice, it is also contemplated that this method of the present invention may be employed in situ to effect local immune response inhibition to preserve previously translated tissue. In such cases, cleavage of the surface antigen produces a local, soluble, competitive receptor for the cells of the host's immune system, which may serve to effectively blunt immune attack on the transplanted tissue.

Useful enzymes include proteolytic enzymes, gycosidases, proteinases and combinations of such enzymes that may sufficiently alter the surface antigens to inhibit subsequent transplant rejection. Examples include, but are not limited to, endoproteinase, pepsin, papain, chymotrypsin, trypsin, collagenase, cyanogen bromide, enterokinase (Asp or Glu-specific), iodosobenzoate, lysobacter endoproteinase, N-bromosuccinimide, N-chlorosuccinimide, hydroxylamine, 2-nitro-5-thiocyanobenzoate and endopeptidase. Papain particularly of use, as it is known to cut all MHC Class I molecules of different alleles and different species in the $\alpha 3$ domain. Papain does not cut the $\alpha 1$ or $\alpha 2$ domain.

Papain cutting characteristics are well described. Papain is the major ingredient of meat tenderizers and is sulfhydryl protease isolated from the latex green fruit of papaya. It was first isolated in 1955 and its enzymatic capabilities have been extensively documentated. In its native state, the enzyme is inactive, and therefore donor tissue treatments may be advantageously carried out with a high degree of control, using native papain in the presence of activators such as cysteine (0.005 M) and/or EDTA (0.002 M). See generally, Stockell et al., 1957, *J. Biol. Chem.*, 227: 1–26.

Additional such enzymatic reagents include, but are not limited to, oxidoreductases acting on: (1) OH—OH groups: (2) aldehyde or keto groups; (3) CH—CH groups; (4) CH—$NH_2$ groups; (5) reduced NAD or NADP; (6) nitrogenous compounds; (7) diphenols; (8) acting on $H_2O_2$; (9) hydrogen; (10) acting on single donors with incorporation of oxygen: and (11) acting on paired donors with incorporation of oxygen into one donor; tranferases: (1) transferring one-carbon groups (methyltranferases, hydroxymethyl-, formyl-and related transferases, carboxyl- and carbamoyltransferases, amidinotransferases); (2) transferring aldehydic or ketonic residues; (3) acting on acyltranferases, aminoacyltransferases); (4) acting on glycosyltranferases (hexosyltranferases, pentosyltranferases); (5) transferring alkyl or related groups; (6) transferring nitrogenous groups; (7) transferring phosphorus-containing groups (phosphotranferases with an alcohol group as acceptor, phosphotransferases with a carboxyl group as acceptor, phosphotranferases with a nitrogenous group as acceptor, phosphotransferases with a phosphate group as acceptor, phosphotransferases, pyrophosphotransferases, nucleotidyltransferases, transferases for other substituted phospho-groups); and, (8) transferring sulphur-containing groups (sulphurtransferases, sulphotransferases, CoA-transferases); hydrolases: (1) acting on ester bonds (carboxylic ester hydrolases, thiolester hydrolases, phosphoric monoester hydrolases, phosphoric diester hydrolases, triphosphoric monoester hydrolases, sulphuric ester hydrolases); (2) acting on glyeosyl compounds (glycoside hydrolases, hydrolysing N-glycosyl compounds, hydrolysing S-glycosal compounds); (3) acting on ether bonds (thioether hydrolases); (4) acting on peptide bonds (peptide hydrolases) (α-amino-acyl-peptide hydrolases, peptidyl-amino-acid hydrolases, dipetide hydrolases, peptidyl-peptide hydrolases); (5) acting on C—N bonds other than peptide bonds (in linear amides, in cylic amides, in linear amidines, in cylic amidines, in cyanides); (6) acting on acid-anhydride bonds (in phosphoryl-containing anhydrides); (7) acting on C=C bonds; (8) acting on carbon-halogen bonds; (9) acting on P—N; lyases (1) acting on carbon-carbon bonds (carboxyl-lyases, aldehyde-lyases, keto acid-lyases); (2) acting on carbon-oxygen bonds (hydrolyases and other carbon-oxygen lyases); (3) acting on carbon-nitrogen bonds (amonia-lyases and amidine-lyases); (4) carbon-sulphur lyases; (5) carbon-halogen lyases; (6) other lyases; isomerases: (1) racemases and epimerases (acting on amino acids and derivatives; acting on hydroxy-acids and derivatives, acting on carbohydrates and derivatives, acting on other compounds; (2) acting on cis-trans isomerases; (3) acting on intramolecular oxidoreductases (interoconverting aldoses and ketoses, interoconverting keto- and enol-groups, transposing C=C bonds); (4) acting on intramolecular transferases (transferring acyl groups, transferring phosphoryl groups, transferring other groups); (5) acting on intramolecular lyases; (6) other isomerases; ligases: (1) acting on forming C—O bonds (amino-acid-RNA ligases); (2) acting on forming C—N bonds (acid-ammonia ligases (amide synthetases), acid-amino-acid ligases (peptide synthetases), cyclo-ligases, other C—N ligases, C—N ligases with glutamine as N-donor); (3) forming C—C bonds; and glycosidases, such as α-mylase, β-amylase, glucoamylase, celulase, laminarinase, inulase, dextranase, chitinase, polygalacturonase, lysozyme, neuraminidase, α-glucosidase, β-glucosidase, α-galactosidase, β-galactosidase, α-mannosidase, β-fructofuranosidase, trehalase, chitobiase, β-acetylglucosaminidase, β-glucuronidase, dextrin-1,6-glucosidase, hyaluronidase, β-D-fucosidase, metalopeptidases, phospholiphase C and nucleosidase.

d. Administration of Xenogeneic and Allogeneic Cells

While transfection and subsequent transplantation of cells which are obtained from an individual or cell culture system of like species with the recipient organism may be performed, it is equally true that the invention may be practised using cells of another organism (such as a well-characterized eukaryotic microorganism, e.g. yeast, in which appropriate processing of proteins encoded by therapeutic genes is likely and in which useful origins of replication are known). In such a case, certain concerns must be addressed.

First, when a protein is encoded by the gene of interest, the transplanted cells must produce the protein in a form that may is of use to the recipient organism. Post-translational processing (including, but not limited to, cleavage and patterns of glycosylation) must be consistent with proper function in the recipient. In addition, either a protein or an RNA molecule of interest must be made available to the recipient after synthesis, such as by secretion, excretion or exocytosis from the transplanted cell. To address the former, the protein produced by the transfected cells may be qualitatively compared to the native protein produced by an individual of the same species as the recipient organism by biochemical methods well known in the art of protein chemistry. The latter, release of the protein of interest by the cells to be transplanted, may be assayed by isolating protein from culture medium which has been decanted from the transfected cells or from which such cells have been separated (i.e. by centrifugation or filtration), and performing Western analysis using an antibody directed at the protein of interest. Antibodies against many proteins are commercially available; techniques for the production of antibody molecules are well known in the art.

Second, the cells must be shielded from immune rejection by the recipient organism. It is contemplated that such cells may be transfected with constructs expressing cell-surface markers (e.g. MHC antigens) characteristic of the recipient patient so as to provide them with biochemical camoflage.

In addition, methods for the encapsulation of living cultures of cells for growth either in an artificial growth environment, such as in a fermentor, or in a recipient organism have been developed, and are also of use in the administration of cells transfected according to the invention. Such an encapsulation system renders the cell invisible to immune detection and, in addition, allows for the free exchange of materials (e.g. the gene product of interest, oxygen, nutrients and waste materials) between the transplanted cells and the environment of the host organism.

Methods and devices for cell encapsulation are disclosed in numerous U.S. Patents; among these are U.S. Pat. Nos. 4,353,888; 4,409,311; 4,673,566; 4,744,933; 4,798,786; 4,803,168; 4,892,538; 5,011,472; 5,158,881; 5,182,111; 5,283,187; 5,474,547; 5,498,401 (which is particularly directed to the encapsulation of bacterial and yeast cells in chitosan); U.S. Pat. Nos. 5,550,050; 5,573,934; 5,578,314; 5,620,883; 5,626,561; 5,653,687; 5,686,115; 5,693,513; and 5,698,413, the contents of which are fully incorporated by reference herein. Typically required for the successful culture of encapsulated cells is a selectively-permeable outer covering or 'skin' which is biocompatible (i.e., tolerated by both the encapsulated cells and the recipient host), and, optionally, a matrix in- or upon which cells are distributed such that the matrix provides structural support and a substrate to which anchorage-dependent cells may attach themselves. As relates to encapsulation devices applicable to use in the invention, the term "selectively-permeable" refers to materials comprising openings through which small molecules (including molecules of up to about 50,000 M.W.–100,000 M.W.) may pass, but from which larger molecules, such as antibodies (approximately 150,000 M.W.), are excluded. Suitable covering materials include, but are not limited to, porous and/or polymeric materials such as polyaspartate, polyglutamate, polyacrylates (e.g., acrylic copolymers or RL®, Monsanto Corporation), polyvinylidene fluoride, polyvinylidienes, polyvinyl chloride, polyurethanes, polyurethane isocyanates, polystyrenes, polyamides, cellulose-based polymers (e.g. cellulose acetates and cellulose nitrates), polymethyl-acrylate, polyalginate, polysulfones, polyvinyl alcohols, polyethylene oxide, polyacrylonitriles and derivatives, copolymers and/or mixtures thereof, stretched polytetrafluoroethylene (U.S. Pat. Nos. 3,953,566 and 4,187,390, both incorporated herein by reference), stretched polypropylene, stretched polyethylene, porous polyvinylidene fluoride, woven or non-woven collections of fibers or yarns, such as "Angel Hair" (Anderson, *Science,* 246: 747–749; Thompson et al., 1989, *Proc. Natl. Acad. Sci. U.S.A.,* 86: 7928–7932), fibrous matrices (see U.S. Pat. No. 5,387,237, incorporated herein by reference), either alone or in combination, or silicon-oxygen-silicon matrices (U.S. Pat. No. 5,693,513). Polylysine having a molecular weight of 10,000 to 30,000, preferably 15,000 to 25,000 and most preferably 17,000 is also of use in the invention (see U.S. Pat. No. 4,673,566). Alternatively, the matrix material, comprising the transfected cells of the invention, is exposed to conditions that induce it to form its own outer covering, as discussed below.

As described in U.S. Pat. No. 5,626,561, the selective permeability of such a covering may be varied by impregnating the void spaces of a porous polymeric material (e.g., stretched polytetrafluoroethylene) with a hydrogel material. Hydrogel material can be impregnated in substantially all of the void spaces of a porous polymeric material or in only a portion of the void spaces. For example, by impregnating a porous polymeric material with a hydrogel material in a continuous band within the material adjacent to and/or along the interior surface of a porous polymeric material, the selective permeability of the material is varied sharply from an outer cross-sectional area of the material to an inner cross-sectional area of the material. The amount and composition of hydrogel material impregnated in a porous polyhmeric material depends in large part on the particular porous polymeric material used to encapsulate cells for transplant. Examples of suitable hydrogel materials include, but are not limited to, HYPAN® Structural Hydrogel (Hymedix International, Inc.; Dayton, N.J.), non-fibrogenic alginate, as taught by Dorian in PCT/US93/05461, which is incorporated herein by reference, agarose, alginic acid, carrageenan, collagen, gelatin, polyvinyl alcohol, poly(2-hydroxyethyl methacrylate), poly(Nvinyl-2-pyrrolidone) or gellan gum, either alone or in combination.

The matrix typically has a high surface-area:volume ratio, comprising pores or other spaces in- or on which cells may grow and through which fluids may pass; in addition, suitable matrix materials are stable following transplantation into a recipient organism. Preferably, the matrix comprises an aggregation of multiple particles, fibers or laminae. Alternatively, a matrix may comprise an aqueous solution, such as a physiological buffer or body fluid from the recipient organism (see U.S. Pat. No. 5,011,472). Suitable matrix materials include liquid, gelled, polymeric, co-polymeric or particulate formulations of aminated glucopolysachharides (e.g., deacetylated chitin, or "chitosan", which is prepared from the pulverized shells of crabs or other crustaceans, and is commercially available as a dry powder; Cat. # C 3646, Sigma, St. Louis, Mo.), alginate (U.S. Pat. No. 4,409,331), poly-$\beta$-1$\rightarrow$5-N-acetylglucosamine (p-GlcNAc) polysaccharide species (either alone of formulated as co-polymer with collagen; see U.S. Pat. No. No. 5,686,115), reconstituted extracellular matrix preparations (e.g. Matrigel®; Collaborative Research, Inc, Lexington, Mass.; Babensee et al., 1992, *J. Biomed. Matr. Res.,* 26: 1401), proteins, polyacrylamide, agarose and others.

Methods by which cells become encapsulated using such materials are both numerous and varied. Encapsulation devices comprising a semi-permeable membrane material, as described above, may be pre-formed, filled with cells (e.g. by injection or other manual means) and then sealed (U.S. Pat. Nos. 4,892,538; 5,011,472; 5,626,56; and 5,653,687); such sealing may be effectively permanent (e.g. by the use of heat-sealing), semi-permanent (e.g. by the use of a biocompatible adhesive, such as an epoxy, which will not dissolve or degrade in an aqueous environment) or temporary (e.g. by the use of a removable cap or plug, or by shutting of a valve or stopcock). Methods of permanent and semi-permanent sealing are disclosed in U.S. Pat. No. 5,653,687. As an alternative to the use of a pre-formed, semi-permeable cell reservoir, methods by which cells suspended in matrix material and the substance which is to form the outer covering of the encapsulation device are co-extruded under conditions which cause the cell/matrix mixture, which may be in liquid or semi-liquid (i.e., gelled) form to be encased in a continuous tube of the semi-permeable polymer, which either forms, or becomes crosslinked, under the extrusion conditions; such an extrusion procedure may lead to the formation of capsules which have only one cell reservoir (U.S. Pat. No. 5,283,187) or which are divided into multiple, discrete compartments (U.S. Pat. No. 5,158,881). As an alternative to both types of procedure, a liquid or semi-liquid (i.e., gelled) cell/matrix mixture droplet is suspended either in an agent which induces 'curing' or crosslinking of the outer layer of matrix material to form a semi-permeable barrier (U.S. Pat. Nos. 4,798,786 and 5,489,401) or in a solution of polymeric material (or monomers thereof), which will polymerize and/or crosslink upon contact with the cell/matrix droplet such that a semi-permeable membrane is deposited thereon (U.S. Pat. Nos. 4,353,888; 4,673,566; 4,744,933; 5,620,883; and 5,693,513).

One of skill in the art is well able to select the appropriate matrix and semi-permeable membrane materials and to construct a cell-encapsulation device as described above.

Implantation of such a device is achieved surgically, via standard techniques, to a site at or near the anatomical location to which the product encoded by the gene on the gene of interest is to be delivered, as is deemed safest and most expedient. Such a device may take a convenient shape, including, but not limited to, that of a sphere, pellet or other capsule shape, disk, rod or tube; often, the shape of the device is determined by its method of synthesis. For example, one which is formed by co-extrusion of a cell suspension and a polymeric covering material is typically tubular, while one formed by the deposition of a covering on droplets comprising cells in matrix material might be spherical. As discussed above, the number of cells which must be implanted (and, therefore, encapsulated) is dependent upon the requirements of the recipient organism for the product of the transfected gene. The encapsulation devices described above are typically small (most usefully, 10 μm to 1 mm in diameter, so as to permit efficient diffusion of substances back and forth between the outer covering and the cells most deeply embedded in the matrix), and it is contemplated that such devices may carry between 10 and $10^{10}$ cells each. Should the need for larger numbers of cells be anticipated, a plurality (2, 10 or even 100 or more) of such in vivo culturing devices may be made and implanted in a given recipient organism.

An encapsulated cell device may be intended for permanent installation; alternatively, retrieval of the device may be desirable, whether to terminate delivery of the product of the gene of interest to the recipient organism at the discretion of one of skill in the art, such as a physician (who must determine on a case-by-case basis the length of time for which a given cell implant is beneficial to the recipient organism) or to replenish the device with fresh cells after long-term use (i.e. months to years). To the latter end, an implantation device may usefully comprise a retrieval aid, such as a guidewire, and a cap or other port, such as may be opened and re-sealed in order to gain access to the cell reservoir, both as described in U.S. Pat. No. 4,892,538.

Live cultures of encapsulated cells have been used successfully to deliver gene products to tissues of a recipient animal. U.S. Pat. No. 4,673,566 discloses successful maintenance of normal blood sugar levels in a diabetic rat into which encapsulated rat islet of Langerhans cells were implanted; two administrations of 3,000 cells each together were effective for six months, while a single dose of 1,000 cells was effective for two months.

Encapsulated GABA-secreting pancreatic cells implanted into subthalamic nucleus of monkeys in whom Parkinsonism has been clinically-induced have been observed relieve the symptoms of that syndrome (U.S. Pat. No. 5,474,547), demonstrating invisibility of encapsulated cells to the immune system, as well as efficacy in delivering a product of encapsulated, transplanted cells to a recipient organism.

More encouraging, as it demonstrates immunological shielding by cell encapsulation systems sufficient for cross-species cell transplants, as is advantageous for their use in practicing the present invention, is the finding that encapsulated embryonic mouse mesencephalon cells, when transplanted into recipient rats, alleviate symptoms of clinically-induced Parkinsonism (U.S. Pat. No. 4,892,538).

Similarly, heterospecific transplantation of encapsulated islet cells has been demonstrated to treat diabetes successfully (dog islet cells to a mouse recipient, U.S. Pat. No. 5,578,314; porcine islet cells to a mouse recipient, Sun et al., 1992, *ASAIO J.*, 38: 124). It is believed that such an approach is promising for the clinical treatment of diabetes mellitus in humans (Calafiore, 1992, *ASAIO J.*, 38: 34).

It is contemplated that these techniques, which have been applied successfully to untransfected cells, may be utilized advantageously with cells that are transfected with therapeutic nucleic acid molecules of use in the invention.

e. Assay of Efficacy of Transplanted Cells in a Recipient Organism

The efficacy of the transfected cells so administered and their subsequent maintenance in the recipient host may be assayed either by monitoring the activity of a marker gene, which may additionally be comprised by the transfected construct, or by the direct measurement of either the product (e.g. a protein) encoded by the gene of interest or the reduction in the levels of a protein the production of which it (an antisense message or ribozyme) is designed to inhibit. The assays can be performed using conventional molecular and biochemical techniques, such as are known to one skilled in the art, or may comprise histological sampling (i.e., biopsy) and examination of tranplanted cells or organs.

In addition to direct measurements of protein or nucleic acid levels in blood or target tissues encoded by the gene of interest borne by the vector in transfected/transplanted cells, it is possible to monitor changes in the disease state in patients receiving gene transfer via transplantation of cells in which the gene of interest is maintained and compare them to the progression or persistence of disease in patients receiving comparable cells transfected with vector constructs lacking the gene of interest.

Proteins and Other Therapeutic Agents

In addition to nucleic acids, proteins and perhaps other bioactive substances may be used to stimulate proteosome activity in a recipient mammal. When the amount of a protein or other therapeutic agent to be used is considered, the lowest dose that provides the desired degree of enhancement of NFκB activity by the target cells should be used; lower doses may be advantageous in order to minimize the likelihood of possible adverse effects. Note that "NFκB activity" includes not only the presence of functional NFκB, but may also include the presence of the products of genes regulated by NFκB, regardless of the means by which they have arisen in the cell, as well as normal differentiation, proliferation and survival of the cell. It will be apparent to those of skill in the art that the therapeutically-effective amount of a composition administered in the invention will depend, inter alia, upon the efficiency of cellular uptake of a composition, the administration schedule, the unit dose administered, whether the compositions are administered in combination with other therapeutic agents, the health of the recipient, and the therapeutic activity of the particular protein or other pharmaceutical substance.

As is also true of nucleic acids administered according to the invention, the precise amount of a protein or other pharmaceutical agent required to be administered depends on the judgment of the practitioner and may be peculiar to each subject, within a limited range of values. An appropriate dose of a protein or other substance may be calculated as follows:

The NOD mouse model may be used to assay the effectiveness of varying doses of a protein or other agent in treating an autoimmune disease according to the invention. For a given therapeutic composition, it is necessary to establish an approximate range of dosages that are useful, yet relatively safe, in a clinical situation. The NOD mouse model may be employed to establish a dosage curve prior to use of the invention in human subjects. Alternatively, if a pharmaceutical agent useful according to the invention already has been granted regulatory approval, it stands that acceptable upper limits of dosage tolerance for humans and other mammals already will have been established for these drugs prior to testing, as have systemic concentrations useful for other clinical applications. These known dosages may serve as the basis upon which calculations may be made prior to use of the mouse model.

A therpeutic composition may be administered either systemically or locally. In the general case, a starting dosage to be administered locally to cells in the mice equals the optimal systemic concentration described for a known use of the therapeutic agent. Ideally, such a dosage has been established for mice; otherwise, the relevant human dosage is used for the purposes of calculation. As it is not known whether the concentration of a particular protein or other agent that is useful for enhancing NFκB activity is higher or lower than that used for other clinical purposes, a range of values above and below the recommended dosage may be assayed. In a first attempt, values spanning four orders of magnitude below this dosage are examined; if no effect is seen, or if enhancement of NFκB activity in the target cells is observed to increase at or near the starting dosage, values that exceed that dosage by up to four orders of magnitude are assayed. If no effect is seen within four orders of magnitude in either direction of the starting dosage, it is likely that the agent is not of use according to the invention. It is critical to note that when elevated dosages are used, the concentration must be kept below harmful levels, which are also known for all drugs that are approved for clinical use. Such a dosage should be one (or, preferably, two or more) orders of magnitude below the $LD_{50}$ value that is known for a laboratory mammal, whether or not that mammal is a mouse, and preferably below concentrations that are documented as producing serious, if non-lethal, side effects. If it determined that a therapeutic agent is optimally useful at levels that are harmful if achieved systemically, that agent should be used for local administration only, and then only at such doses where diffusion of the drug from the target site reduces its concentration to safe levels.

Assessment of Changes in Proteasome Activity According to the Invention

Methods for assessing proteasome activity following treatment are as described above for use in the detection of deficiencies in proteolytic processing.

Assessment of NFκB Activation According to the Invention

The amount of NFκB in cells treated according to the invention may be assessed by methods well known in the art, as described above for the detection of defects in proteolysis leading to the failure to activate NFκB.

Molecular Methods i. Northern Analysis

Molecular methods such as Northern analysis are well known in the art (see Sambrook et al., 1989, *Molecular Cloning. A Laboratory Manual.*, 2nd Edition, Cold Spring Harbor Laboratory Press, Cold Spring Harbor, N.Y.).

ii. RT-PCR

As an alternative to Northern analysis, reverse transcription/polymerase chain reaction (RT-PCR) may be performed. In the reverse transcription (RT) step of RT-PCR, the RNA is converted to first strand cDNA, which is relatively stable and is a suitable template for a PCR reaction. In the second step, the cDNA template of interest is amplified using PCR. This is accomplished by repeated rounds of annealing sequence-specific primers to either strand of the template and synthesizing new strands of complementary DNA from them using a thermostable DNA polymerase.

1 μg of total RNA and 75 pmol random hexamer primer (e.g., Pd(n)6, supplied by Pharmacia; Piscataway, N.J.) are resuspended in a 10 μl volume with DEPC-treated water in an RNase-free 0.5 μl tube. This mixture is incubated at 70° C. for 10 minutes and placed on ice for two minutes. The following reagents are added to the 10 μl reaction; 1 μl (200U) MMLV-RT (Superscript® reverse transcriptase, BRL, Life Technologies, Gaithersburg, Md.), 4 μl 5× reaction buffer (BRL, Life Technologies, Gaithersburg, Md.), 2 μl 0.1M DTT, 1 μl 10 mM dNTP and 1 μl human placental RNase inhibitor (10 to 50 units per μl; Boehringer Mannheim, Indianapolis, Ind.). In addition, for each RNA sample a second reaction is prepared except that MMLV-RT was omitted (RT negative control). The 19 μl reaction is incubated for 50 minutes at 42° C. in a programmable thermal cycler (such as is manufactured by MJ Research; Watertown, Mass.) and inactivated by heating to 90° C. for 5 minutes. After cooling to 37° C., 1 μl RNase H (3 units per μl; BRL, Life Technologies, Gaithersburg, Md.) is added, the reaction is incubated at 37° C. for 20 minutes, then cooled to 4° C. RNA integrity is confirmed by amplification of a transcript of a constitutively-expressed gene (e.g., interleukin-2 or $G_{\alpha s}$); therefore, it is ensured that a negative result subsequently observed on a test sample can be ascribed to a lack of that specific mRNA and not to degradation of the pool of mRNA or failure of the reverse transcription reaction.

The polymerase chain reaction, or PCR, is then performed as previously described (Mullis and Faloona, 1987, *Methods Enzymol.*, 155: 335–350, herein incorporated by reference). PCR, which uses multiple cycles of DNA replication catalyzed by a thermostable, DNA-dependent DNA polymerase to amplify the target sequence of interest, is well known in the art.

Oligonucleotide primers useful according to the invention are single-stranded DNA or RNA molecules that are hybridizable to a nucleic acid template to prime enzymatic synthesis of a second nucleic acid strand. The primer is complementary to a portion of a target molecule present in a pool of nucleic acid molecules used in the preparation of sets of arrays of the invention. It is contemplated that such a molecule is prepared by synthetic methods, either chemical or enzymatic. Alternatively, such a molecule or a fragment thereof is naturally-occurring, and is isolated from its natural source or purchased from a commercial supplier. Oligonucleotide primers are 15 to 100 nucleotides in length, ideally from 20 to 40 nucleotides, although oligonucleotides of different length are of use.

Typically, selective hybridization occurs when two nucleic acid sequences are substantially complementary (at least about 65% complementary over a stretch of at least 14 to 25 nucleotides, preferably at least about 75%, more preferably at least about 90% complementary). See Kanehisa, M., 1984, *Nucleic Acids Res.* 12: 203, incorporated herein by reference. As a result, it is expected that a certain degree of mismatch at the priming site is tolerated. Such mismatch may be small, such as a mono-, di- or tri-nucleotide. Alternatively, it may encompass loops, which we define as regions in which mismatch encompasses an uninterrupted series of four or more nucleotides.

Overall, five factors influence the efficiency and selectivity of hybridization of the primer to a second nucleic acid molecule. These factors, which are (i) primer length, (ii) the nucleotide sequence and/or composition, (iii) hybridization temperature, (iv) buffer chemistry and (v) the potential for steric hindrance in the region to which the primer is required to hybridize, are important considerations when non-random priming sequences are designed.

There is a positive correlation between primer length and both the efficiency and accuracy with which a primer will anneal to a target sequence; longer sequences have a higher melting temperature ($T_M$) than do shorter ones, and are less likely to be repeated within a given target sequence, thereby minimizing promiscuous hybridization. Primer sequences with a high G-C content or that comprise palindromic sequences tend to self-hybridize, as do their intended target sites, since unimolecular, rather than bimolecular, hybridization kinetics are genererally favored in solution; at the same time, it is important to design a primer containing sufficient numbers of G-C nucleotide pairings to bind the target sequence tightly, since each such pair is bound by three hydrogen bonds, rather than the two that are found when A and T bases pair. Hybridization temperature varies inversely with primer annealing efficiency, as does the concentration of organic solvents, e.g. formamide, that might be included in a priming reaction or hybridization mixture, while increases in salt concentration facilitate binding. Under stringent annealing conditions, longer hybridization probes (of use, for example, in Northern analysis) or synthesis primers hybridize more efficiently than do shorter ones, which are sufficient under more permissive conditions. Stringent hybridization conditions typically include salt concentrations of less than about 1M, more usually less than about 500 mM and preferably less than about 200 mM. Hybridization temperatures range from as low as 0° C. to greater than 22° C., greater than about 30° C., and (most often) in excess of about 37° C. Longer fragments may require higher hybridization temperatures for specific hybridization. As several factors affect the stringency of hybridization, the combination of parameters is more important than the absolute measure of a single factor.

Primers are designed with these considerations in mind. While estimates of the relative merits of numerous sequences may be made mentally by one of skill in the art, computer programs have been designed to assist in the evaluation of these several parameters and the optimization of primer sequences. Examples of such programs are "PrimerSelect" of the DNAStar™ software package (DNAStar, Inc.; Madison, Wis.) and OLIGO 4.0 (National Biosciences, Inc.). Once designed, suitable oligonucleotides are prepared by a suitable method, e.g. the phosphoramidite method described by Beaucage and Carruthers (1981, *Tetrahedron Lett.*, 22: 1859–1862) or the triester method according to Matteucci et al. (1981, *J. Am. Chem. Soc.*, 103: 3185), both incorporated herein by reference, or by other chemical methods using either a commercial automated oligonucleotide synthesizer or VLSIPS™ technology.

PCR is performed using template DNA (at least 1 fg; more usefully, 1–1000 ng) and at least 25 pmol of oligonucleotide primers; it may be advantageous to use a larger amount of primer when the primer pool is heavily heterogeneous, as each sequence is represented by only a small fraction of the molecules of the pool, and amounts become limiting in the later amplification cycles. A typical reaction mixture includes: 2 µl of DNA, 25 pmol of oligonucleotide primer, 2.5 µl of 10×PCR buffer I (Perkin-Elmer, Foster City, Calif.), 0.4 µl of 1.25 µM dNTP, 0.15 µl (or 2.5 units) of Taq DNA polymerase (Perkin Elmer, Foster City, Calif.) and deionized water to a total volume of 25 µl. Mineral oil is overlaid and the PCR is performed using a programmable thermal cycler.

The length and temperature of each step of a PCR cycle, as well as the number of cycles, is adjusted in accordance to the stringency requirements in effect. Annealing temperature and timing are determined both by the efficiency with which a primer is expected to anneal to a template and the degree of mismatch that is to be tolerated; obviously, when nucleic acid molecules are simultaneously amplified and mutagenized, mismatch is required, at least in the first round of synthesis. In attempting to amplify a population of molecules using a mixed pool of mutagenic primers, the potential for loss, under stringent (high-temperature) annealing conditions, of products that would only result from low melting temperatures is weighed against the promiscuous annealing of primers to sequences other than the target site. The ability to optimize the stringency of primer annealing conditions is well within the knowledge of one of moderate skill in the art. An annealing temperature of between 30° C. and 72° C. is used. Initial denaturation of the template molecules normally occurs at between 92° C. and 99° C. for 4 minutes, followed by 20–40 cycles consisting of denaturation (94–99° C. for 15 seconds to 1 minute), annealing (temperature determined as discussed above; 1–2 minutes), and extension (72° C. for 1 minute). Final extension is generally for 4 minutes at 72° C., and may be followed by an indefinite (0–24 hour) step at 4° C.

Several techniques for detecting PCR products quantitatively without electrophoresis may be advantageously used with the assay of the invention in order to make it more suitable for easy clinical use. One of these techniques, for which there are commercially available kits such as Taqman™ (Perkin Elmer, Foster City, Calif.), is performed with a transcript-specific antisense probe. This probe is specific for the PCR product (e.g. a nucleic acid fragment derived from an NFκB-inducible gene) and is prepared with a quencher and fluorescent reporter probe complexed to the 5' end of the oligonucleotide. Different fluorescent markers can be attached to different reporters, allowing for measurement of two products in one reaction. When Taq DNA polymerase is activated, it cleaves off the fluorescent reporters by its 5'-to-3' nucleolytic activity. The reporters, now free of the quenchers, fluoresce. The color change is proportional to the amount of each specific product and is measured by fluorometer; therefore, the amount of each color can be measured and the RT-PCR product can be quantified. The PCR reactions can be performed in 96 well plates so that samples derived from many individuals can be processed and measured simultaneously. The Taqman™ system has the additional advantage of not requiring gel electrophoresis and allows for quantification when used with a standard curve.

Detection of NFκB-directed transcripts may advantageously be performed in a single tube reaction for reverse transcription of RNA and specific amplification of transcripts of interest. This system utilizes two enzymes, AMV reverse transcriptase to prepare first strand cDNA, and the thermostable Tfl DNA polymerase for second strand cDNA synthesis and subsequent DNA amplification, with an optimized single buffer system that permits RT-PCR to be performed in one step, simplifying the assay and minimizing the chance for contamination during preparation of a separate PCR reaction. Commercial kits such as the Access™ RT-PCR system (Promega; Madison, Wis.) conveniently assemble all materials (except primers) necessary to carry out the method in this way. The single-tube RT-PCR assay according to this technique may be used to assay serum- or other samples.

Alternatively, it is possible to use an enzyme such as rTth polymerase (Perkin Elmer, Foster City, Calif.) that has reverse transcriptase activity in the presence of $Mn^{2+}$ and has DNA polymerase function at higher temperatures (Juhasz et al., 1996, *BioTechniques*, 20: 592–600). Such an enzyme system allows for single tube and single enzyme RT-PCR. PCR product detection has been performed both by polyacrylamide gel electrophoresis and ethidium bromide staining and also by performing the PCR reaction in a 96-well plate in combination with a fluorescent detection system such as the one described above. Utilization of such a fluorescent detection system in the one-tube system allows for the simple addition of RNA to a well containing the buffer, enzymes, dNTPs, primers and the detection probe followed by RT-PCR and luminescent reading. The sensitivities of these systems are equal or superior to standard two-tube methods (Chehadeh et al., 1995, *BioTechniques*, 18: 26–28; Sellner et al., 1992, *Nucleic Acids Res.*, 20: 1487–1490; Juhasz et al., supra), although there is no excess cDNA available for amplification of multiple transcripts.

Alternatively, in situ detection of mRNA transcripts may be performed using either 'squashed' cellular material or to sectioned tissue samples affixed to glass surfaces, prepared as described below. Either paraffin-, plastic- or frozen (Serrano et al., 1989, *Dev. Biol.* 132: 410–418) sections are used in the latter case. Following preparation of either squashed or sectioned tissue, the RNA molecules of the sample are reverse-transcribed in situ. In order to contain the reaction on the slide, tissue sections are placed on a slide thermal cycler (e.g. Tempcycler II; COY Corp., Grass Lake, Mich.) with heating blocks designed to accommodate glass microscope slides. Stainless steel or glass (Bellco Glass Inc.; Vineland, N.J.) tissue culture cloning rings approximately 0.8 cm (inner diameter)×1.0 cm in height are placed on top of the tissue section. Clear nail polish is used to seal the bottom of the ring to the tissue section, forming a vessel for the reverse transcription and subsequent localized in situ amplification (LISA) reaction (Tsongalis et al., 1994, *Clinical Chemistry*, 40: 381–384).

Reverse transcription is carried out using reverse transcriptase, (e.g. avian myoblastosis virus reverse transcriptase, AMV-RT; Life Technologies/Gibco-BRL or Moloney Murine Leukemia Virus reverse transcriptase, M-MLV-RT, New England Biolabs, Beverly, Mass.) under the manufacturer's recommended reaction conditions. For example, the tissue sample is rehydrated in the reverse transcription reaction mix, minus enzyme, which contains 50 mM Tris-HCl (pH 8.3), 8 MM $MgCl_2$, 10 mM dithiothreitol, 1.0 mM each dATP, dTTP, dCTP and dGTP and 0.4 mM oligo-dt (12- to 18-mers). The tissue sample is, optionally, rehydrated in RNAase-free TE (10 mM Tris-HCl, pH 8.3 and 1 mM EDTA), then drained thoroughly prior to addition of the reaction buffer. To denature the RNA molecules, which may have formed some double-stranded secondary structures, and to facilitate primer annealing, the slide is heated to 65° C. for 1 minute, after which it is cooled rapidly to 37° C. After 2 minutes, 500 units of M-MLV-RT are added the mixture, bringing the total reaction volume to 100 $\mu$l. The reaction is incubated at 37° C. for one hour, with the reaction vessel covered by a microscope cover slip to prevent evaporation.

Following reverse transcription, reagents are pipetted out of the containment ring structure, which is rinsed thoroughly with TE buffer in preparation for amplification of the resulting cDNA molecules.

The amplification reaction is performed in a total volume of 25 $\mu$l, which consists of 75 ng of both the forward and reverse primers (for example the mixed primer pools 1 and 2 of Example 6) and 0.6 U of Taq polymerase in a reaction solution containing, per liter: 200 nmol of each deoxynucleotide triphosphate, 1.5 mmol of $MgCl_2$, 67 mmol of Tris-HCl (pH 8.8), 10 mmol of 2-mercaptoethanol, 16.6 mmol of ammonium sulfate, 6.7 $\mu$mol of EDTA, and 10 $\mu$mol of digoxigenin-11-dUTP. The reaction mixture is added to the center of the cloning ring, and layered over with mineral oil to prevent evaporation before slides are placed back onto the slide thermal cycler. DNA is denatured in situ at 94° C. for 2 min prior to amplification. LISA is accomplished by using 20 cycles, each consisting of a 1-minute primer annealing step (55° C.), a 1.5-min extension step (72° C.), and a 1-min denaturation step (94° C.). These amplification cycle profiles differ from those used in tube amplification to preserve optimal tissue morphology, hence the distribution of reverse transcripts and the products of their amplification on the slide.

Amlpified products containing incorporated digoxigenin-11-dUTP are detected with a modification of the protocol supplied with the Genius 1 kit (Boehringer Mannheim Biochemicals; Indianapolis, Ind.), which is briefly summarized as follows: Following amplification, the oil layer and reaction mix are removed from the tissue sample, which is then rinsed with xylene. All solutions and reactions are at room temperature. The containment ring is removed with acetone, and the tissue containing the amplified cDNA is rehydrated by washing three times in approximately 0.5 ml of buffer 1 (100 mM Tris-Cl (pH 7.5) and 150 mM NaCl) and then incubated for 30 minutes in 0.5 ml of buffer 2 (5 ml blocking reagentper liter of buffer 1) in a humidified chamber. Subsequently, the slides bearing the tissue samples are rinsed with 0.5 ml of buffer 1 and incubated for 1 hour with a 1:100 dilution of antibody (alkaline phosphatase-conjugated anti-digoxigenin; Boehringer Mannheim) in a humidified chamber. Excess antibody is removed by three washes in buffer 3 (100 mM Tris.HCl, 100 mM NaCl, 50 mM $MgCl_2$, pH 9.5) before the addition of the chromogen (nitroblue tetrazolium chloride and 5-bromo-4-chloro-3-indolyl phosphate). The detection reaction is monitored for optimal staining (~10–25 minutes) and stopped by rinsing three times in buffer 4 (10 mM Tris.HCl, 1 mM EDTA, pH 8.0). The tissues are then dehydrated in a series of graded alcohols and stained with eosin before coverslips are applied; negative control slides are also stained at this time. Samples are then examined by light microscopy and photographed.

Other measures of restored function include testing of cells for normal mitotic activity, cell viability, cell growth, restored differentiation, normal cell cycle progression and increased protection afforded by NF$\kappa$B.

Immunological Methods i. Preparation of Antibodies

Either recombinant proteins or those derived from natural sources can be used to generate antibodies using standard techniques, well known to those in the field. For example, the proteins are administered to challenge a mammal such as a monkey, goat, rabbit or mouse. The resulting antibodies can be collected as polyclonal sera, or antibody-producing cells from the challenged animal can be immortalized (e.g. by fusion with an immortalizing fusion partner) to produce monoclonal antibodies.

1. Polyclonal Antibodies

The antigen protein may be conjugated to a conventional carrier in order to increases its immunogenicity, and an antiserum to the peptide-carrier conjugate is raised. Coupling of a peptide to a carrier protein and immunizations may be performed as described (Dymecki et al., 1992, *J. Biol. Chem.*, 267: 4815–4823). The serum is titered against protein antigen by ELISA (below) or alternatively by dot or spot blotting (Boersma and Van Leeuwen, 1994, *J. Neurosci. Methods*, 51: 317). At the same time, the antiserum may be used in tissue sections prepared as described below. The serum is shown to react strongly with the appropriate peptides by ELISA, for example, following the procedures of Green et al., 1982, *Cell*, 28: 477–487.

2. Monoclonal Antibodies

Techniques for preparing monoclonal antibodies are well known, and monoclonal antibodies may be prepared using a candidate antigen whose level is to be measured or which is to be either inactivated or affinity-purified, preferably bound to a carrier, as described by Arnheiter et al., *Nature*, 294, 278–280 (1981).

Monoclonal antibodies are typically obtained from hybridoma tissue cultures or from ascites fluid obtained from animals into which the hybridoma tissue was introduced. Nevertheless, monoclonal antibodies may be described as being "raised to" or "induced by" a protein.

Monoclonal antibody-producing hybridomas (or polyclonal sera) can be screened for antibody binding to the target protein. By antibody, we include constructions using the binding (variable) region of such an antibody, and other antibody modifications. Thus, an antibody useful in the invention may comprise a whole antibody, an antibody fragment, a polyfunctional antibody aggregate, or in general a substance comprising one or more specific binding sites from an antibody. The antibody fragment may be a fragment such as an Fv, Fab or $F(ab')_2$ fragment or a derivative thereof, such as a single chain Fv fragment. The antibody or antibody fragment may be non-recombinant, recombinant or humanized. The antibody may be of an immunoglobulin isotype, e.g., IgG, IgM, and so forth. In addition, an aggregate, polymer, derivative and conjugate of an immunoglobulin or a fragment thereof can be used where appropriate.

ii. Detection Methods

Particularly preferred immunological tests rely on the use of either monoclonal or polyclonal antibodies and include enzyme-linked immunoassays (ELISA), immunoblotting and immunoprecipitation (see Voller, 1978, *Diagnostic Horizons*, 2: 1–7, Microbiological Associates Quarterly Publication, Walkersville, Md.; Voller et al., 1978, *J. Clin. Pathol.*, 31: 507–520; U.S. Reissue Pat. No. 31,006; UK Patent 2,019,408; Butler, 1981, *Methods Enzymol.*, 73: 482–523; Maggio, E. (ed.), 1980, *Enzyme Immunoassay*, CRC Press, Boca Raton, Fla.) or radioimmunoassays (RIA) (Weintraub, B., *Principles of radioimmunoassays*, Seventh Training Course on Radioligand Assay Techniques, The Endocrine Society, March 1986, pp. 1–5, 46–49 and 68–78). For analyzing tissues for the presence or absence of a protein in the present invention, immunohistochemistry techniques may be used. Tissue samples to be assayed by these methods are prepared as described below. It will be apparent to one skilled in the art that the antibody molecule will have to labeled to facilitate easy detection of a target protein. Techniques for labeling antibody molecules are well known to those skilled in the art (see Harlour and Lane, 1989, *Antibodies*, Cold Spring Harbor Laboratory, pp. 1–726).

Alternatively, other techniques can be used to detect the target proteins, including chromatographic methods such as SDS PAGE, isoelectric focusing, Western blotting, HPLC and capillary electrophoresis.

Preparation of Histological Samples

Tissue samples intended for use in in situ detection of either RNA or protein are fixed using conventional reagents; such samples may comprise whole or squashed cells, or may instead comprise sectioned tissue. Fixatives adequate for such procedures include, but are not limited to, formalin, 4% paraformaldehyde in an isotonic buffer, formaldehyde (each of which confers a measure of RNAase resistance to the nucleic acid molecules of the sample) or a multi-component fixative, such as FAAG (85% ethanol, 4% formaldehyde, 5% acetic acid, 1% EM grade glutaraldehyde). Note that for RNA detection, water used in the preparation of an aqueous component of a solution to which the tissue is exposed until it is embedded is RNAase-free, i.e. treated with 0.1% diethylprocarbonate (DEPC) at room temperature overnight and subsequently autoclaved for 1.5 to 2 hours. Tissue is fixed at 4° C., either on a sample roller or a rocking platform, for 12 to 48 hours in order to allow fixative to reach the center of the sample.

Prior to embedding, samples are purged of fixative and dehydrated; this is accomplished through a series of two- to ten-minute washes in increasingly high concentrations of ethanol, beginning at 60%- and ending with two washes in 95%- and another two in 100% ethanol, followed two ten-minute washes in xylene. Samples are embedded in one of a variety of sectioning supports, e.g. paraffin, plastic polymers or a mixed paraffin/polymer medium (e.g. Paraplast®Plus Tissue Embedding Medium, supplied by Oxford Labware). For example, fixed, dehydrated tissue is transferred from the second xylene wash to paraffin or a paraffin/polymer resin in the liquid-phase at about 58° C., then replace three to six times over a period of approximately three hours to dilute out residual xylene, followed by overnight incubation at 58° C. under a vacuum, in order to optimize infiltration of the embedding medium in to the tissue. The next day, following several more changes of medium at 20 minute to one hour intervals, also at 58° C., the tissue sample is positioned in a sectioning mold, the mold is surrounded by ice water and the medium is allowed to harden. Sections of 6 µm thickness are taken and affixed to 'subbed' slides, which are those coated with a proteinaceous substrate material, usually bovine serum albumin (BSA), to promote adhesion. Other methods of fixation and embedding are also applicable for use according to the methods of the invention; examples of these are found in Humason, G. L., 1979, *Animal Tissue Techniques*. 4th ed. (W.H. Freeman & Co., San Fransisco), as is frozen sectioning (Serrano et al., 1989, supra).

Assessment of the Efficacy of Disease Treatment According to the Invention

In addition to direct measurements of protein or nucleic acid levels in target cells resulting from the specific composition administered by the methods of the present invention, it is possible to monitor changes in the disease state in patients receiving therapy to enhance NFκB activity and compare them to the progression or persistence of disease in control patients who are treated with placebos (i.e. a pharmaceutically-acceptable carrier without the therapeutic nucleic acid, protein or other agent).

In treating autoimmune diseases according to the invention, it is possible to deliver one or more of a number of therapeutically-relevant nucleic acids proteins or other substances to cells or a recipient individual. A sampling of genes and/or proteins that might be of use is provided above. Following administration of the chosen composition, an improved rate of improvement in diagnostic clinical indicators (e.g. insulin or blood sugar level in the case of diabetes) in those patients receiving the therapeutic gene(s), protein(s) or other agent(s) relative to those who do not is indicative of efficacious disease treatment using the methods of the invention.

The progression of autoimmune disorders may be slowed or reversed according to the methods of the invention. Treatment of an autoimmune disorder using the invention may be judged advantageous if the loss of tissue or function thereof in patients so treated is slowed or halted relative to untreated control individuals; for example, the p50 and/or the p65 gene, which encode the p50 and p65 subunits of NFκB, may be administered in vivo (e.g., by systemic or localized injection) or ex vivo into cells which are subsequently transplanted into a clinical patient, and the recipient patient monitored for elimination of tissue or functional loss, or a reduction in such loss sufficient to result in noticeable improvement in health.

EXAMPLE 1

In this Example, the role that phosphorylation of NFκBp65 by cyclin-dependent kinase (Cdk) might play in the maturation of lymphocytes in the immune system is assessed, as is the possibility that this NFκBp65 activation step links defective lymphocyte development to diabetes in the NOD mouse model.

To demonstrate an association of NFκBp65 with a cell cycle development regulator protein involved in Cdk/Cyclin coupling, a glutathione-S-transferase (GST) NFκBp65 fusion protein was utilized in an affinity purification protocol. GST-NFκBp65 fusion proteins, wild type NFκBp65 or deletion mutants, NFκBp65 Q417 and NFκBp65 C418 were constructed and characterized. GST-carboxy-terminal domain (CTD) of RNA polymerase II large subunit fusion proteins were also constructed and utilized as the substrate of kinase assay. Genes encoding the carboxy-terminal domain (CTD) of RNA polymerase II large subunit or either wild-type- or mutant NFκB subunit p65 were inserted into the pGEX2T fusion-protein expression vector (Pharmacia; Uppsala, Sweden) by molecular biology techniques which are well known in the art (see Sambrook et al., 1989, supra). The GST-CTD or GST-NFκBp65 proteins were expressed in E. coli strain BL21 (DE3) LysS. Cultures (50 ml) were grown overnight at 37° C.; the next day, the resulting stationary-phase cultures were diluted 1:100 with fresh LB medium containing ampicillin (100 μg/ml) and grown until $A_{600}$=0.6 optical density units (O.D.U.) at 30° C. Production of GST-CTD or GST-NFκBp65 fusion proteins encoded by genes under control of the Ptac promoter was then induced for 3 hours with isopropyl-thio-P-D-galactoside (IPTG; an inducer which causes derepression of transcription and subsequent GST fusion protein expression) at a final concentration of 0.4 mM. The cultures were collected by centrifugation and the bacterial pellets are resuspended in 4 ml PBS (150 mM NaCl, 16 mM $Na_2HPO_4$, 4 mM $NaH_2PO_4$) with 5 mM DTT. The GST-CTD and GST-NFκBp65 fusion proteins were purified from the lysate by binding to glutathione-Sepharose beads (Pharmacia).

Phosphorylation is a common mechanism of regulating proteins involved in cell cycle and transcription and CTD of mammals consists of 52 identical copies of the heptapeptide sequence Tyr-Ser-Pro-Thr-Pro-Ser (SEQ ID NO:4). To investigate if phosphorylation of NFκBp65 might be mediated through a cellular protein kinase, we looked for an association of NFκBp65 with a cellular protein kinase. Nuclear and cytosolic extracts were prepared from a human T-cell lymphoma cell line, Molt-4; note that the preparation protocol is identical to that used to prepare protein extracts from spleen tissue removed from six-week-old male and female NOD mice (see below). Cells were harvested, centrifuged for 15 minutes at 3000 rpm, washed in 10 ml of ice-cold PBS and collected by centrifugation for 15 minutes at 3000 rpm. The pelleted cells were resuspended in 4 ml of buffer A (10 mM Hepes, pH 7.8; 10 mM KCl; 2 mM $MgCl_2$; 1 mM DTT; 0.1 mM EDTA; 0.1 mM PMSF) and incubated on ice for 15 min. Then 250 μl of 10% Nonidet P-40 solution (Sigma; St. Louis, Mo.) were added and cells were vigorously mixed and incubated for 30 minutes at 4° C. The harvested cells were centrifuged for 15 min at 3000 rpm. The resulting supernatant comprised the cytosolic fraction, and is herein referred to as the "cytosol extract". Pelleted nuclei were resuspended in 1500 μl of buffer C (50 mM Hepes, pH 7.8; 50 mM KCl; 300 mM NaCl; 0.1 mM EDTA; 1 mM DTT; 0.1 mM PMSF; 10% (v/v) glycerol), mixed for 30 minutes and centrifuged for 15 minutes at 3000 rpm at 4° C. The supernatant obtained at this step contained the nuclear proteins; hence, this supernatant is herein referred to as the "nuclear extract". The concentration of protein was 20 μg/μl.

Figure 1A:
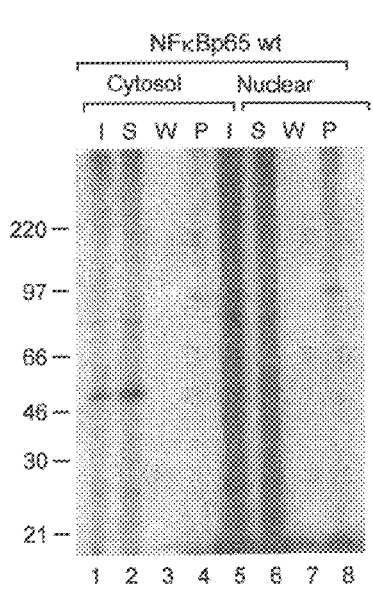
Figure 1B:
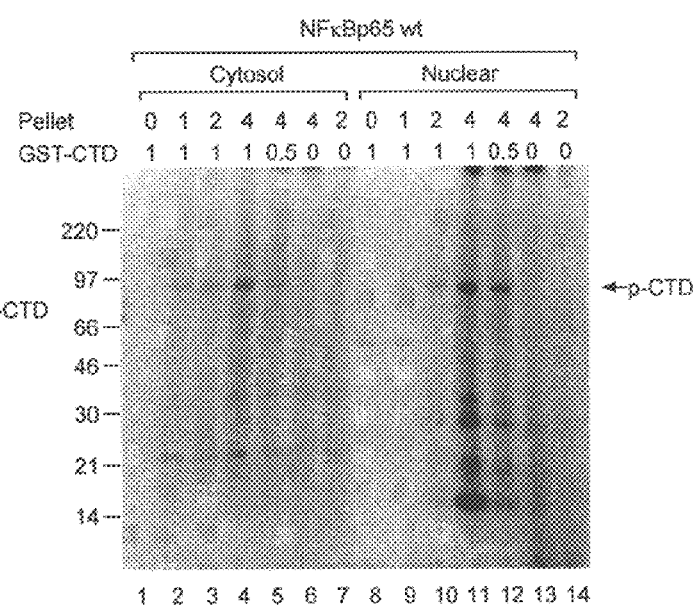
Figure 1C:
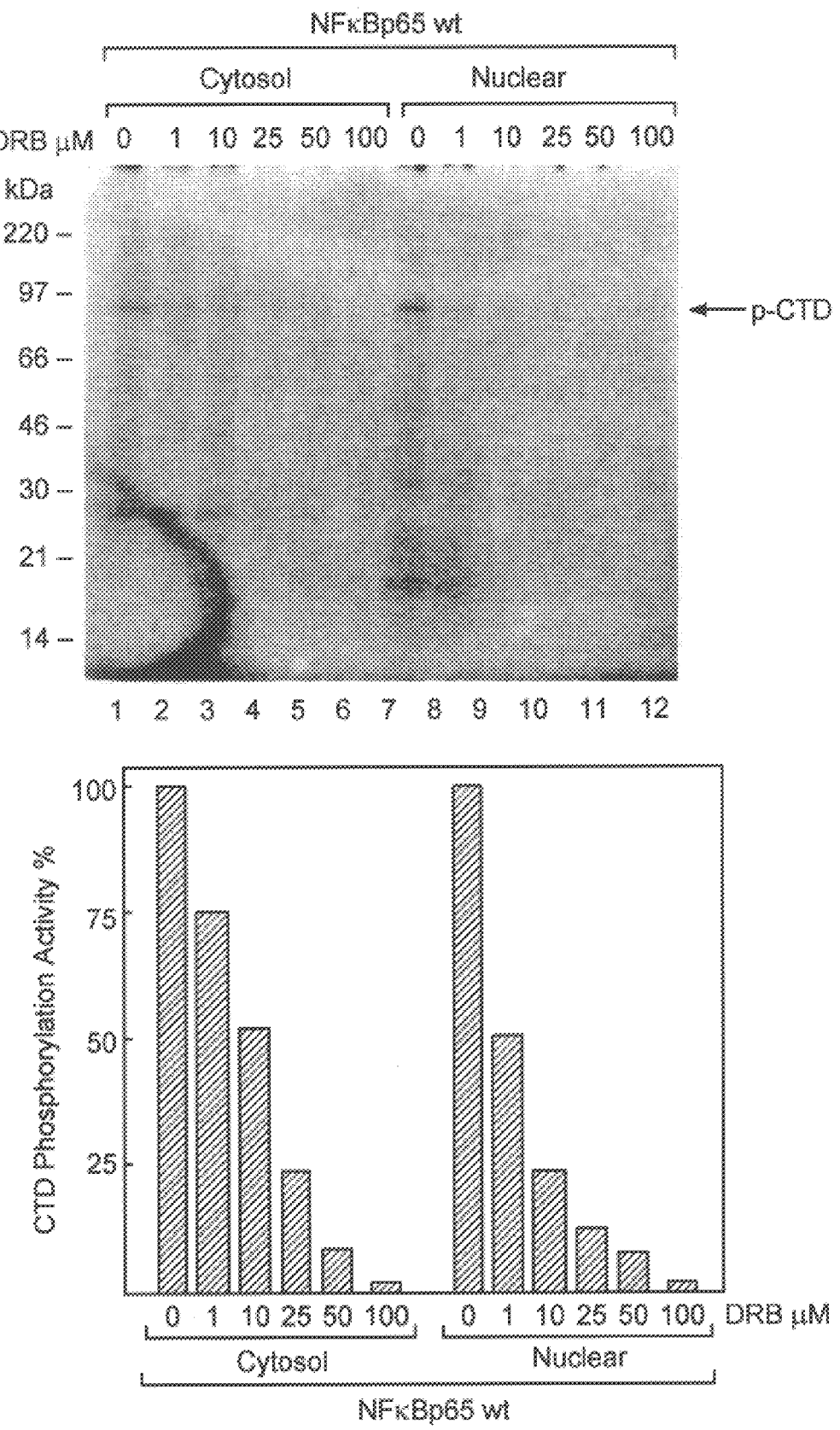

GST-NFκBp65 and GST-CTD were expressed in BL21 pLysS E. Coli cells and purified by selective absorption to glutathione sepharose beads. GST-NFκBp65 was incubated with Molt-4 cytosolic and nuclear extracts, prepared as described above. Reaction mixtures were washed in PBS. The precipitated complexes were then incubated with GST-CTD of RNA polymerase II large subunit in kinase buffer containing γ-[$^{32}$P]ATP as previously described (Hayashi et al., 1993, J. Biol. Chem., 268: 26790–26795; Faustman et al., 1989, Diabetes, 38: 1462–1468). One-fortieth of the input (I) and supernatant (S) fractions and 1/40 of the last wash (W) and pellet (P) fractions were used for in vitro kinase reaction. Protein complexes were collected by brief centrifugation, washed and then incubated with GST-CTD substrates in kinase buffer containing γ-$^{32}$P ATP. The products of the in vitro kinase reactions were then analyzed on SDS-PAGE. A protein of approximately 90 kD was phosphorylated in the in vitro kinase reaction (FIG. 1A). The 90 kDa phosphorylated protein was dependent upon the presence of GST-CTD in the reaction mixtures (FIG. 1B). As FIG. 1 shows, both GST-NFκBp65/protein complexes associated with cellular protein kinases which may phosphorylate a CTD. The prime nucleoside analog, 5,6-dichloro-1-β-D-ribofuranosylbenzimidazole (DRB) can inhibit the activity of cellular kinases (Marciniak and Sharp, 1991, EMBO J., 10: 4189–4196). To determine whether the kinase activity of NFκBp65-associated protein kinase were sensitive to DRB, the ability of DRB to inhibit the kinase activity of NFκBp65 association protein kinase was tested by examining the phosphorylation of CTD in the presence of different concentrations of DRB. In vitro kinase assays were carried out and phosphorylated GST-CTD products were separated by SDS-PAGE and visualized by autoradiography. Quantitation of the gel shown in FIG. 1C with an image analyzer (a BAS 3000 phosphorimager) was plotted on a graph. The concentrations of DRB indicated in the figure were included in the respective kinase reaction mixtures. From these data, it is apparent that the kinase activities of NFκBp65-associated protein kinases (cytosolic and nuclear) were sensitive to DRB in a dose-dependent manner. The concentrations of DRB required for 50% inhibition of the activity of NFκBp65-associated protein kinase were 10 μM (cytosolic) and 1 μM (nuclear) (FIG. 1C).

To confirm that general inhibition of kinase activity was not responsible for the observed results, the sensitivity of NFκBp65-associated protein kinase to DRB was also tested with casein, which has multiple phosphorylation sites, as the substrate. There was a difference in the biochemical character of NFκBp65 association protein kinase between cytosol and nuclear. In that NFκBp65 may associate with different protein kinases in the cytosol and the nucleus (cytosol; band A and nuclear; band B), the target amino acid residues on the CTD substrate molecule were determined by phosphoamino acid analysis (see Baeuerle and Baltimore, 1996, supra). In brief, $^{32}$P-labeled GST-CTD fusion proteins were eluted from wet gels and precipitated with trichloroacetic acid, hydrolyzed for 2 hours in 200 μl of 6 M HCl boiling constantly at 110° C. and then dried. The samples were resuspended in formic acid/acetic acid buffer (pH 1.9) and spotted onto a glass-backed silica gel plate. These samples, along with 2 μl each of unlabeled phosphoamino acids (phosphoserine, phosphothreonine and phosphotyrosine; Sigma) as internal markers, were analyzed by thin-layer electrophoresis at pH 1.9. Phosphoamino acids were visualized by autoradiography. The results, shown in FIG. 1D revealed that only serine residues in the CTD were phosphorylated, indicating that serine or serine/threonine kinases may associate with NFκBp65.

To identify the domain on NFκBp65 molecule which is essential for the recognition by cellular serine and/or serine/threonine kinases, in vitro kinase assays were performed using other deletion mutants, GST-NFκBp65 Q417 and -C418. In vitro and in vivo studies indicate that the p65 subunit of NF-κB is responsible primarily for transcriptional activation by NF-κB, and a potent transactivation domain has been mapped to a carboxyl-terminal region of p65 that is not shared with p50 (Verma et al., 1995, supra; Baeuerle and Baltimore, 1996, supra; Schmitz and Baeuerle, 1991, *EMBO J.*, 10: 3805–3817; Fujita et al., 1992, *Genes Dev.*, 6: 775–787; Kerr et al., 1993, *Nature*, 365: 412–419; Pazin et al., 1996, *Genes Dev.*, 10: 37–4933–36). Therefore, it was of interest to determine whether the transactivation domain of NFκBp65 were sufficient for the activity of NFκBp65-associated protein kinases, or it other elements were required. GST-NFκBp65 Q417 represents the deleted trans-activation domain of NF-κBp65, while GST-NFκBp65 C418 is the GST-trans-activation domain only of NFκBp65. CTD phosphorylation activities were generated strongly in in vitro kinase reaction using GST-NFκBp65 C418/nuclear protein complexes, but kinase activity was only mildly detected in GST-NFκBp65 C418/cytosolic protein complexes (FIG. 1E), suggesting that the transactivation domain of NFκBp65 is required for high-affinity kinase binding. The results of signal quantitation of the gel shown in FIG. 1E (again performed using a BAS 3000 phosphorimager) were plotted on a graph. The difference in the binding properties of NFκBp65 to protein kinases in the cytosol and the nucleus suggests that NFκBp65 associates with different protein kinases in these two regions of the cell.

Figure 1D:
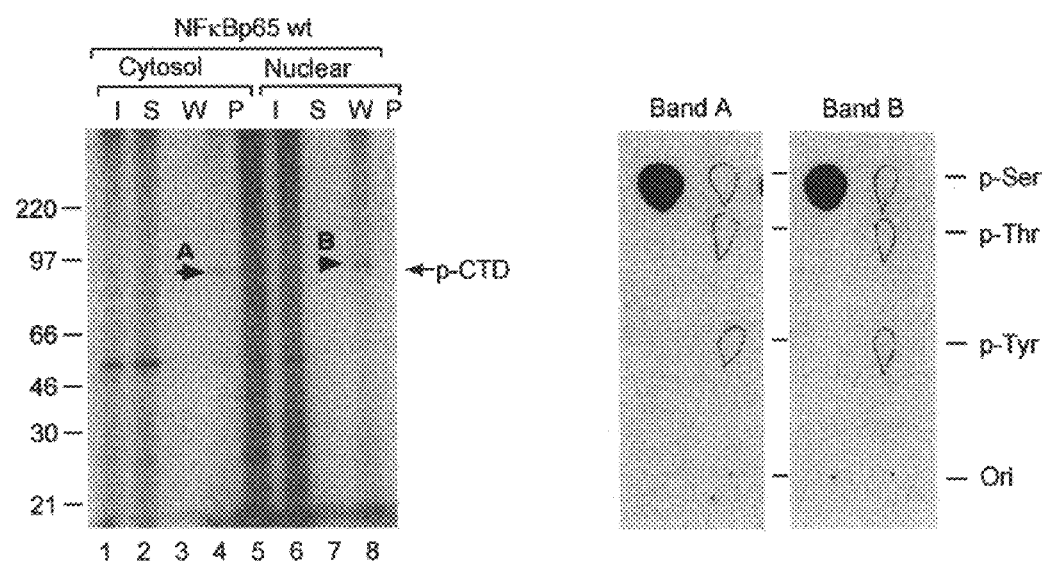
Figure 1E:
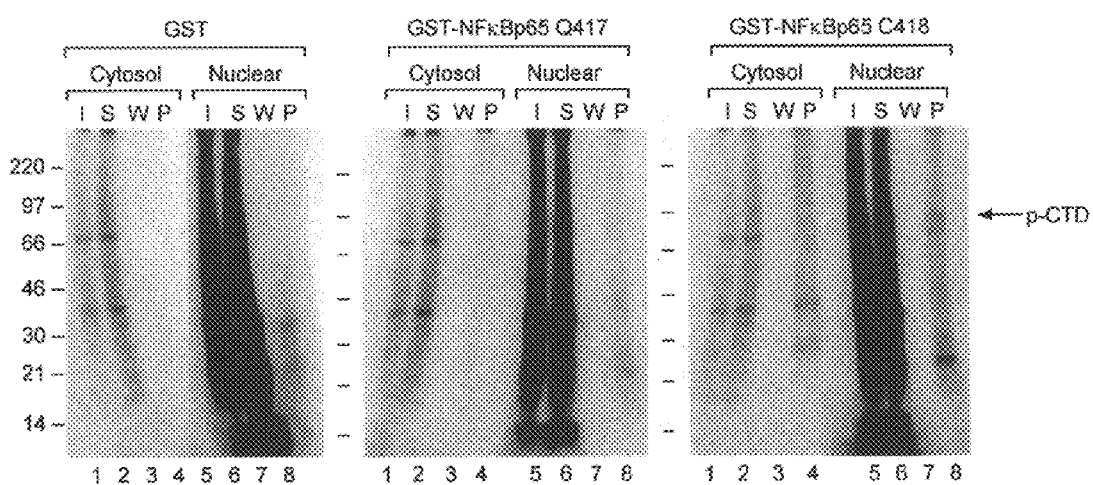

To further characterize the kinase activities of the proteins represented by cytosolic band A and nuclear band B in FIG. 1D, azide ATP UV-crosslinking assays were performed as previously described (Hayashi et al., 1993, supra). In short, ATP affinity-labeling was performed on complexes immunoprecipitated by an anti-NFκBp65 polyclonal antibody (Santa Cruz Biotechnology, Inc.; Calif.) or instead on purified GST-NFκB fusion proteins (wild-type and C417). The protein complexes were incubated with 10 μCi of 8-azide-α-[$^{32}$P]ATP in kinase buffer at 37° C. for 30 minutes. The samples were placed 5 cm distant from a UV lamp (wavelength=254 nm) and irradiated on ice for 30 minutes. After addition of 10 μl of sampling buffer (2.5% SDS, 0.65 mM DTT, 0.5 M sucrose) for SDS-polyacrylamide gel electrophoresis (SDS-PAGE), the ATP-binding proteins were separated on a 12.5% SDS-PAGE and visualized by autoradiography.

Figure 2A:
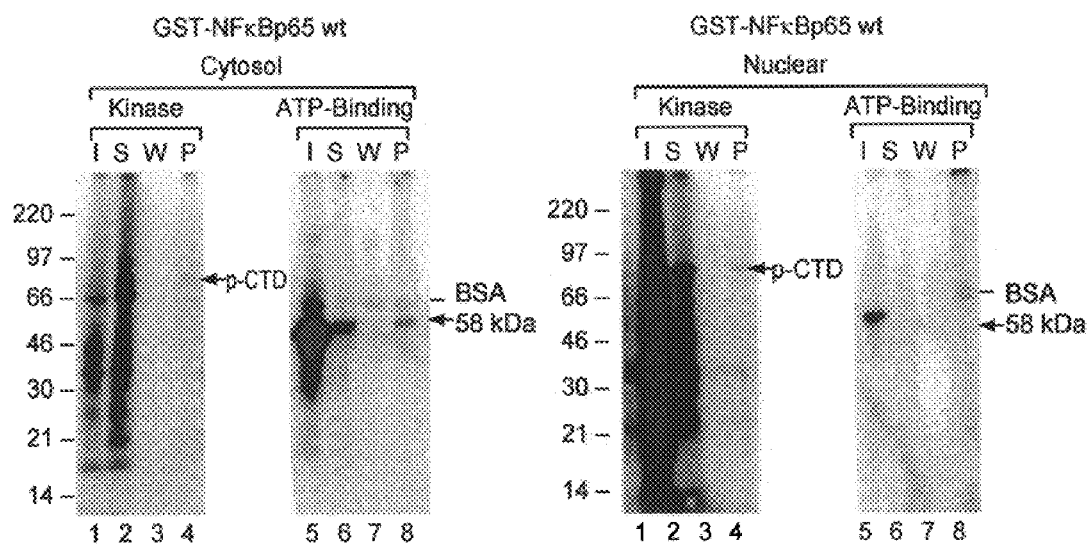
Figure 2B:
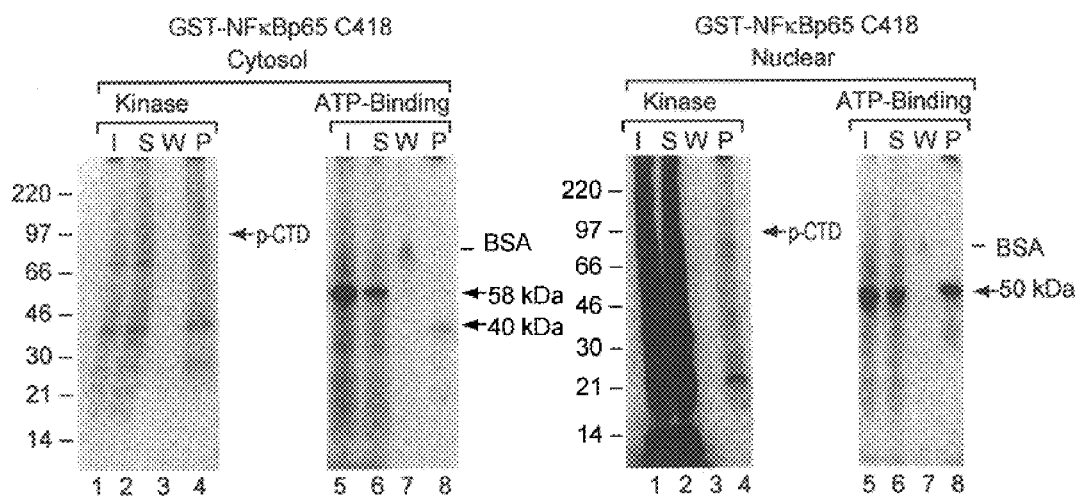
Figure 2C:
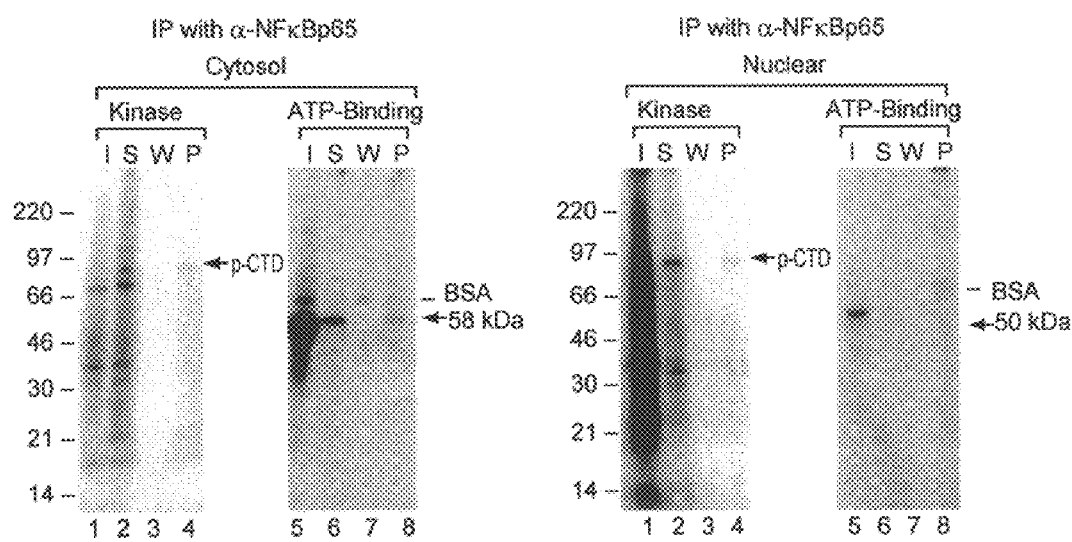

The results are shown in FIG. 2. ATP-binding proteins of different molecular weights were detected in these assays. Single bands representing 53 kD and 50 kD proteins with ATP binding activities were detected in the cytosolic and nuclear samples, respectively (FIG. 2).

It is possible that the 50 kD nuclear ATP-binding protein associates with NFκB and can phosphorylate CTD, because the observed ATP binding proteins appeared as single bands in the in vitro ATP-binding assay. The cytosolic 53 kD protein recognized both wild-type and deletion mutant C418 NFκBp65 proteins and phosphorylated CTD. To verify these findings, similar ATP binding assays were performed with protein complexes immunoprecipitated from cytoslic and nuclear extracts using an anti-NFκBp65 polyclonal antibody. The proteins UV-crosslinked with 8-azide-α-[$^{32}$P] ATP were separated by SDS-PAGE and visualized. The 53 kD (cytosolic) and 50 kD (nuclear) protein bands were again detected. Co-immunoprecipitation of these proteins with the NFκBp65 from cytosolic and nuclear extracts metabolically labeled with [$^{35}$S]-methionone and [$^{35}$S]-cysteine was also attempted; the results suggest that serine or serine/threonine kinases of 53 kD (cytosolic) and 50 kD (nuclear) can associate with NF-κBp65 (data not shown).

Figure 3A:
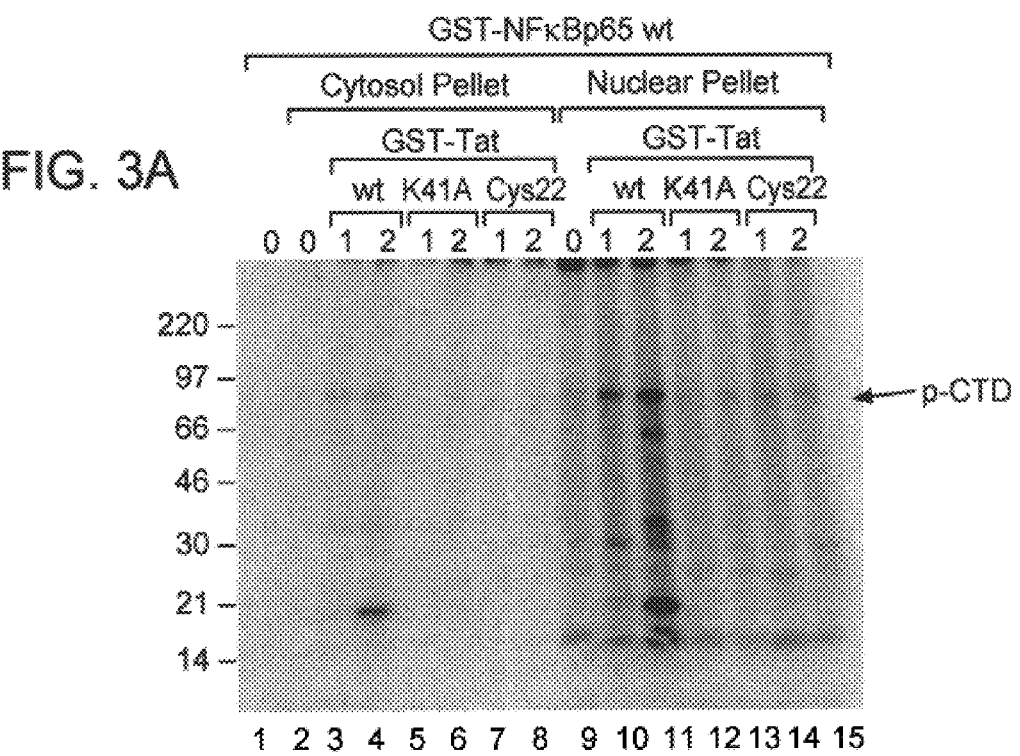
Figure 3B:
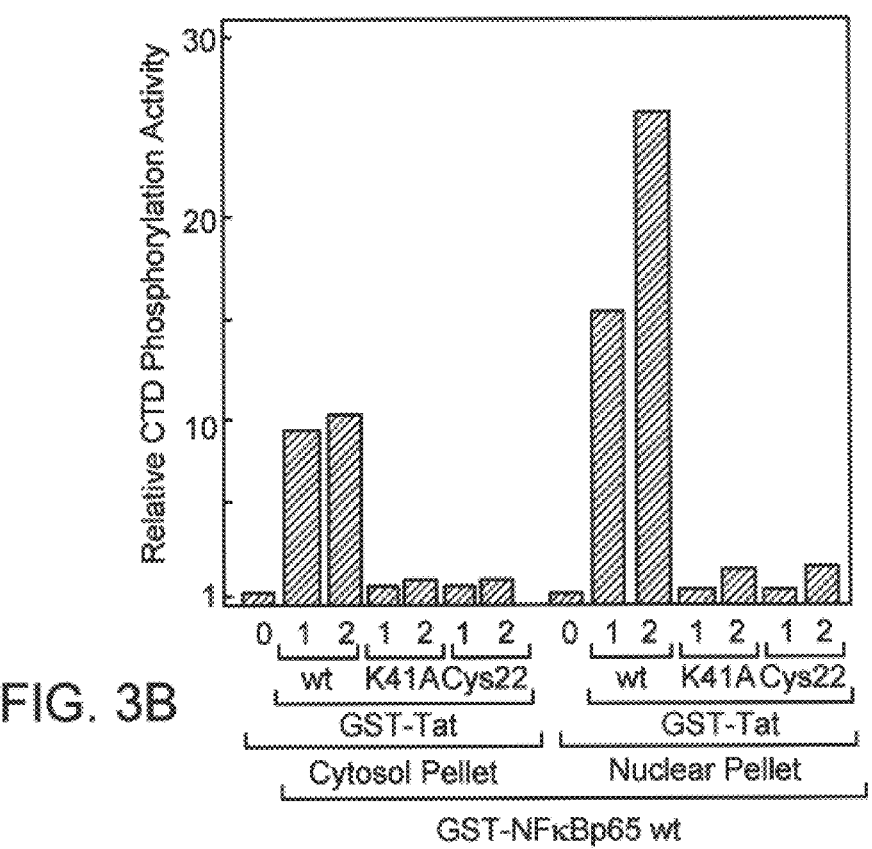

HIV-1 Tat protein is a trans-activator that selectively activates transcription in vivo and in vitro experiments. Recent in vitro studies indicate that Tat activates the CTD phosphorylation activity (Parada and Roeder, 1996, *Nature*, 384: 375–378). The ability of Tat to activate CTD phosphorylation activities of the protein kinases associated with NFκBp65 was tested by in vitro kinase assays in which the concentration of Tat in reaction mixture was varied. As shown in FIG. 3, CTD phosphorylation was activated strongly by wild-type Tat in a dose-dependent manner; however, no such activation was observed when the Tat mutant proteins K41A or Cys22 were assayed. Signal quantitation of the gel shown in FIG. 3A was performed as described above, and the results were plotted on a graph (FIG. 3B). When wild-type Tat was included in the kinase reaction mixture, CTD phosphorylation by the nuclear kinase associated with NFκBp65 was induced 15- and 25-fold more strongly than in the absence of Tat. On the other hand, CTD phosphorylation activity of the cytosol kinase associated with NFκBp65 was activated 10-fold by wild-type Tat. A phosphorylated protein with a molecular mass of approximately 40 kD (again, as judged by electrophoretic mobility in SDS-PAGE analysis) was detected in the nuclear kinase reaction (FIG. 3A, lane 11). It is likely that Tat protein was phosphorylated by NFκBp65-associated nuclear kinase, however the phosphorylated form of Tat protein was not detected in the cytosol reaction mixture. This was confirmed by the finding that different kinases associate with NFκBp65 in the nucleus and the cytosol.

Figure 4A:
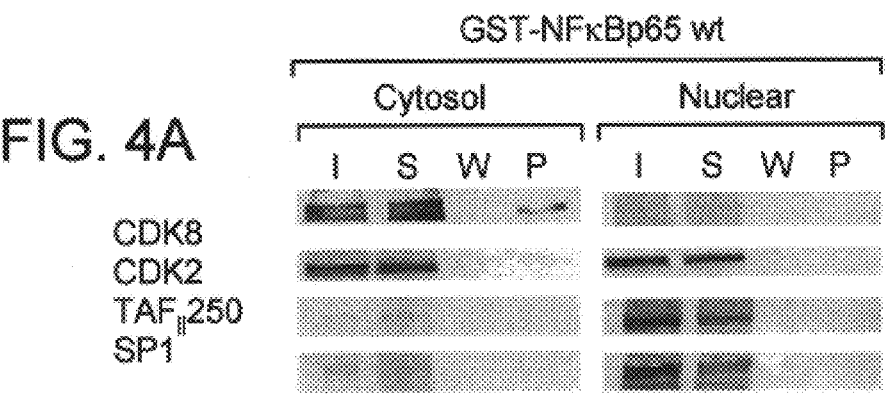
Figure 4B:
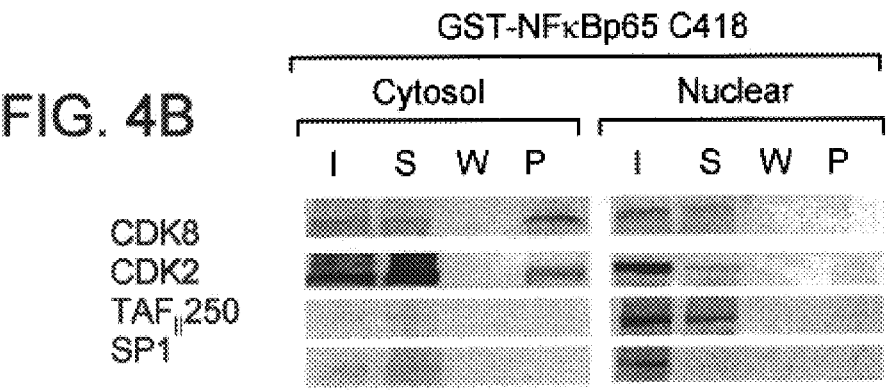
Figure 4C:
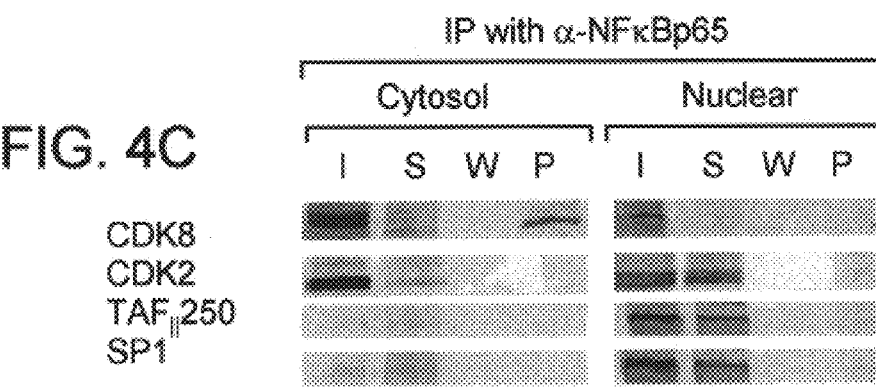

One may conclude that it is likely that serine or serine/threonine kinases with apparent molecular masses of 53 kD (cytosol) and 50 kD (nucleus) associate with NFκBp65. Furthermore, the activities of these kinases is inhibited by DRB in a dose-dependent manner. These protein kinases are similar in size to an NFκB kinase which may be cytosolic Cdk8 (Tassan et al., 1995, *Proc. Natl. Acad. Sci. U.S.A.*, 92: 8871–8875; Leclerc et al., 1996, *Mol. Biol. Cell*, 7: 505–513; Rickert et al., 1996, *Oncogene*, 12: 2631–2640). To determine whether the 53 kD protein kinase is Cdk8, Western analysis was carried out using an anti-Cdk8 polyclonal antibody and appropriate control antibodies. As shown in FIG. 4A, anti-Cdk8 antibody recognized the 53 kD cytosolic protein kinase associated with wild-type and C418 mutant NFκBp65; in addition, Cdk8 was co-immunoprecipitated with anti-NFκBp65 (FIG. 4C). Cdk2 was found to associate only weakly with GST-NFκBp65; however, it complexed strongly with GST-NFκBp65 C418 mutant protein (FIG. 4B). Cdk2 was co-immunoprecipitated weakly from cytosolic extracts when an anti-NFκBp65 polyclonal antibody was used (FIG. 4C). As expected, TAF$_{II}$250 and SP1 did not associate with either wild-type or C418 mutant NF-κBp65 (FIGS. 4A and 4B). No antibody binding to proteins of nuclear extracts was observed if wild-type GST-NFκBp65 protein was added. Cdk8 and Cdk2 did not co-immunoprecipitate from nuclear extracts with NFκBp65 (FIG. 4C). From these immunoblotting results, it is apparent that cytosolic Cdk8 can associate with NFκBp65; however, the association of nuclear Cdk2 NFκBp65 was not clearly indicated.

Figure 5A:
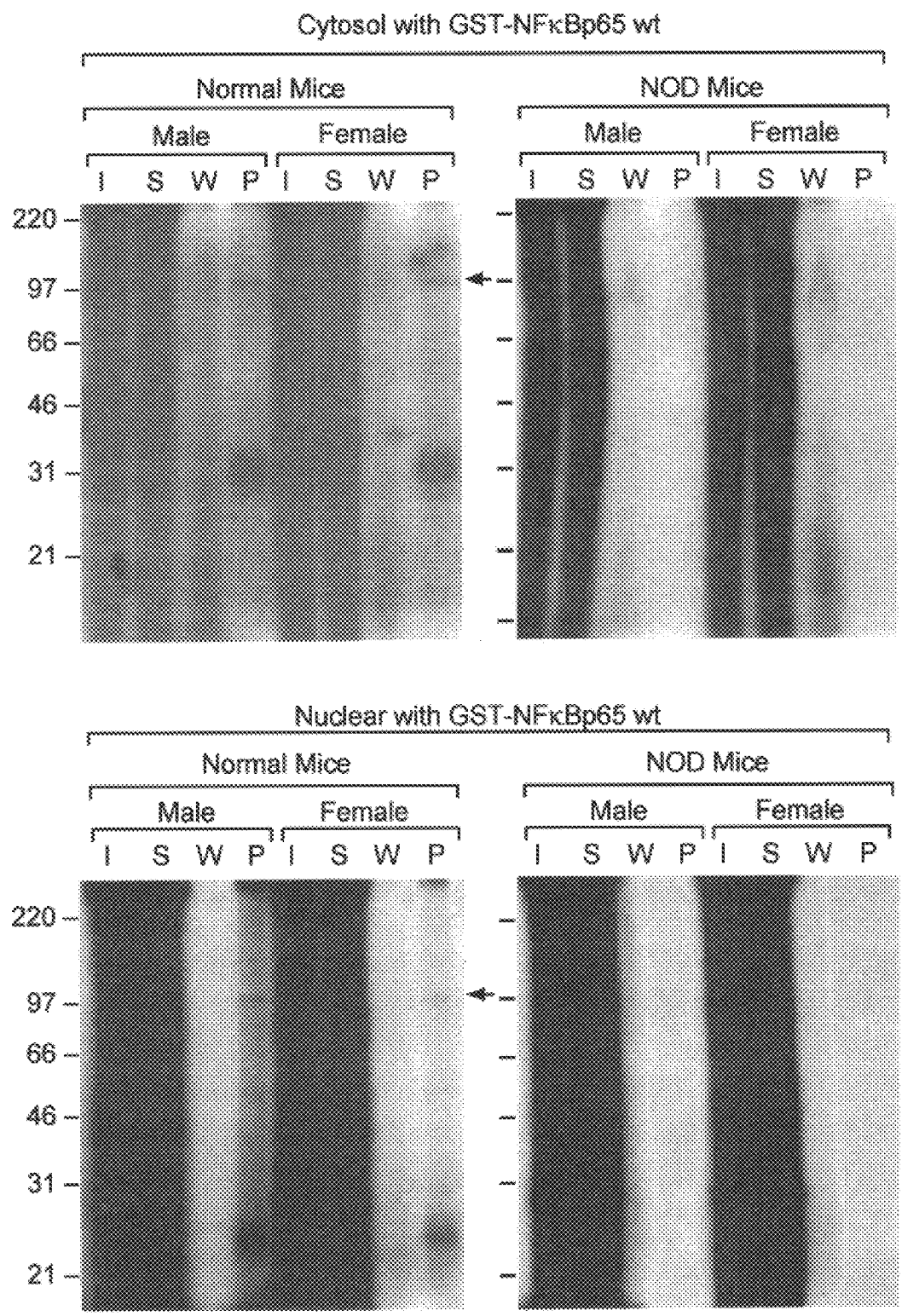
FIG. 5 shows the absence of association of NFκBp65 with Cdks in NOD mice.
Figure 5B:
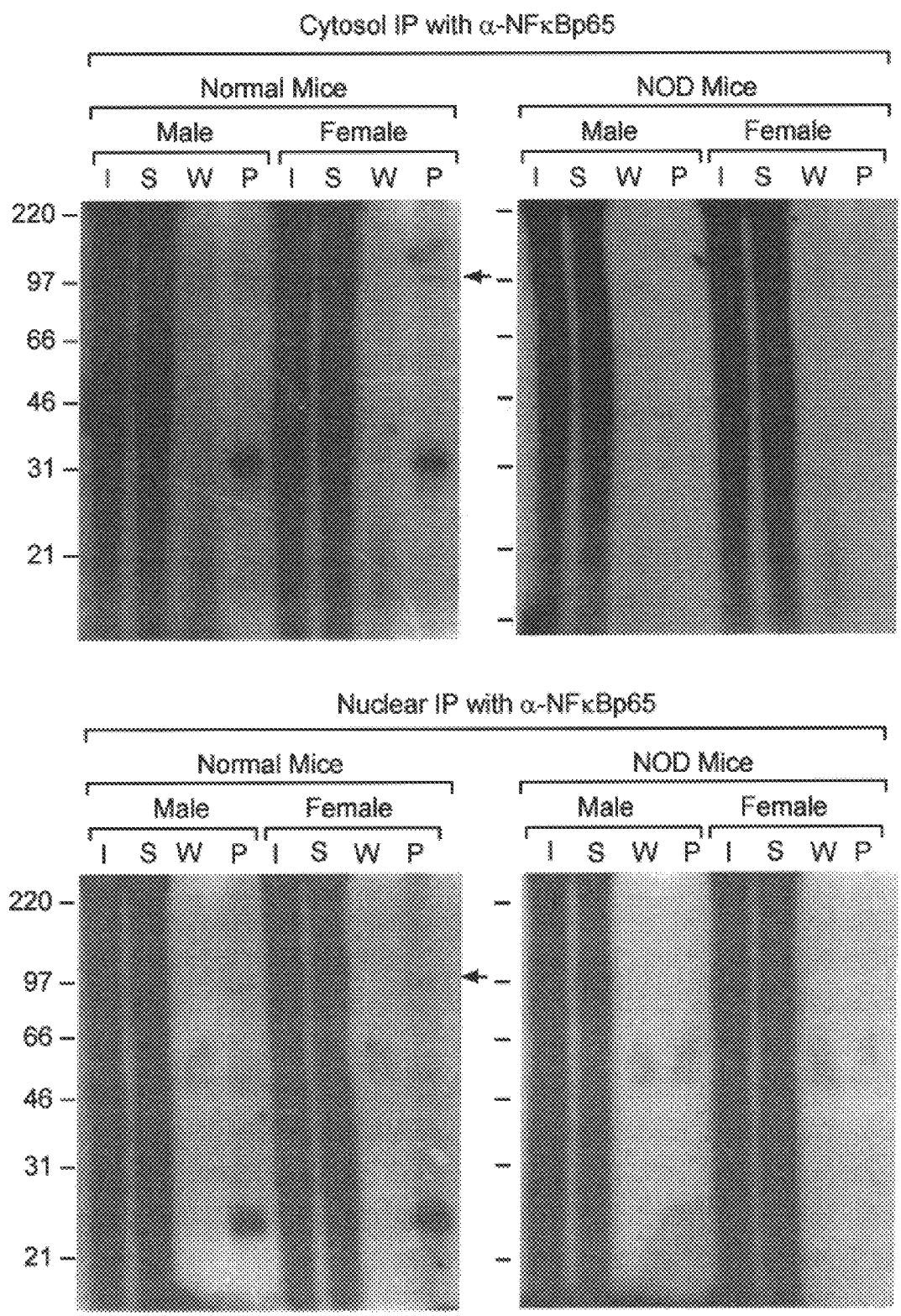

Type I diabetic models of autoimmunity include a murine model, the NOD mouse. As described above, NOD mice exhibit immature forms of T cells, B cells and macrophages in the immune system as well as signal transduction errors. To determine whether NFκBp65 dysfunction plays a role in autoimmune pathogenesis, cytosolic and nuclear extracts from normal and NOD mice were compared in in vitro kinase assays. The mice at 5–6 weeks of age were normoglycemic (hyperglycemic onset due to complete β cell destruction typically occurs beyond 20 weeks). Cytosolic extracts were prepared from spleens removed from normal mice and NOD mice as described above and elsewhere (Wu et al., 1996, supra). The GST-NFκBp65 fusion proteins were mixed with cytosol and nuclear extracts purified from normal mice and NOD mice. The protein complexes were isolated by affinity binding to GST-Sepharose beads; after washing, the complexes were incubated with GST-CTD substrate in a kinase buffer that included γ-[$^{32}$P]ATP. In vitro kinase assay was performed using the CTD substrate and the reaction products were analyzed by 12% SDS-PAGE. Kinase activity was observed in normal mice, both male and female, but was not detectable in NOD mice (FIG. 5A). To verify this result, a more sensitive in vitro kinase assay was performed. Rather than using crude extracts, enriched protein samples were generated using an anti-NFκBp65 polyclonal antibody to immunoprecipitate NFκBp65 comlexes from cytosolic and nuclear extracts prepared from normal and NOD mice. NFκBp65-associated kinase activities were strongly evident in normal mice; still no kinase activity was detected in NOD mice (FIG. 5B).

Figure 5C:
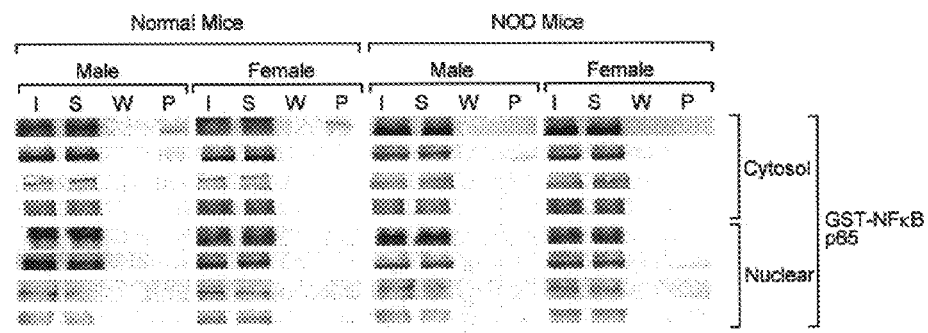
Figure 5D:
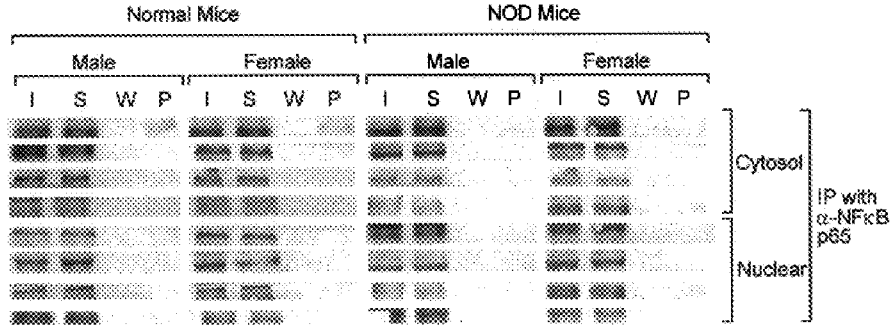

To further characterize the NOD defect in NFκBp65 phosphorylation, the specific interactions of Cdks with NFκBp65 were evaluated by Western analysis. Cdk8 was detected by a polyclonal antibody directed against it, and was appropriately associated with GST-NFκBp65 in cytosolic extracts derived from normal mice, while no association of NFκBp65 with the Cdk8 protein was observed in NOD mice (FIG. 5C). In control extracts, Cdk2 proteins were detected weakly in GST-NFκBp65/protein complexes (FIG. 5C); in NOD mice, Cdk2 proteins were not associated with NFκBp65. As expected, TAF$_{II}$250 and SP1 were not associated with NFκBp65 in control or NOD mice (FIGS. 5C, D). No antibody tested was able to bind proteins found in nuclear extracts of either normal or NOD mice, if wild-type GST-NFκBp65 were added; in this case, neither Cdk8 nor Cdk2 was found to co-immunoprecipitate with NFκBp65 in nuclear extracts prepared from either mouse strain (FIG. 5C). The basal expression levels of Cdk8, Cdk2, NFκBp65, SP1 and TAF$_{II}$250 did not differ between normal and NOD mice (data not shown). From these immunoblotting results, it is evident that in cytosolic Cdk8 can associate with NFκBp65 in normal, but not NOD, mice.

EXAMPLE 2

In the previous Example, the cytoplasmic activities of NFκB were examined. In the present Example, the nuclear activity of NFκB is explored in both normal and autoimmune mice.

Figure 6A:
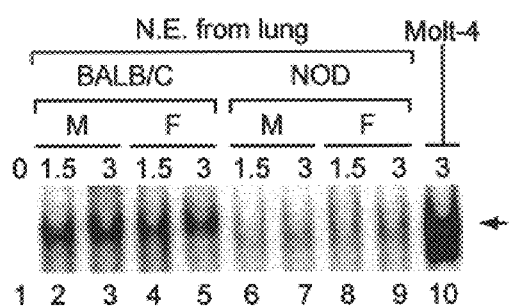
FIG. 6 shows DNA-binding activities of NFκB and other transcription factors in lung tissue of BALB/C and NOD mice.

Specific binding of NFκB to its recognition sequence on a nucleic acid molecule was assayed by electrophoretic mobility shift analysis (EMSA). In this procedure, protein samples are incubated with labeled nucleic acid molecules under conditions which permit nucleic acid/protein binding for a time sufficient to allow such binding to occur and then electrophoresed on non-denaturing polyacrylamide gels, which are subsequently subjected to a signal detection procedure, such as autoradiography. A κB binding site consists of a 5' and a 3' half site, of which may variants exists; different members of the κB protein family (e.g. NFκB, IκB) have different degrees of affinity for different half-sites or combinations thereof, as reviewed by Siebenlist et al. (1994, supra). In this set of experiments, the affinity of NFκB for two binding site variants (denoted κB$_1$ and κB$_2$) is examined. Lung extracts were used because lung tissue has a high concentration of lung-antigen-presenting cells, and thus would be expected to have high levels of active NFκB. BALB/c mice display high levels of NFκB activity in the lymphoid cells of the lung. Nuclear extracts and cytosolic extracts were prepared from human T-cell lymphoma Molt-4 cells, as well as lung and spleen tissue removed from six-week-old BALB/c (normal) and NOD autoimmune mice, both male and female. Lung, spleen and cultured cells were harvested, centrifuged for 15 minutes at 3000 rpm, washed in 10 ml of ice-cold PBS and collected by centrifugation for 15 minutes at 300 rpm. The pelleted cells were resuspended in 4 ml of buffer A (10 mM Hepes, pH 7.8; 10 mM KCl; 2 mM MgCl$_2$; 1 mM DTT; 0.1 mM EDTA; 0.1 mM PMSF) and incubated on ice for 15 minutes. Then 250 μl of 10% Nonidet P-40 solution (Sigma) were added and cells were vigorously mixed and incubated for 30 minutes at 4° C. The harvested cells were centrifuged for 15 minutes at 3000 rpm. After centrifugation, the supernatant comprised cytosolic proteins, and was termed the cytosolic extract. Pelleted nuclei were resuspended in 1500 μl of buffer C (50 mM Hepes, pH 7.8; 50 mM KCl; 300 mM NaCl; 0.1 mM EDTA; 1 mM DTT.; 0.1 mM PMSF; 10% (v/v) glycerol), mixed for 30 minutes and centrifuged for 15 min at 300 rpm at 4° C. This supernatant contained the nuclear proteins at a concentration of 20 μg/μl), and was termed the nuclear extract. The nuclear lung extracts so prepared were incubated with a $^{32}$P end-labeled oligonucleotide containing the NFκB binding sequence (5'-GATCTAGGGACTTTCC GCTGGGGACTTTCCAG-3' (SEQ ID NO:5) under conditions which permit specific DNA/protein binding (e.g., as below). FIG. 6A presents the results of this experiment (BALB/C male, lanes 2–3 and female, lanes 4–5; NOD male lanes 6–7 and female lanes 8–9; Molt-4, lane 10). The labeled DNA probe was included in the reaction mixtures containing nuclear extracts (1.5 μl lane 2, 4, 6, 8; 3.0 μl lane 3, 5, 7, 9, 10) and, as a negative control, in a reaction mixture that was free of nuclear extract (lane 1).

Figure 6B:
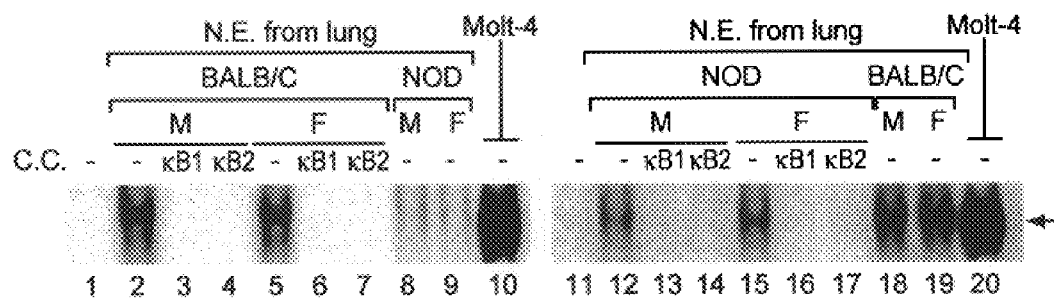

As shown in FIG. 6B, the sequence-specificity of NFκB DNA binding was determined in a competitive binding experiment. Nuclear extracts were incubated with a labeled probe and a molar excess of unlabeled DNA ("cold competitor" or C.C.). Lung tissue nuclear extracts (BALB/C, left panel; NOD right panel) were premixed with cold competitor DNA and incubated for 15 minutes on ice before the labeled nucleic acid probe was added; the two competitor sequences were wild-type sequence κB$_1$: (5'-GATCTAGGGACTTTCCGCTGGGGACTTTCCAG-3' (SEQ ID NO:5) was run in lanes 3, 6, 13 and 16, while wild-type sequence κB$_2$: (5'-GATCTCAGGGGAATCTCCCTCTCCTTTTATGGGC GTAGCG-3' (SEQ ID NO:6) was run in lanes 4, 7, 14 and 17. Nuclear extracts not pre-incubated with cold competitor were run in lanes 2, 5, 8, 9, 10, 12, 15, 18, 19 and 20. The binding reactions were performed at 37° C. for 30 minutes in a total volume of 10 μl of buffer containing: 10 mM Hepes (pH 7.9), 50 mM KCl, 5 mM Tris-HCl (pH 7.0), 1 mM DTT, 15 mM EDTA, 10% (v/v) glycerol, 1.0 μg of poly(dI•dC) and 4 ng of the labeled probe. The DNA-protein complexes were resoled on nondenaturing 8% polyacrylamide gels. Electrophoresis was performed with 0.5×TBE buffer (4.5 mM Tris-HCl, 4.5 mM boric acid, 0.1 mM EDTA) at 4° C. Again, a negative control containing no nuclear extract was run in lane 1.

Figure 6C:
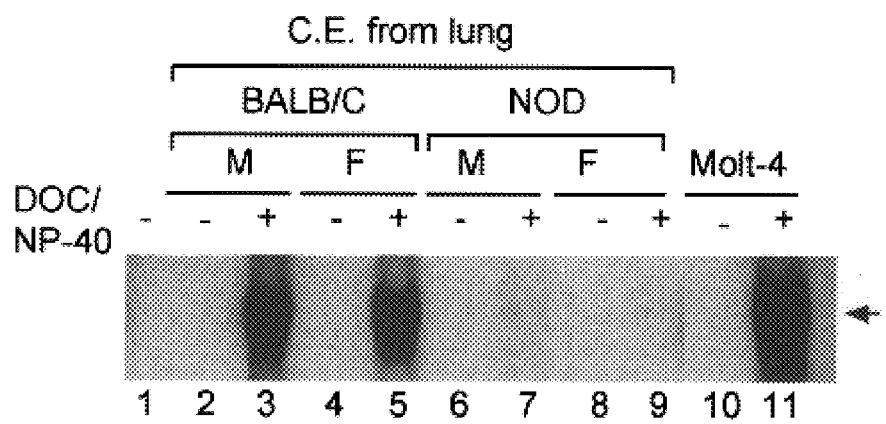

The results of NFκB DNA binding experiments using lung cytosolic extracts are presented in FIG. 6C. As shown, cytosolic NFκB/IκB complexes were identified by EMSA after treatment of cytosolic extracts with 0.8% DOC (deoxycholate) and 1.2% NP-40. Cytosol extracts were prepared as described above from BALB/C (lanes 2–5) and NOD (lanes 6–9) mice and Molt-4 cells (lanes 10–11). These extracts either were ("+", lanes 3, 5, 7, 9 and 11) or were not ("−", lanes 2, 4, 6, 8 and 10) pretreated with the detergents. As above, a negative control reaction to which no extract was added was run in lane 1.

Figure 6D:
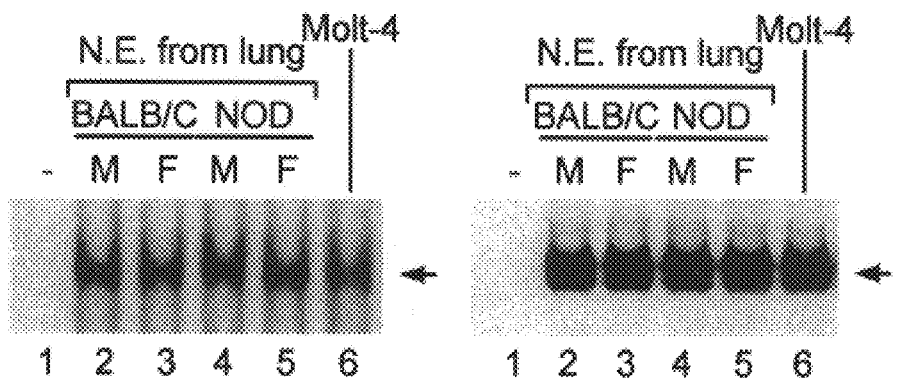

The DNA-binding activities of transcription factors other than NFκB were then assayed; the results of this experiment are shown in FIG. 6D. The binding activities were examined by EMSA using as probe an $^{32}$P end-labeled oligonucleotide containing the SP1 recognition/binding sequence (left panel) or the AP1 recognition/binding sequence (right panel). The respective DNA probes were incubated with nuclear extracts prepared from lung tissue of BALB/C (male, lane 2; female, lane 3) and NOD (male, lane 4; female, lane 5) mice and Molt-4 cells (lane 6); a negative control containing no nuclear extract was run in lane 1. In all panels, protein-DNA complexes were indicated by arrowheads. (M=male; F=female)

As shown in FIG. 6A, nuclear extracts from the NOD mouse do not exhibit NFκB binding activity to a $^{32}$P-end-labeled probe; these data indicate that NFκB activity is virtually absent in NOD mice. The data in FIG. 6B confirm the specificity of NFκB binding to the labeled probe shown in FIG. 6A, since the cold competitive DNA prevented specific binding of protein from the lung extract of BALB/c control mice to the labeled oligonucleotide. The failure to detect active NFκB in either nuclear or cytoplasmic extracts in the NOD mouse indicate that the phenotype is based upon a deficiency in the activity upstream of the transport of NFκB to the nucleus. The integrity of the protein extracts derived from the NOD mice were confirmed in the experiment shown in FIG. 6D, in which the DNA binding capabilities of other transcription factors were assayed and demonstrated to be present; since the DNA-binding activity of two other lymphocyte-expressed transcription factors, SP1 and AP1, were found in the NOD mouse extracts, the observed deficiency appears to be specific to NFκB activation.

Another way of examining transcription factors and their activity is to bind antibodies to the factors and run the complexes on a gel. If the factor is present, the antibody will bind and thus delay migration down the gel; such a procedure is known as a "super-shift" assay. In the experiment shown in FIG. 7A, a labeled DNA probe containing a κB binding sequence was incubated with nuclear extracts prepared from lung tissue of BALB/c (lanes 1–4) and NOD (lanes 5–8) mice and Molt-4 cells (lanes 9–10). Nuclear extracts were pre-incubated either with-("+", even numbered lanes) or without ("−", odd numbered lanes) an anti-p50 polyclonal antibody, and then the labeled DNA probe was added to the reaction mixture.

Figure 7A:
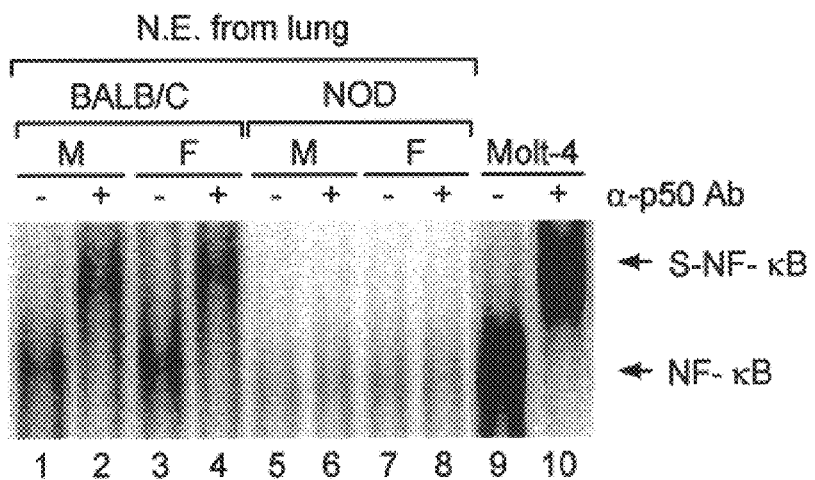
Figure 7B:
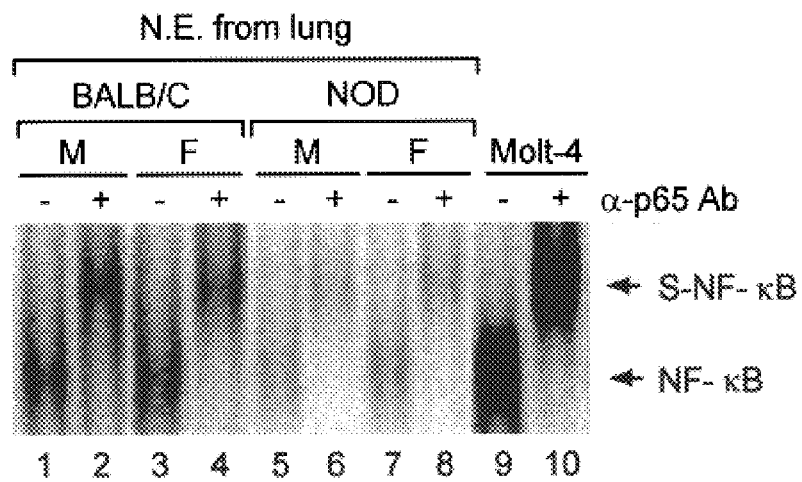

The results of a similar experiment, this time using an anti-p65 polyclonal antibody, are presented in FIG. 7B. Again, nuclear extracts from lung tissue of BALB/c (lanes 1–4) and NOD mice (lanes 5–8) and Molt-4 cells (lanes 9–10) were pre-incubated either with-("+", even number lanes) or without ("−", odd number lane) antibody, and the labeled DNA probe was then added to the reaction mixture.

Figure 7C:
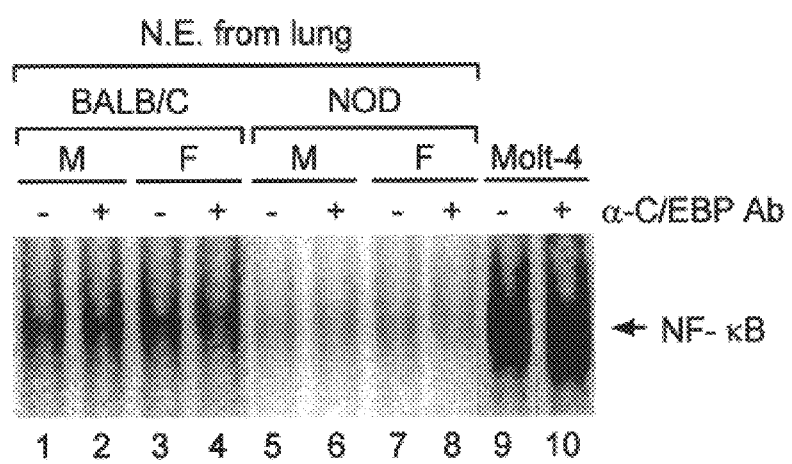

This experiment was repeated using an antibody directed against the CCAAT-Box Enhancer Binding Protein (C/EBP); the identities and treatment of reaction mixtures, as well as their positions on the gel shown in FIG. 7C are otherwise the same as those presented in FIGS. 7A and 7B. In all cases, DNA/NFκB complexes (NF-κB) and super-shifted DNA-protein complexes (S-NF-κB) are indicated by arrows. Nuclear extracts were prepared from both males (M) and females (F).

Taken as a whole, the data presented in FIG. 7 demonstrate that both male and female BALB/C mice possess the activated p50 subunit of NFκB in cell nuclei. In contrast, the activated p50 subunit is virtually absent from the NOD mouse, another active subunit of NFκB is present in nuclei obtained from tissue obtained from this autoimmune strain. When this assay was repeated with a p65 antibody to nuclear extracts of NOD and BALB/c mice, some p65 was detected in the NOD mouse lung nuclear extract. Since this antibody recognizes both the active and inactive forms of p65 we cannot tell from this assay if the reduced amounts of p65 in the nucleus of the NOD were active or inactive. The supershift additionally shows that female NOD mice displays a more extreme reduction in p65 subunits than does the male, while the BALB/c mouse extracts produce a greater amount of antibody-mediated shift than is observed with either gender of autoimmune mutant.

Figure 8A:
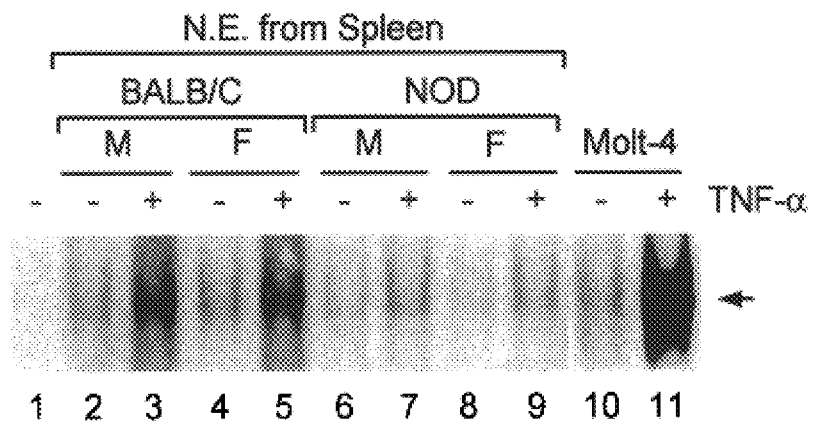

FIG. 8A shows the results of experiments to examine the activation of NFκB nucleic acid-binding by TNF-α treatment. TNF-α is an extracellular signalling molecule which is thought to upregulate NFκB activation in vivo. In order to assess the influence of TNF-α on NFκB in an in vitro system, a DNA/protein binding assay was undertaken. Nuclear extracts were prepared from BALB/C and NOD mice by methods described above. The binding activities were examined by EMSA with $^{32}$P end-labeled oligonucleotide containing an NFκB recognition sequence. Spleen cells were stimulated with TNF-α treatment (+) or without TNF-α treatment (−) and nuclear extracts from the treated cells were prepared 4 hours later. Nuclear extract prepared from spleen cells of BALB/C (lanes 2–5) and NOD (lanes 6–9) mice and Molt-4 cells (lanes 10 and 11) were incubated with DNA probe as follows:

Double-stranded κB wt, κB mut or IL-R2α κB oligonucleotides were end-labeled using [α-$^{32}$P]dCTP and Klenow polymerase. Binding reactions of the DNA probe with nuclear extracts were performed at 37° C. for 30 minutes in a total volume of 10 μl of buffer containing 10 mM Hepes (pH 7.9), 50 mM KCl, 5 mM Tris-HCl (pH 7.0), 1 mM DTT, 15 mM EDTA, 10% (v/v) glycerol, 1.0 μg of poly (dI•dC), and 4 ng of the labeled probe. The DNA-protein complexes were resolved on nondenaturing 8% polyacrylamide gels. Electrophoresis was performed with 0.5×TBE buffer (4.5 mM Tris-HCl, 4.5 mM boric acid, 0.1 mM EDTA) at 4° C. A negative binding control, to which no nuclear extract was added, was run in lane 1.

Figure 8B:
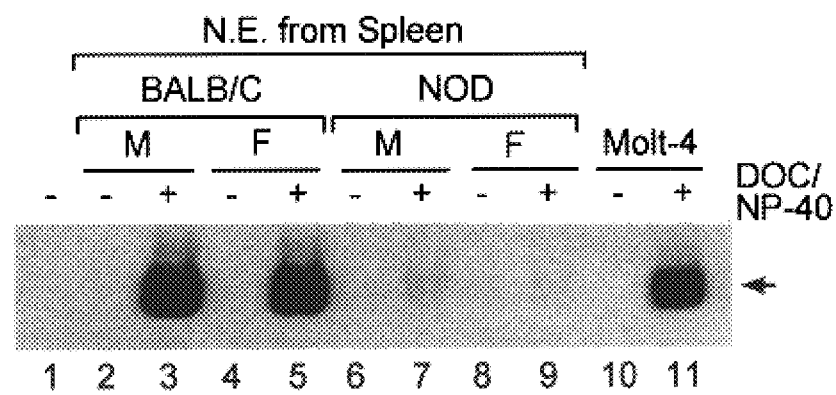
Figure 8C:
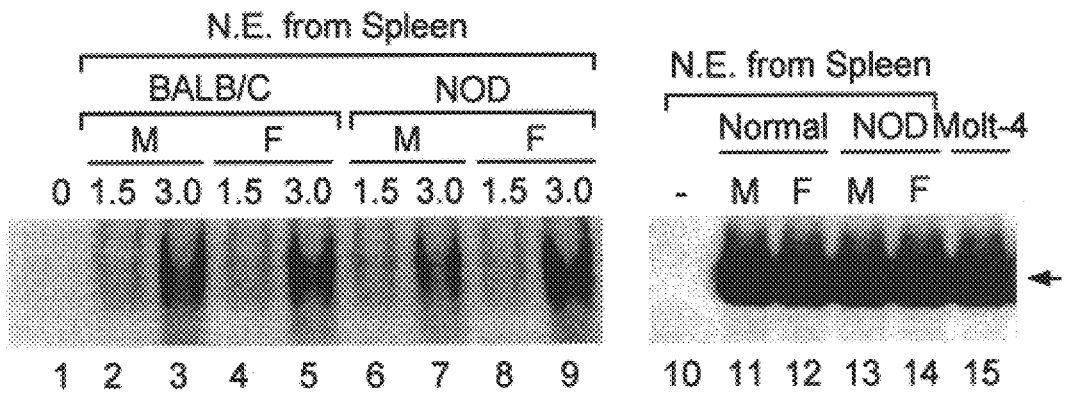

NFκB DNA binding activity was examined in cytosolic extracts (FIG. 8B). Cytosolic NFκB/IκB complexes were identified by EMSA after treatment of cytosolic extracts by 0.8% DOC and 1.2% NP-40. Cytosolic extracts that were not treated with TNF-α were prepared from spleen cells from BALB/C (lanes 2–5) and NOD (lanes 6–9) mice and Molt-4 cells (lanes 10–11). Cytosolic extracts were either pre-treated ("+", lanes 3, 5, 7, 9 and 11) or not pre-treated ("–", lanes 2, 4, 6, 8 and 10) with the detergents. A reaction to which no extract was added was run as a negative control (lane 1).

In addition to NFκB, other transcription factors were examined for DNA binding capability in the NOD mouse model in comparison with that observed in normal mice. The binding activities were examined by EMSA with a $^{32}P$ end-labeled oligonucleotide containing an SP1 recognition site (left) or an AP1 recognition site (right). Appropriate DNA probes were incubated with nuclear extract prepared from lung of BALB/c (male, lanes 2, 3 and 11; female, lanes 4, 5 and 12) and NOD mice (male, lanes 6, 7 and 13; female, lanes 8, 9 and 14) and Molt-4 cells (lane 15); again, a negative control reaction, to which no DNA probe was added, was run in lanes 1 and 10. In each of FIGS. 8A, 8B and 8C, protein-DNA complexes are indicated by arrowheads. Nuclear extracts were prepared from spleen cells derived from BALB/C or NOD mice. M=male; F=female.

As FIG. 8A clearly shows in spleen cell extracts, TNF-α is only able to activate NFκB in the BALB/c mouse and in the Molt-4 lymphoid cell line; NOD mice do not show increased p65 activity, suggesting a disruption of normal intracellular signalling pathways of p65-mediated protection from TNF-κ stimulation.

In order to confirm the identities of nuclear proteins binding to κB sites following TNF-α stimulation, a super-shift assay was performed. A labeled DNA probe containing a κB binding sequence was incubated with nuclear extracts prepared from spleen cells after TNF-α treatment. Spleen cells were pre-stimulated by TNF-α treatment for 4 hours. Nuclear extracts were pre-incubated with an anti-p50 polyclonal antibody (lanes 3 and 7), anti-p65 polyclonal antibody (lanes 4 and 8), anti-C/EBP polyclonal antibody (lanes 5 and 9) or without antibody ("–", lanes 1, 2 and 6); BALB/C (upper panel), NOD (lower panel). The labeled DNA probe was then added to the reaction mixture. Again, a control reaction to which no nuclear extract was added was run in lane 1 as a negative control. In all panels, DNA/NFκB complexes (NF-κB) and super-shifted DNA-protein complexes (S-NF-κB) were indicated by arrows. Nuclear extracts were prepared from males (M) and females (F).

As in previous experiments, the prominent finding is that in TNF-α-stimulated Balb/c mice, the nucleus possesses an abundance of the active form of NFκB (i.e., p50), as demonstrated by supershift. In contrast, the NOD mouse appears unresponsive for p50 activation, even after exposure to a stimulant of NFκB activation.

One critical function of NFκB is to provide protection to cells from the effects of exogenous TNF-α. In the experiment show in FIG. 10A, spleen cells were prepared from BALB/c and NOD mice, and tested for survival following TNF-α stimulation. Spleen cells were cultured for 24 hours after exposure to various concentrations (2, 5, 10 or 20 ng/ml) of TNF-α, as indicated on the X axis of the figure. Viable cells remaining after TNF-α treatment are shown as a percentage of viable control (untreated) cells. Standard deviations were calculated from four independent readings within a single experiment. The survival over time of cells treated with TNF-α is charted in FIG. 10B. Spleen cells were treated with TNF-α (10 ng/ml), and viable cells were counted at various times following treatment as indicated on the X axis of the figure, These data clearly demonstrate that TNF-α treatment is toxic to NOD mice and the cells experience rapid death. That the survival of NOD mice is compromised with regard to that of normal mice indicates clearly that NFκB activation is defective in this autoimmune mouse model.

Use

The invention is of use in the diagnosis and treatment of autoimmune disorders

Other Embodiments

Other embodiments will be evident to those of skill in the art. It should be understood that the foregoing description is provided for clarity only and is merely exemplary. The spirit and scope of the present invention are not limited to the above examples, but are encompassed by the following claims.

What is claimed is:

1. A method of screening for autoimmune disease associated with a reduction in NFκB activity in a mammal deemed to be at risk for an autoimmune disease comprising:
   a) providing a biological sample from a mammal; and
   b) measuring the level of proteolytic products derived from the proteolytic processing of NFκB in said sample, wherein a reduction in the level of said proteolytic products from a basal state is correlated with the presence of an autoimmune disease associated with a reduction in NFκB activity.

2. The method of claim 1, wherein said mammal is a human.

3. The method of claim 1, wherein said reduction in said proteolytic products is determined by measuring the level of said proteolytic products in the nucleus of the cell.

4. The method of claim 1, wherein said reduction in said proteolytic products is determined by measuring the level of said proteolytic products in the cytoplasm of the cell.

* * * * *

UNITED STATES PATENT AND TRADEMARK OFFICE
CERTIFICATE OF CORRECTION

PATENT NO.     : 6,617,171 B2                                              Page 1 of 1
DATED          : September 9, 2003
INVENTOR(S)    : Denise L. Faustman et al.

It is certified that error appears in the above-identified patent and that said Letters Patent is hereby corrected as shown below:

Column 1,
Line 3, insert the following:
-- This invention was made with Government support under Contract number R03DE11023 awarded by the National Institute of Health. The Government has certain rights in this invention. --

Signed and Sealed this

Second Day of December, 2003

JAMES E. ROGAN
*Director of the United States Patent and Trademark Office*

UNITED STATES PATENT AND TRADEMARK OFFICE
CERTIFICATE OF CORRECTION

PATENT NO.     : 6,617,171 B2
DATED          : September 9, 2003
INVENTOR(S)    : Denise L. Faustman et al.

It is certified that error appears in the above-identified patent and that said Letters Patent is hereby corrected as shown below:

Column 1,
Line 3, insert the following:
-- This invention was made with Government support under Grant No. 5R01-DE1151 awarded by the National Institutes of Health. The Government has certain rights in this invention. --

This certificate supersedes Certificate of Correction issued December 2, 2003.

Signed and Sealed this

Nineteenth Day of April, 2005

JON W. DUDAS
*Director of the United States Patent and Trademark Office*

SEQUENCE LISTING

```
<160> NUMBER OF SEQ ID NOS:  6

<210> SEQ ID NO 1
<211> LENGTH: 4
<212> TYPE: PRT
<213> ORGANISM: Artificial Sequence
<220> FEATURE:
<223> OTHER INFORMATION: Description of Artificial Sequence: Fluorogenic
      peptide used for degradation assays
<221> NAME/KEY: SITE
<222> LOCATION: (4)
<223> OTHER INFORMATION: 7-amino-4-methylcoumarin is attached to the
      C-terminal Tyr
<221> NAME/KEY: SITE
<222> LOCATION: (1)
<223> OTHER INFORMATION: The N-terminal Leu contains a succinyl
      modification

<400> SEQUENCE: 1

Leu Leu Val Tyr Xaa
  1               5
```

-continued

```
<210> SEQ ID NO 2
<211> LENGTH: 3
<212> TYPE: PRT
<213> ORGANISM: Artificial Sequence
<220> FEATURE:
<223> OTHER INFORMATION: Description of Artificial Sequence: Fluorogenic
      peptide used for degradation assays
<221> NAME/KEY: SITE
<222> LOCATION: (3)
<223> OTHER INFORMATION: 7-amido-4-methylcoumarin is attached to the
      C-terminal Arg
<221> NAME/KEY: SITE
<222> LOCATION: (1)
<223> OTHER INFORMATION: The N-terminal Leu contains a tert-butyoxycarbonyl
      modification

<400> SEQUENCE: 2

Leu Arg Arg Xaa
  1

<210> SEQ ID NO 3
<211> LENGTH: 3
<212> TYPE: PRT
<213> ORGANISM: Artificial Sequence
<220> FEATURE:
<223> OTHER INFORMATION: Description of Artificial Sequence: Fluorogenic
      peptide used for degradation assays
<221> NAME/KEY: SITE
<222> LOCATION: (3)
<223> OTHER INFORMATION: beta-napthylamide is attached to the C-terminal
      Glu
<221> NAME/KEY: SITE
<222> LOCATION: (1)
<223> OTHER INFORMATION: The N-terminal Leu contains a carbenzoyx
      modification

<400> SEQUENCE: 3

Leu Leu Glu Xaa
  1

<210> SEQ ID NO 4
<211> LENGTH: 6
<212> TYPE: PRT
<213> ORGANISM: Artificial Sequence
<220> FEATURE:
<223> OTHER INFORMATION: Description of Artificial Sequence: Heptapeptide
      from the carboxy-terminal domain of RNA polymerase
      II large subunit

<400> SEQUENCE: 4

Tyr Ser Pro Thr Pro Ser
  1               5

<210> SEQ ID NO 5
<211> LENGTH: 32
<212> TYPE: DNA
<213> ORGANISM: Artificial Sequence
<220> FEATURE:
<223> OTHER INFORMATION: Description of Artificial Sequence: Probe for
      wild-type kappa B1 sequence

<400> SEQUENCE: 5
gatctaggga ctttccgctg gggactttcc ag                                        32

<210> SEQ ID NO 6
<211> LENGTH: 40
<212> TYPE: DNA
<213> ORGANISM: Artificial Sequence
<220> FEATURE:
<223> OTHER INFORMATION: Description of Artificial Sequence: Probe for
      wild-type kappa B2 sequence
```

-continued

<400> SEQUENCE: 6

```
gatctcaggg gaatctccct ctccttttat gggcgtagcg                    40
```